United States Patent
Dijcks et al.

(10) Patent No.: US 9,540,361 B2
(45) Date of Patent: Jan. 10, 2017

(54) N-SUBSTITUTED AZETIDINE DERIVATIVES

(75) Inventors: Fredericus Antonius Dijcks, Oss (NL); Scott James Lusher, Den Bosch (NL); Herman Thijs Stock, Wijchen (NL); Arthur Oubrie, Wijchen (NL); Gerrit Herman Veeneman, Schaijk (NL)

(73) Assignee: Merck Sharp & Dohme B.V., Haarlem (NL)

( * ) Notice: Subject to any disclaimer, the term of this patent is extended or adjusted under 35 U.S.C. 154(b) by 314 days.

(21) Appl. No.: 13/995,237

(22) PCT Filed: Dec. 16, 2011

(86) PCT No.: PCT/EP2011/073041
§ 371 (c)(1),
(2), (4) Date: Apr. 21, 2015

(87) PCT Pub. No.: WO2012/084711
PCT Pub. Date: Jun. 28, 2012

(65) Prior Publication Data
US 2016/0130262 A1    May 12, 2016

(30) Foreign Application Priority Data
Dec. 24, 2010  (EP) .................................. 10196960

(51) Int. Cl.
| | | |
|---|---|---|
| C07D 417/14 | (2006.01) | |
| C07D 413/12 | (2006.01) | |
| C07D 417/12 | (2006.01) | |
| C07D 413/14 | (2006.01) | |
| C07D 205/04 | (2006.01) | |
| C07D 405/12 | (2006.01) | |
| C07D 409/12 | (2006.01) | |
| C07D 409/14 | (2006.01) | |

(52) U.S. Cl.
CPC ........... *C07D 413/14* (2013.01); *C07D 205/04* (2013.01); *C07D 405/12* (2013.01); *C07D 409/12* (2013.01); *C07D 409/14* (2013.01); *C07D 413/12* (2013.01); *C07D 417/12* (2013.01); *C07D 417/14* (2013.01)

(58) Field of Classification Search
None
See application file for complete search history.

(56) References Cited

U.S. PATENT DOCUMENTS

2006/0116364 A1*  6/2006  Hamaoka .............. C07C 215/78
                                                            514/217.01

FOREIGN PATENT DOCUMENTS

| EP | 1 577 288 A1 | 12/2003 |
| WO | 03/070675 A2 | 8/2003 |
| WO | 03/070675 A3 | 8/2003 |
| WO | 03/086388 A1 | 10/2003 |
| WO | 03/087073 A1 | 10/2003 |
| WO | 03/091239 A1 | 11/2003 |

OTHER PUBLICATIONS

Bradley, D. A. et al., "Synergistic methodologies for the synthesis of 3-aroyl-2-arylbenzo[b]thiophene-based selective estrogen receptor modulators. Two concise syntheses of raloxifene", Tetrahedron Letters, 1999, p. 5155-5159, vol. 40.
Bulun, S. E. et al., "Mechanisms of Disease Endometriosis", The New England Journal of Medicine, 2009, p. 268-279, vol. 360.
Cleator, S. J. et al., "A 2009 Update on the Treatment of Patients with Hormone Receptor-Positive Breast Cancer", Clinical Breast Cancer, 2009, p. S6-S17, vol. 9, Suppl. 1.
Clinton, G. M. et al., "Estrogen action in human ovarian cancer", Critical Reviews in Oncology/Hematology, 1997, p. 1-9, vol. 25.
De Gooyer, M. E. et al., "Receptor profiling and endocrine interactions of tibolone", Steroids, 2003, p. 21-30, vol. 68.

(Continued)

*Primary Examiner* — Michael Barker
(74) *Attorney, Agent, or Firm* — Baerbel R. Brown; Catherine D. Fitch

(57) ABSTRACT

The present invention relates to novel N-substituted azetidine derivatives < of the formula (I); wherein SERMF is a Selective Estrogen Receptor Modilator fragment; X is no atom, O, S, CH2, carbonyl, N—R5; R1 is H, (C1-8)alkyl, (C3-8)cycloalkyl, (C3-6)heterocycloalkyl, (C2-6)alkenyl, (C2-6)alkynyl, (C1-4)alkylcarbonyl, (C1-4)alkoxy(C2-4)alkyl, (C3-6)cycloalkyl(C1-3)-alkyl, (C3-6)heterocycloalkyl(C1-3)alkyl, each independently optionally substituted with one or more halogen, nitrile, hydroxyl or (C1-2)alkyl; R5 is H, (C1-3)alkyl, optionally substituted with one or more fluorine; R17, R18 and R19 are independently of each other H, fluorine, nitrile or (C1-3)-alkyl, optionally substituted with one or more fluorine; or a prodrug, isotopically-labelled derivative or pharmaceutically acceptable salt thereof, > to pharmaceutical compositions comprising these compounds and to their use in therapy, in particular to their use for the prevention or treatment of ovulatory dysfunction, uterine cancer, endometrium cancer, ovarian cancer, endometriosis, osteoporosis, prostate cancer, benign prostatic hypertrophy, and breast cancer, in particular ER-positive breast cancer, more in particular ER-positive, hormone treatment-resistant breast cancer. Said N-substituted azetidine derivatives have estrogen receptor alpha (ERa) antagonistic and—in certain embodiments—selective estrogen receptor downregulating (SERD) activity in ER-positive breast cancer cells.

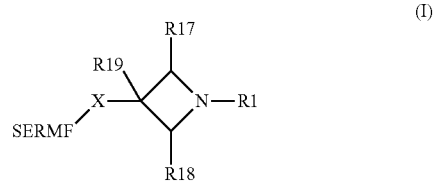

(I)

9 Claims, No Drawings

(56) References Cited

OTHER PUBLICATIONS

Deshmane, V. et al., "Phase III Double-Blind Trial of Arzoxifene Compared With Tamoxifen for Locally Advanced or metastatic Breast Cancer", Journal of Clinical Oncology, 2007, p. 4967-4973, vol. 25.

Ellem. S. J. et al., "Treating prostate cancer: a rationale for targeting local oestrogens", Nature Reviews, 2007, p. 621-627, vol. 7.

Fan. M. et al., "Characterization of molecular and structural determinants of selective estrogen receptor downregulators", Breast Cancer Res Treat, 2007, p. 37-44, vol. 103.

Howell, A. et al., "Comparison of Fulvestrant Versus Tamoxifen for the Treatment of Advanced Breast Cancer in Postmenopausal Women Previously Untreated With Endocrine Therapy: A Multinational, Double-Blind, Randomized Trial", Journal of Clinical Oncology, 2004, p. 1605-1613, vol. 22, No. 9.

Jordan, V. C. et al., "Antiestrogens and Selective Estrogen Receptor Modulators as Moltifunctional Medicines. 1. Receptor Interactions", Journal of Medicinal Chemistry, 2003, p. 883-908, vol. 46, No. 6.

Jordan, V. C., Pak up Your Breast Tumor—and Grow!, Journal of the National Cancer Institute, 2006, p. 657-659, vol. 98, No. 10.

Jordan, V. C., "Tamoxifen: A Most Unlikely Pioneering Medicine", Nature Reviews, 2003, p. 205-213, vol. 2.

Jordan, V. C. et al., "Selective Estrogen-Receptor Modulators and Antihormaonal Resistance in Breast Cancer", Journal of Clinical Oncology, 2007, p. 5815-5824, vol. 25, No. 36.

Linden, H. M. et al., "PET FES measures in vivo pharmacodynamics of endocrine therapy", Journal of Clinical Oncology, 2007, p. 14110, vol. 25, No. 18S.

Miller, C. P., "SERMs: Evolutionary Chemistry, Revolutionary Biology", Current Pharmaceutical Design, 2002, p. 2089-2111, vol. 8.

Palkowitz, A. D. et al., "Discovery and Synthesis of [6-Hydroxy-3-[4-[2-(1-piperidinyl)ethoxy]phenoxy]-2-(4-hydroxyphenyl)benzo[b]thiophene: A Novel, Highly Potent, Selective Estrogen Receptor Modulator", Journal of Medicinal Chemistry, 1997, p. 1407-1416, vol. 40, No. 10.

Pickar, J. H. et al., "SERMs: Progress and future perspectives", Maturitas, 2010, p. 129-138, vol. 67.

Robertson, F. et al., "The pan-HDAC Inhibitor Suberoylanilide Hydroxamic Acid Targets Self Renewal of Breast Cancer Stem Cells", Cancer Research, 2009, vol. 69, Issue 24, Suppl 3.

Steiner, A. Z. et al., "Comparison of tamoxifen and clomiphene citrate for ovulation induction: a meta-analysis", Human Reproduction, 2005, p. 1511-1515, vol. 20, No. 6.

Stella, V. J. et al., "Prodrug strategies to overcome poor water solubility", Advanced Drug Delivery Reviews, 2007, p. 677-694, vol. 59.

Ullrich, J. W. et al., "Estrogen receptor modulator review", Expert Opinion Ther. Patents, 2006, p. 559-572, vol. 16, No. 5.

Yang, C. et al., "Benzothiophenes containing a peperazine side chain as selective ligands for the estrogen receptor alpha and their bioactivities in vivo", Bioorganic & Medicinal Chemistry Letters, 2005, p. 1505-1507, vol. 15.

Blizzard, T. A. et al., "Estrogen receptor ligands. Part 9: Dihydrobenzoxathiin SERAMs with alkyl substituted pyrrolidine side chains and linkers", Bioorganic & Medicinal Chemistry Letters, 2005, p. 107-113, vol. 15.

\* cited by examiner

N-SUBSTITUTED AZETIDINE DERIVATIVES

CROSS-REFERENCE TO RELATED APPLICATIONS

This application is a U.S. National Phase application under 35 U.S.C. §371 of PCT Application No. PCT/EP2011/073041, filed on Dec. 16, 2011, which claims priority from and the benefit of EP Priority Application No. 10196960.8, filed Dec. 24, 2010.

FIELD OF INVENTION

The present invention relates to a new series of N-substituted azetidine derivatives, i.e. a series of Selective Estrogen Receptor Modulator (SERM) fragments derivatized with an N-substituted azetidine group, to pharmaceutical compositions comprising these compounds, and to their use in therapy, in particular to their use for the prevention or treatment of ovulatory dysfunction, uterine cancer, endometrium cancer, ovarian cancer, endometriosis, osteoporosis, prostate cancer, benign prostatic hypertrophy, and breast cancer, in particular estrogen receptor (ER)-positive breast cancer, more in particular ER-positive hormone treatment-resistant breast cancer. In one embodiment, the new compounds contain an N-substituted azetidine moiety, attached via an ether linkage to SERM-derived chemical scaffolds which are estrogen receptor alpha antagonists.

BACKGROUND OF THE INVENTION

The estrogen receptor (ER) is a ligand-activated transcription factor that belongs to the nuclear hormone receptor superfamily. Estrogens play an important role in the regulation of a number of physiological processes, both in females and males. In humans, two different ER subtypes are known: ERα and ERβ, each with a distinct tissue distribution and with different biological roles. ERα has high presence in endometrium, breast cancer cells, ovarian stroma cells, and in the hypothalamus. The expression of the ERβ protein has been documented in kidney, brain, bone, heart, lungs, intestinal mucosa, prostate, bladder, ovary, testis, and endothelial cells. For a review see: J. W. Ullrich and C. P. Miller, Expert Opin. Ther. Patents, 16 (2006) 559-572.

Well-known examples of SERMs are tamoxifen and raloxifene. Tamoxifen, for example, behaves like an estrogen in bone and endometrium, whereas it behaves like an anti-estrogen in breast tissue. SERMs are furthermore characterized by two common structural features: a phenolic hydroxyl group (or a bioisostere thereof) and a side chain containing a basic amine. At the time of administration in vivo, the hydroxyl group of a SERM may not yet be present; it may be formed in vivo by de-masking of a prodrug (for example by demethylation of a phenolic methoxy group or by hydrolysis of a phenolic ester group) or by metabolic introduction (for example the metabolic conversion of tamoxifen into 4-hydroxy-tamoxifen, an active metabolite of tamoxifen). Examples of side chains containing a basic amine are 2-(dimethylamino)ethoxy (like in tamoxifen), 2-(1-piperidinyl)ethoxy (like in raloxifene), and 2-(1-pyrrolidinyl)ethoxy (like in lasofoxifene). Upon binding of a SERM to the estrogen receptor, the basic amine in the side chain forms an interaction with amino acid residue Asp351 (in ERα) or Asp303 (in ERβ) resulting in a conformational change of the receptor. For reviews on SERMs see: C. P. Miller, Current Pharmaceutical Design 8 (2002) 2089-2111; V. C Jordan, J. Med. Chem. 46 (2003) 883-908, and J. H. Pickar et al.; Maturitas 67 (2010) 129-138.

Breast cancer is the predominant neoplastic disease in women. ERα is a major driver of breast cancer progression. Multiple existing treatment approaches aim to reduce estrogen levels or block its binding to ERα thereby minimizing tumor progression or even inducing tumor regression in ER-positive breast cancer. Tamoxifen is a first generation SERM used for first-line treatment of ER-positive breast cancer (see V. C. Jordan, Nature Reviews Drug Discovery, 2 (2003) 205-213). Efficacy in breast cancer treatment is seriously compromised by intrinsic or newly developed resistance to anti-hormonal therapy such as treatment with tamoxifen or aromatase inhibitors. Such resistance can exist or develop as a result of ER phoshorylation or regulation of key components in hormone receptor and/or growth factor signal transduction pathways (see V. C. Jordan and B. W. O'Malley, J. Clin. Oncol. 25 (2007) 5815-5824; V. C. Jordan, J. Nat. Cancer Inst., 98 (2006) 657-659; S. J. Cleator et al., Clinical Breast Cancer 9 (2009) S6-S17).

Tamoxifen resistance is driven by the residual agonist activity of tamoxifen and its 4-OH metabolites. Second generation SERMs such as toremifene, droloxifene, idoxifene, arzoxifene, and raloxifene have failed to improve upon the efficacy of tamoxifen in the treatment of ER-positive breast cancer and/or demonstrated cross-resistance with each other (V. Deshmane et al., J. Clin. Oncol. 25 (2007) 4967-4973); J. H. Pickar et al., Maturitas 67 (2010) 129-138).

Fulvestrant, a steroidal C7-substituted 17β-estradiol derivative and a pure ER antagonist without the partial agonist activity which is so typical for the SERMs, is the only marketed SERD (Selective Estrogen Receptor Downregulator) efficacious in second-line treatment of breast cancer. Besides antagonizing ERs, fulvestrant also effectively downregulates ERα protein levels in cells. This SERD activity inhibits ERα-driven proliferation and tumor growth (in contrast to tamoxifen which upregulates ERα). Fulvestrant, when administered i.m. once a month at 250 mg is equally effective to tamoxifen in treatment of ER-positive advanced breast cancer (A. Howell et al., J. Clin. Oncol. 22 (2004) 1605-1613). In second-line treatment of ER-positive tamoxifen-resistant breast cancer, fulvestrant, when administered i.m. once a month at 250 mg, is equally effective to aromatase inhibitors, despite relatively poor bioavailability and/or target exposure which limits its clinical efficacy (Robertson et al., San Antonio Breast Cancer Symposium, 2009; Linden et al., San Antonio breast Cancer Symposium, 2007).

Other known SERDs are ICI 164,384, i.e. a structural analogue of fulvestrant, GW5638, i.e. a structural analogue of tamoxifen, and GW7604, i.e. a structural analogue of 4-hydroxy-tamoxifen. For a review on SERDs see: M. Fan et al., Breast Cancer Res. Treat. 103 (2007) 37-44.

Merck has reported a series of 2,3-dihydrobenzo[b][1,4]-oxathiine derivatives, in which a modified (i.e. a bis-methylated pyrrolidinylethoxy) basic amine side chain all at once behaved as a SERD instead of as a SERM. However, when said modified basic amine side chain was placed on other SERM-derived chemical scaffolds, such as the benzothiophene of raloxifene, the tetrahydronaphthalene of lasofoxifene and the indole of bazedoxifene, these modified compounds did not behave as SERDs. See page 561 of J. W. Ullrich and C. P. Miller, Expert Opin. Ther. Patents, 16 (2006) 559-572, and references 18 and 101-103 cited therein.

Hence, there is a need for new, potent ERα antagonists, which would preferably have ER downregulating activity (in breast cancer cells), do not stimulate proliferation in ER-positive, hormone treatment-resistant breast cancer cells, be orally administrable, and be useful in the treatment of inter alia ER-positive, hormone treatment-resistant breast cancer.

Apart from the treatment of breast cancer, SERMs have also been used in the treatment of a number of other disorders and/or diseases. The treatment of ovulatory dysfunction by tamoxifen and clomiphene citrate, which induce ovulation, is described by A. Steiner et al. in *Human Reproduction* 20 (2005) 1511-1515; and by J. H. Pickar et al. in *Maturitas* 67 (2010) 129-138. J. H. Pickar et al. in *Maturitas* 67 (2010) 129-138 also describe the treatment of uterine cancer, endometrium cancer, osteoporosis, prostate cancer, and benign prostatic hypertrophy using SERMs. S. J. Ellem and G. P. Risbridger in *Nature Reviews Cancer* 7 (2007) 621-627 also describe the treatment of prostate cancer and benign prostatic hyperplasia (or hypertrophy). The treatment of ovarian cancer is described by G. M. Clinton and W. Hua in *Crit. Rev. Oncol. Hematol.* 25 (1997) 1-9. S. E. Bulun in *N. Engl. J. Med.* 360 (2009) 268-279 reviews the role of estrogen and estrogen receptor signaling in endometriosis.

DETAILED DESCRIPTION OF THE INVENTION

The present invention provides a series of N-substituted azetidine derivatives of the following Formula 1

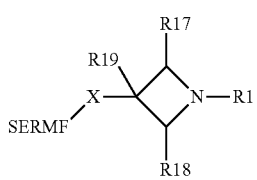

Formula 1 wherein

SERMF is a Selective Estrogen Receptor Modulator fragment;

X is no atom, O, S, $CH_2$, carbonyl, N—R5;

R1 is H, (C1-8)alkyl, (C3-8)cycloalkyl, (C3-6)heterocycloalkyl, (C2-6)alkenyl, (C2-6)alkynyl, (C1-4)alkylcarbonyl, (C1-4)alkoxy(C2-4)alkyl, (C3-6)cycloalkyl(C1-3)alkyl, (C3-6)heterocycloalkyl(C1-3)alkyl, each independently optionally substituted with one or more halogen, nitrile, hydroxyl or (C1-2)alkyl;

R5 is H, (C1-3)alkyl, optionally substituted with one or more fluorine;

R17, R18 and R19 are independently of each other H, fluorine, nitrile or (C1-3)-alkyl, optionally substituted with one or more fluorine;

or a prodrug, isotopically-labelled derivative or pharmaceutically acceptable salt thereof.

The N-substituted azetidine derivatives of the present invention are generally derived from the corresponding SERMs in which a SERM fragment (abbreviated as SERMF), e.g. the substituted benzothiophene of raloxifene, the substituted tetrahydronaphthalene of lasofoxifene, the substituted indole of bazedoxifene, the substituted trans-1,2-diphenylbut-1-ene of tamoxifen etc., instead of being connected to a basic amine side chain, i.e. the piperidinylethyloxy moiety of raloxifene, the pyrrolidinylethyloxy moiety of lasofoxifene, the homopiperidinylethyloxy moiety of bazedoxifene or the dimethylaminoethyloxy moiety of tamoxifen etc., is now connected to an N-substituted azetidine-X moiety, in particular an N-substituted azetidinyl-3-oxy moiety. For a review on a whole variety of suitable SERM fragments, see J. W. Ullrich and C. P. Miller, in *Expert Opin. Ther. Patents*, 16 (2006) 559-572.

The term (C1-8)alkyl means a linear or branched alkyl chain having 1-8 carbon atoms, for example methyl, ethyl, n-propyl, isopropyl, n-butyl, isobutyl, sec-butyl, tert-butyl, n-pentyl, and n-octyl.

The term (C1-6)alkyl means a linear or branched alkyl chain having 1-6 carbon atoms, for example methyl, ethyl, n-propyl, isopropyl, n-butyl, isobutyl, sec-butyl, tert-butyl, n-pentyl and n-hexyl.

The term (C1-4)alkyl means a linear or branched alkyl chain having 1-4 carbon atoms, being methyl, ethyl, n-propyl, isopropyl, n-butyl, isobutyl, sec-butyl and tert-butyl.

The term (C1-3)alkyl means a linear or branched alkyl chain having 1-3 carbon atoms, being methyl, ethyl, n-propyl and isopropyl.

The term (C1-2)alkyl means a alkyl chain having 1-2 carbon atoms, being methyl and ethyl.

The term (C3-8)cycloalkyl means a cycloalkyl group having 3-8 carbon atoms, such as cyclopropyl, ethylcyclopropyl, cyclobutyl, methylcyclobutyl, cyclopentyl, cyclohexyl and bicyclo[2.2.1]heptyl.

The term (C3-6)cycloalkyl means a cycloalkyl group having 3-6 carbon atoms, such as cyclopropyl, ethylcyclopropyl, cyclobutyl, methylcyclobutyl, cyclopentyl, cyclohexyl and bicyclo[1.1.1]pentyl.

The term (C3-6)heterocycloalkyl means a heterocycloalkyl group having 3-6 carbon atoms and 1-2 heteroatoms selected from N, O and/or S, which is attached via carbon atom. Examples are oxetanyl, methyloxetanyl, tetrahydrofuranyl, tetrahydropyranyl, pyrrolidinyl, tetrahydrothiopyranyl and oxazepanyl.

The term (C2-6)alkenyl means a branched or unbranched alkenyl group having 2-6 carbon atoms, such as ethenyl, 2-propen-1-yl, 2-butenyl and n-pentenyl.

The term (C2-6)alkynyl means a branched or unbranched alkynyl group having 2-6 carbon atoms, such as ethynyl, 2-propyn-1-yl, 2-butynyl and n-pentynyl.

The term (C1-4)alkylcarbonyl means an alkylcarbonyl group, the alkyl group of which is a branched or unbranched alkyl group having 1-4 carbon atoms, as defined hereinabove, connected via a carbonyl group.

The term (C1-6)alkoxy means alkyloxy group, the alkyl group of which is a branched or unbranched alkyl group having 1-6 carbon atoms, as defined hereinabove, connected via the oxygen atom. Examples are methoxy, ethoxy, propoxy, isopropoxy and hexyloxy.

The term (C1-3)alkoxy means alkyloxy group, the alkyl group of which is a branched or unbranched alkyl group having 1-3 carbon atoms, as defined hereinabove, connected via the oxygen atom. Examples being methoxy, ethoxy, propoxy and isopropoxy.

The term (C1-3)alkylthio means alkylthio group, the alkyl group of which is a branched or unbranched alkyl group having 1-3 carbon atoms, connected via the sulfur atom, being methylsulfanyl, ethylsulfanyl, propylsulfanyl and isopropylsulfanyl.

The term (C1-4)alkoxy(C2-4)alkyl as used herein means an alkyl group having 2-4 carbon atoms, to which an alkoxy group is attached, connected via the oxygen atom, with the alkoxy group having 1-4 carbon atoms. Examples are 2-methoxyethyl, 3-methoxypropyl, propoxymethyl and 2-ethoxyethyl.

The term (C1-2)alkoxy(C2-4)alkyl as used herein means an alkyl group having 2-4 carbon atoms, to which an alkoxy group is attached, connected via the oxygen atom, with the alkoxy group having 1-2 carbon atoms. Examples are 2-methoxyethyl, 3-methoxypropyl and 2-ethoxyethyl.

The term (C3-6)cycloalkyl(C1-3)alkyl as used herein means an alkyl group having 1-3 carbon atoms, to which a cycloalkyl substituent is attached having 3-6 carbon atoms. Examples are cyclopropylmethyl, cyclobutylethyl and methylcyclobutylmethyl.

The term (C3-6)heterocycloalkyl(C1-3)alkyl as used herein means an alkyl group having 1-3 carbon atoms, to which a (C3-6)heterocycloalkyl substituent is attached with the same meaning as previously defined. Examples are oxetanylmethyl, tetrahydofuranylmethyl, tetrahydropyranylethyl and N-methylazetidinylmethyl.

The term halogen means fluorine, chlorine, bromine and iodine, in particular fluorine and chlorine, more in particular fluorine.

Depending on the nature of the scaffold or the substituents on the structures in Formula 1 or in other Formulae described hereinbelow, the compounds of this invention can exist as a racemic mixture of enantiomers, containing substantially equal amounts of the two enantiomers, as mixtures of enantiomers in any proportions or as the pure enantiomers. The present invention includes the aforementioned mixtures and racemic mixtures within its scope and each of the individual (+) and (−) enantiomers substantially free of the other enantiomer, i.e. an enantiomer associated with less than 5%, preferably less than 2%, in particular less than 1% of the other enantiomer.

Depending on the nature of the scaffold or the substituents on the structures in Formulae 1 or in other Formulae described hereinbelow, the compounds of this invention can exist as a mixture of diastereomers. The present invention includes the aforementioned mixture of diastereomers within its scope and each of the individual diastereomers substantially free of another diastereomer, i.e. a diastereomer associated with more than 95%, preferably more than 98%, in particular more than 99% diastereomeric excess.

A prodrug is defined as being a compound which is converted in the body of a recipient to a compound as defined by Formula 1 or by other Formulae described hereinbelow. Notably, a phenolic hydroxyl group at the A-ring of the skeleton of Formula 1 can for example be substituted by an alkyl, alkenyl, acyl, aroyl, alkoxycarbonyl, alkylsulfonyl, arylsulfonyl, alkylsulfamate, arylsulfamate, phosphate group or glycosyl group, whereby the carbon chain length is not considered to be sharply delimited, while aroyl and aryl generally will comprise a phenyl, pyridinyl or pyrimidinyl, which groups can have substitutions customary in the art, such as alkyl, hydroxy, halogen, nitro, cyano, and (mono-, or dialkyl)amino groups. The carbon chain length is selected depending on the desired properties of the prodrugs, whereby the longer chained prodrugs with for example lauryl or caproyl chains generally are more suitable for sustained release and depot preparations. It is known that such substituents spontaneously hydrolyze or are enzymatically hydrolyzed to the free hydroxyl substituents on the skeleton of the compound. Such prodrugs will have biological activity comparable to the compounds to which they are converted in the body of the recipients. The active compound to which a prodrug is converted is called the parent compound. The onset of action and duration of action as well as the distribution in the body of a prodrug may differ from such properties of the parent compound. Also the resulting plasma concentration of the parent compound after administration of the prodrug may differ from the resulting plasma concentration after direct administration of the parent compound. For other types of prodrugs it should be realized that the hydroxyl group(s) in compounds according to Formula 1 can be placed in position by the metabolic system of the recipient. The hydroxyl group(s) contribute(s) significantly to the affinity for the estrogen receptor. Thus, compounds as defined by Formula 1, but lacking phenolic hydroxyl group(s) in the SERMF moiety are also made available as compounds according to this invention, and which compounds are referred to as prodrugs.

In one embodiment of the present invention, a phenolic hydroxyl group attached to the SERMF fragment of Formula 1 or of other Formulae described hereinbelow, is substituted with a (C1-8)alkyl or a (C1-18)acyl group, e.g. methyl, ethyl, tert.-butyl, n-octyl, acyl, octanoyl, dodecanoyl and octadecanoyl. In another embodiment, the hydroxyl group is substituted with a (C1-C4)alkyl or a (C1-C8)acyl group, e.g. methyl, ethyl, tert.-butyl, acyl and octanoyl.

Prodrugs of N-substituted azetidine derivatives of Formula 1 or of other Formulae described hereinbelow, may be prepared to increase their aqueous solubility in order to facilitate pharmaceutical formulation and/or to improve bioavailability following various routes of administration (e.g. intestinal absorption after oral administration). Such solubilizing prodrugs are well known to those of skill in the art. Representative examples of this approach can be found in V. J. Stella and W. N.-A. Kwame, *Advanced Drug Delivery Reviews*, 59 (2007) 677-694.

The present invention also embraces isotopically-labelled derivatives of any of the compounds according to Formula 1 or to other Formulae described hereinbelow, which are identical to those recited herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl and $^{123}$I, respectively.

Certain isotopically-labelled derivatives of the compounds of Formula 1 (e.g. those labelled with $^3$H and $^{14}$C) or of other Formulae described hereinbelow, are useful in compound and/or substrate tissue distribution assays. Tritiated (i.e. $^3$H) and carbon-14 (i.e. $^{14}$C) isotopes are particularly preferred for their ease of preparation and detectability. Certain isotopically-labelled compounds of Formula 1 or of other Formulae described hereinbelow, can be useful for medical imaging purposes. E.g., those labelled with positron-emitting isotopes like $^{11}$C or $^{18}$F can be useful for application in Positron Emission Tomography (PET) and those labelled with gamma ray emitting isotopes like $^{123}$I can be useful for application in Single Photon Emission Computed Tomography (SPECT). Further, substitution with heavier isotopes such as deuterium (i.e. $^2$H) may afford certain therapeutic advantages resulting from greater metabolic stability (e.g. increased in vivo half-life or reduced dosage requirements) and hence may be preferred in some circumstances. Isotopically-labelled compounds of Formula 1 or of other Formulae described hereinbelow, in particular those containing isotopes with longer half lives (T1/2>1 day), can generally be prepared by following procedures analogous to those disclosed in the Schemes and/or in the Examples hereinbelow, by substituting an appropriate isotopically-labelled reagent for a non-isotopically labelled reagent.

Pharmaceutically acceptable salts are well known in the art. They may be obtained during the final isolation and purification of the compounds of the present invention, or separately by reacting the free base function with an organic acid such as for example ascorbic acid, citric acid, tartaric acid, lactic acid, maleic acid or suitable mineral acids such as hydrochloric acid, phosphoric acid, or sulfuric acid, or with malonic acid, fumaric acid, glycolic acid, succinic acid, propionic acid, acetic acid, methanesulfonic acid, and the like. Alternatively, the acid function of any of the compounds of the present invention can be reacted with an organic or a mineral base, like sodium hydroxide, potassium hydroxide or lithium hydroxide to give a pharmaceutically acceptable salt.

The N-substituted azetidine derivatives of the present invention are ERα antagonists. In certain embodiments, the compounds of the present invention are specifically useful for treating ER-positive breast cancer i.e. demonstrate very low efficacy in stimulating proliferation of ER-positive, tamoxifen-resistant breast cancer cells, are capable of inducing ER downregulation in ER-positive breast cancer cells, are orally bioavailable and can be dosed to a level sufficient to achieve good bioavailability and/or target exposure and optimal efficacy.

In the context of the present invention with SERM (Selective Estrogen Receptor Modulator) is meant a synthetic compound that binds to ERα and exerts estrogenic or anti-estrogenic activities in a tissue- or cell-specific manner. Typically, SERMs are compounds that in an in vitro bioassay with recombinant Chinese Hamster Ovary (CHO) cells stably co-transfected with the human estrogen receptor α (hERα), the rat oxytocin promoter (RO) and the luciferase reporter gene (LUC) as described in Example 11 hereinbelow, inhibit 17β-estradiol-induced transactivation with a pIC50>6 and a minimum antagonistic efficacy of 0.80 relative to the anti-estrogen ICI 164,384 and, using the same bioassay, demonstrate a maximal agonistic efficacy of 0.20.

Also, SERMs are capable of stimulating proliferation in ER-positive, tamoxifen-resistant MCF-7H breast cancer cells as described in Example 12 hereinbelow, with a pEC50>7 and an efficacy>0.10.

In the context of the present invention with SERD (Selective Estrogen Receptor Downregulator) is meant a synthetic compound that binds to the ERα, is capable of destabilizing or downregulating ERα and primarily exerts anti-estrogenic activities in tissues or cells. Typically, SERDs are compounds that in an in vitro bioassay with recombinant CHO cells stably co-transfected with hERα, the rat oxytocin promoter (RO) and the luciferase reporter gene (LUC) as described in Example 11 hereinbelow, inhibit 17β-estradiol-induced transactivation with a pIC50>6 and a minimum antagonistic efficacy of 0.80, and, using the same bioassay, demonstrate a maximal agonistic efficacy of 0.20 Also, SERDs generally do not stimulate proliferation in ER-positive, tamoxifen-resistant MCF-7H breast cancer cells as described in Example 12 hereinbelow, and will therefore show an efficacy equal to or <0.10. Additionally, SERDs show a minimum of 20% downregulation of ERα in a bioassay in T47D cells as described in Example 13 hereinbelow.

In one embodiment, the invention relates to compounds of Formula 1 wherein X is O, S or NR5. In another embodiment, X is O or S. In yet another embodiment, X is O.

In another embodiment, the invention relates to compounds of Formula 1 wherein R17, R18 and R19 are H, fluorine or (C1-3)alkyl. In another embodiment, R17, R18 and R19 are H, fluorine or methyl. In yet another embodiment, R17, R18 and R19 are H.

In one embodiment, the invention relates to compounds of Formula 1 wherein R1 is (C1-4)alkyl, (C3-6)cycloalkyl, (C3-6)heterocycloalkyl, (C2-6)alkenyl, (C1-2)-alkoxy(C2-4)alkyl, (C3-6)cycloalkyl(C1-3)alkyl, (C3-6)heterocycloalkyl(C1-3)alkyl, each independently optionally substituted with one or more fluorine.

In another embodiment, R1 is (C1-4)alkyl, (C3-6)cycloalkyl, (C3-6)heterocycloalkyl, (C2-6)alkenyl, (C1-2) alkoxy(C2-4)alkyl, (C3-6)cycloalkyl(C1-3)alkyl, each independently optionally substituted with one or more fluorine.

In another embodiment of the present invention, R1 is methyl, ethyl, n-propyl, iso-butyl, cyclopropyl, cyclobutyl, cyclopentyl, cyclopropylmethyl, cyclobutylmethyl, (3-tetrahydrofuranyl)methyl, 3-methoxypropyl, 3,3,3-trifluoropropyl, 3-fluoropropyl or 2-propenyl.

In one embodiment of the present invention, the N-substituted azetidine derivative is selected from the group consisting of compounds according to any one of Formulae 3A to 3BF Formulae 3

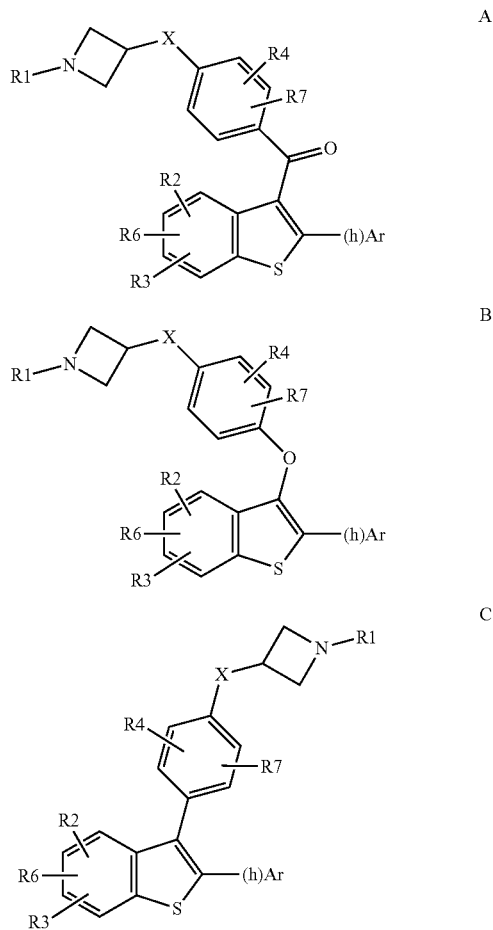

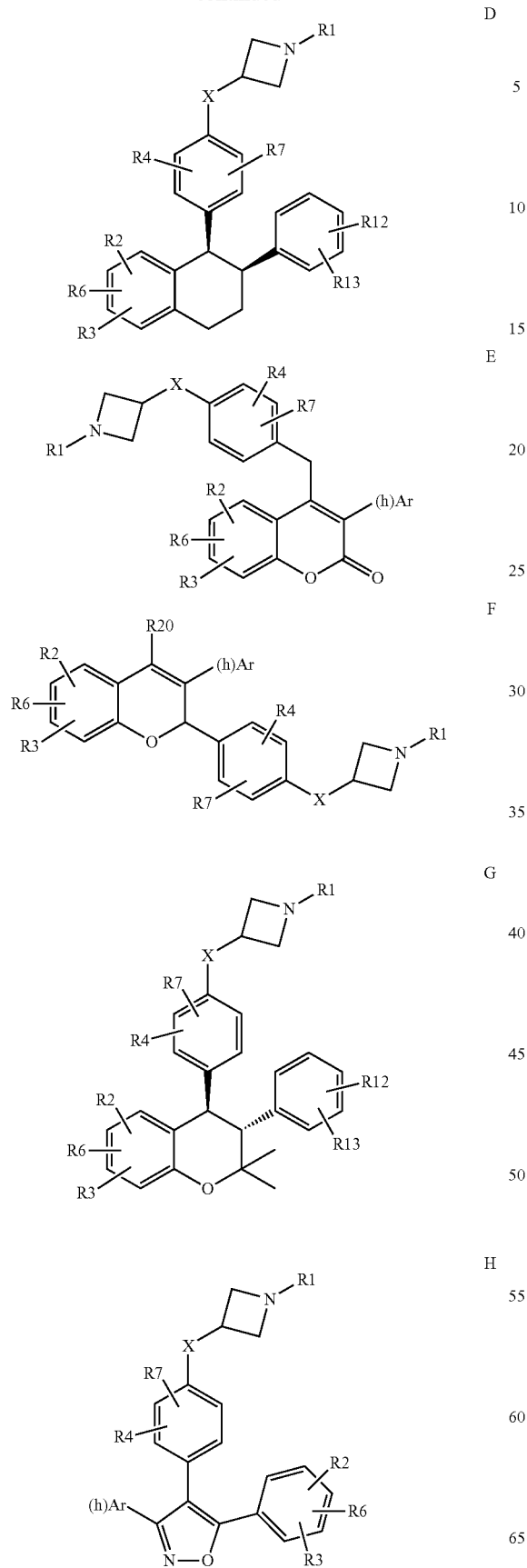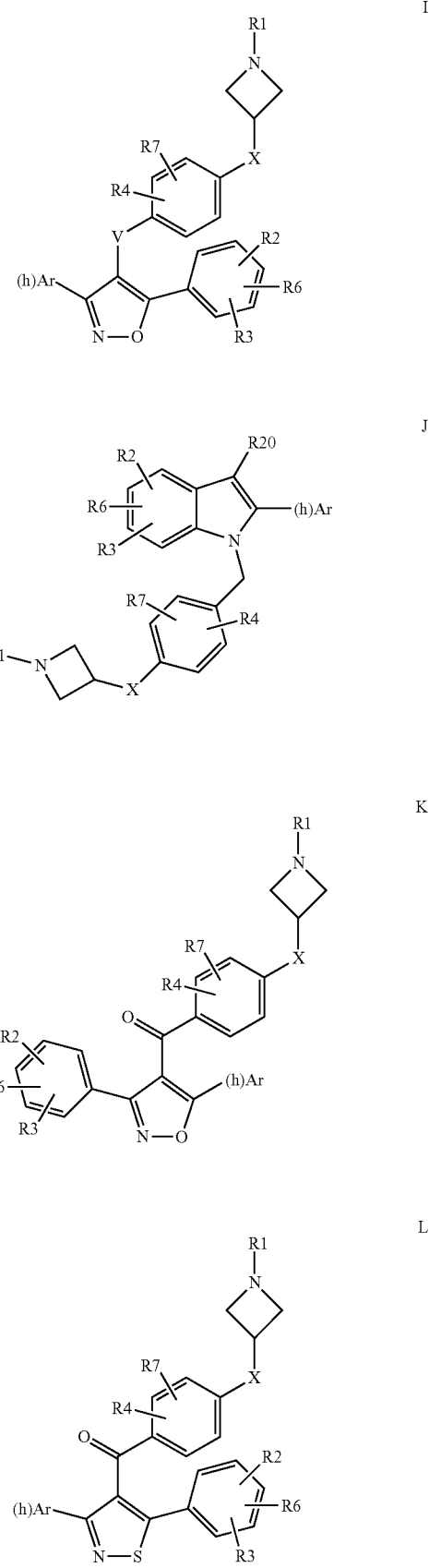

M
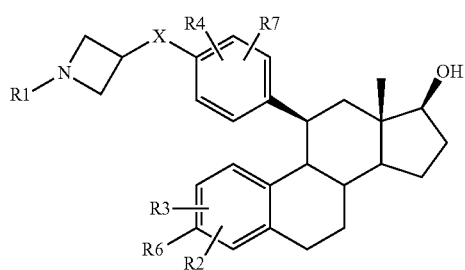
N
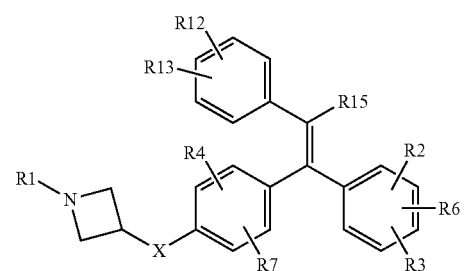
O
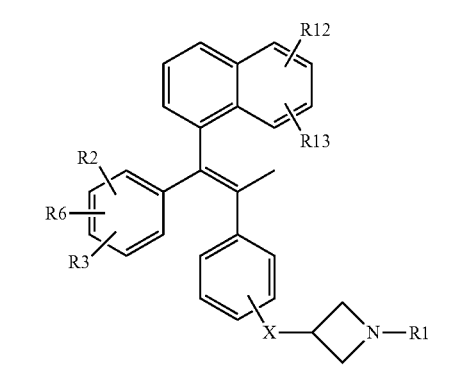
P
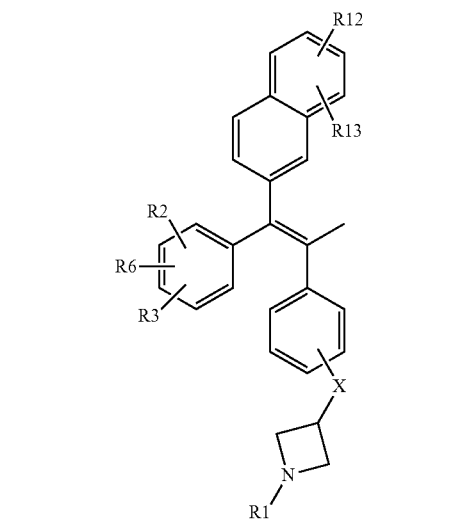
Q
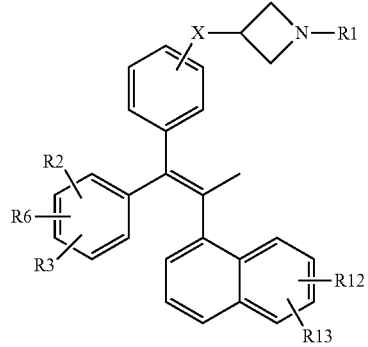
R
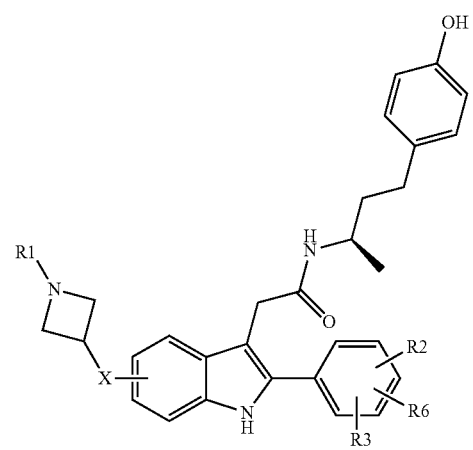
S
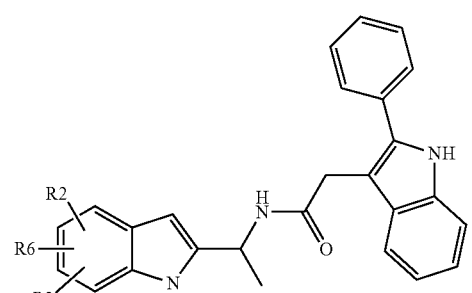
T
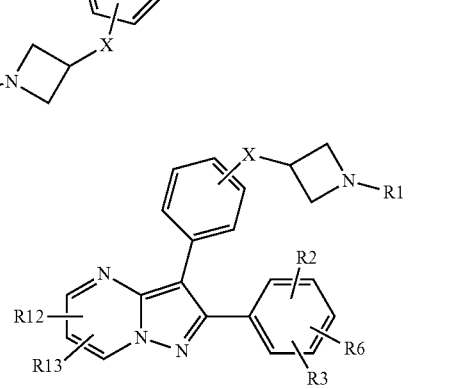

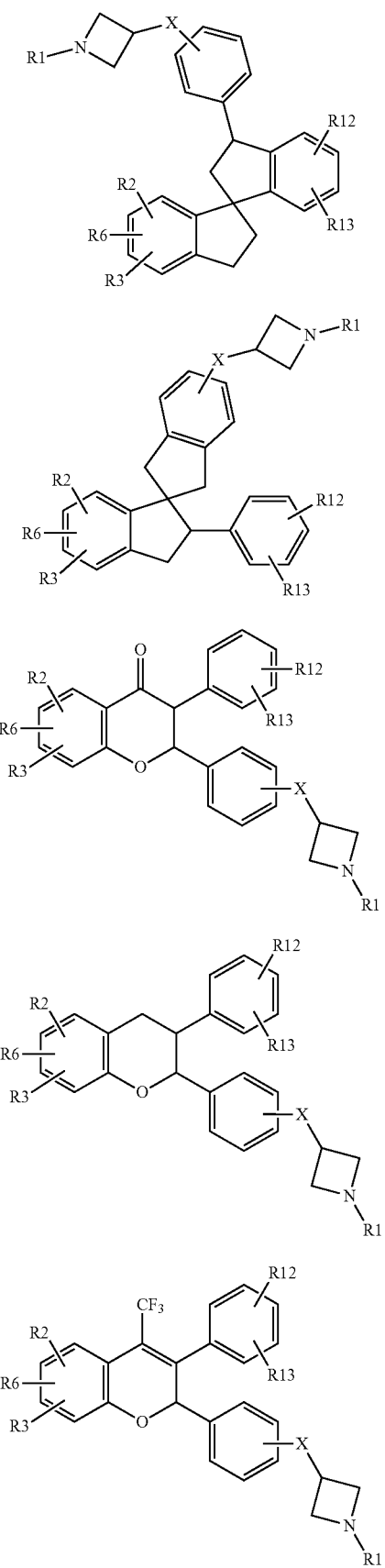
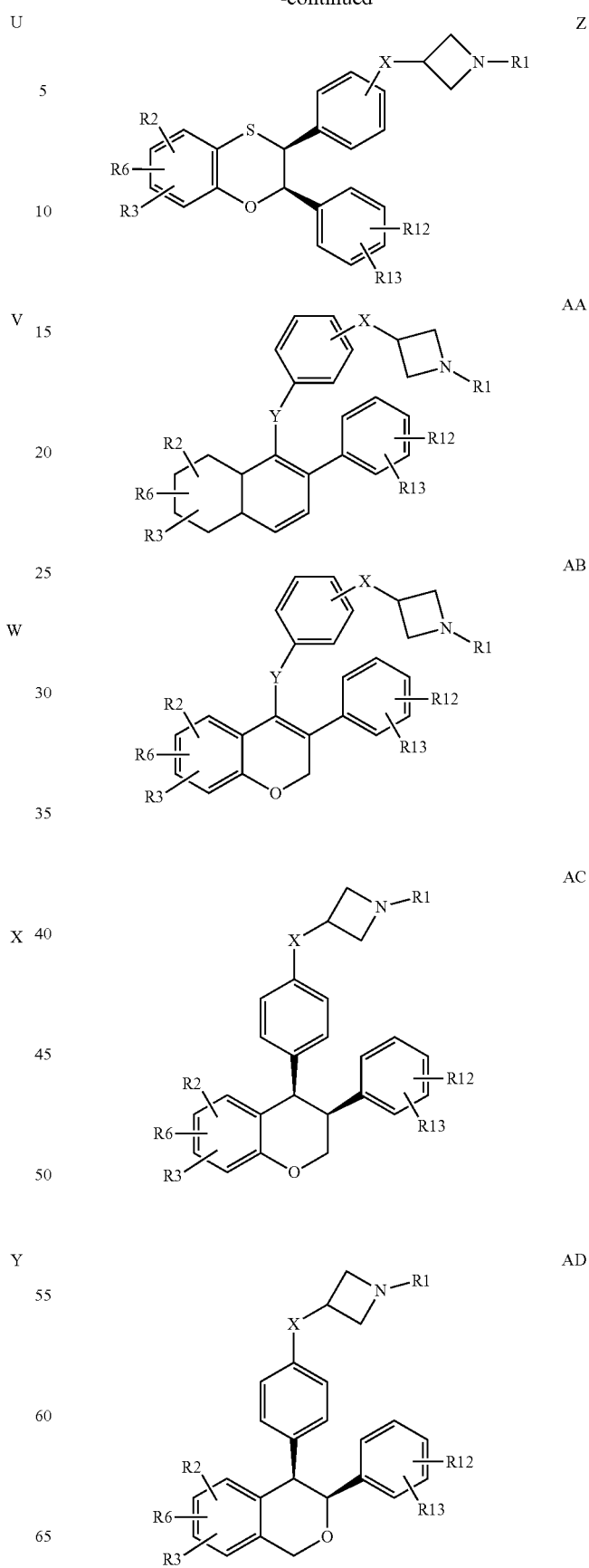

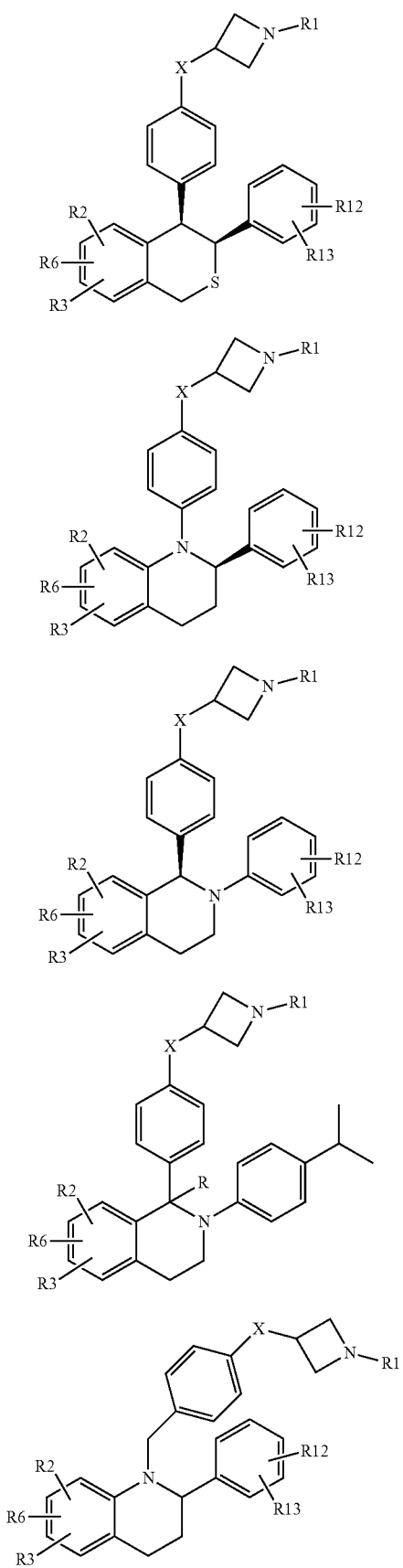
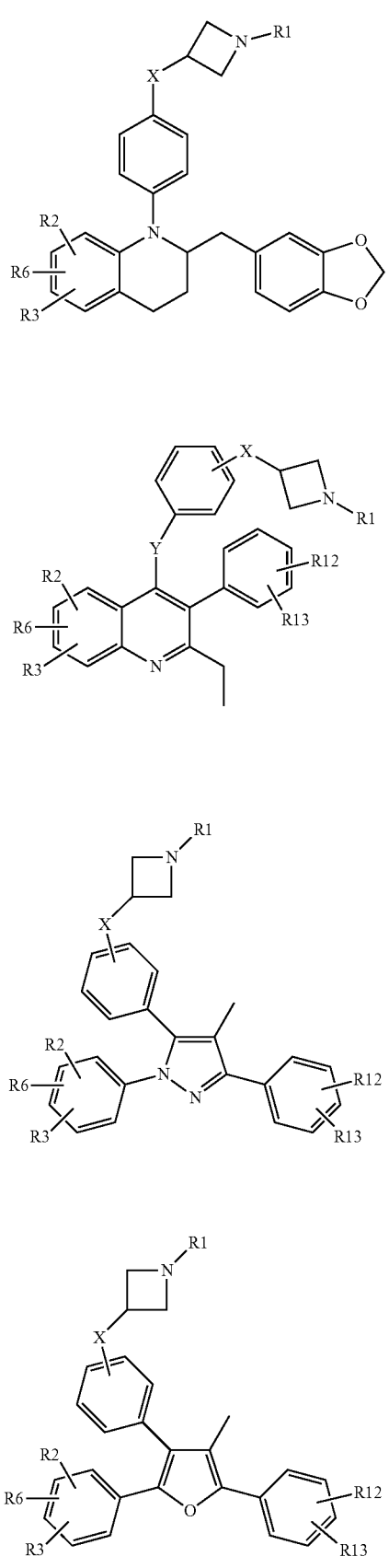

-continued
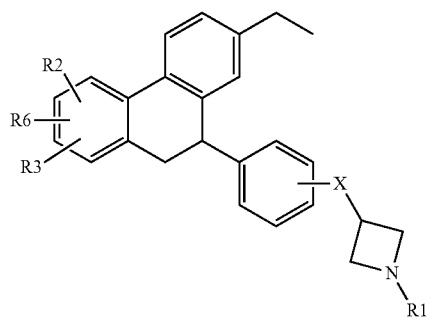
AN
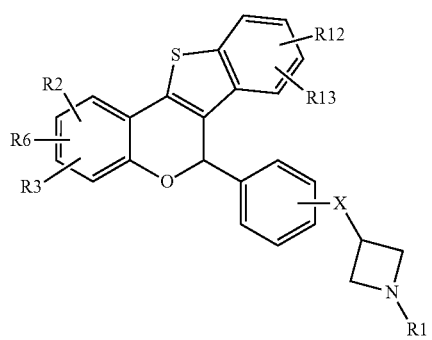
AO
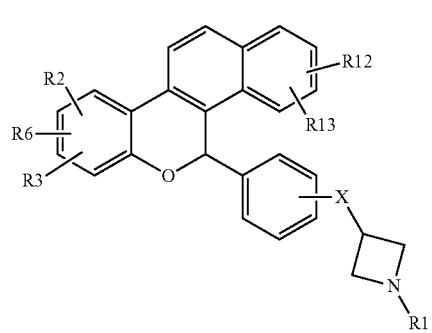
AP
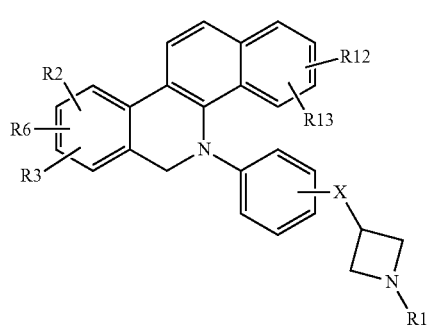
AQ
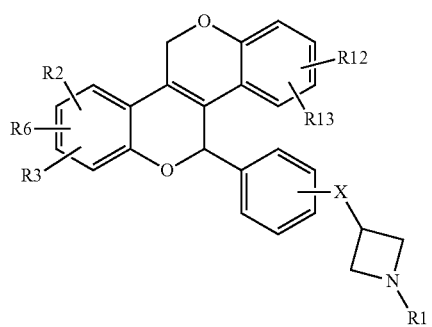
AR
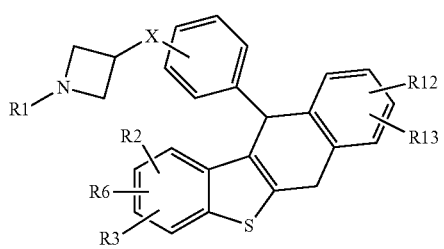
AS
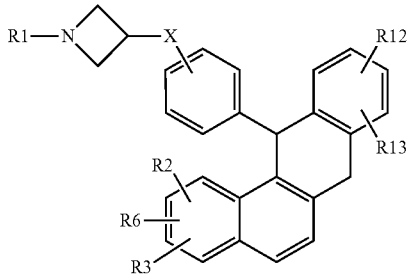
AT
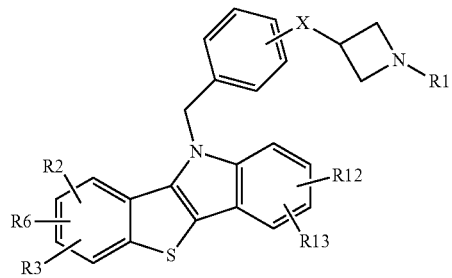
AU
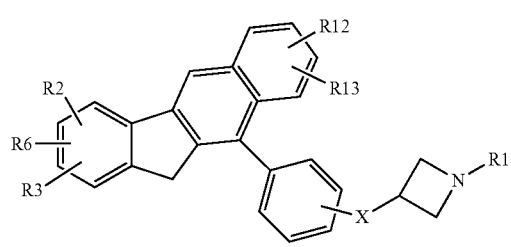
AV
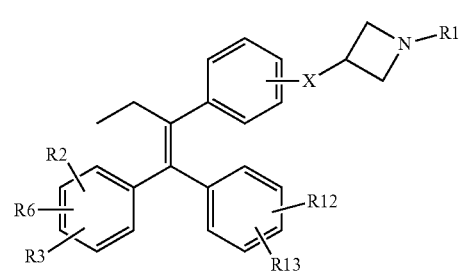
AW -continued AX 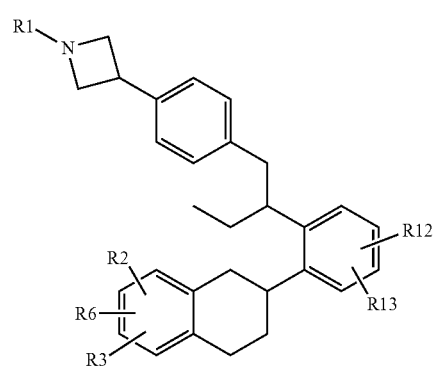

AY 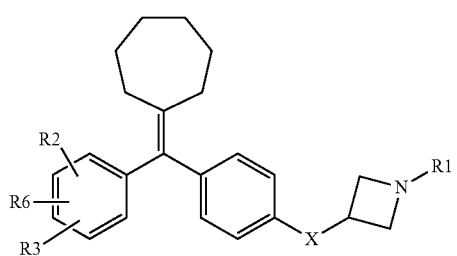

AZ 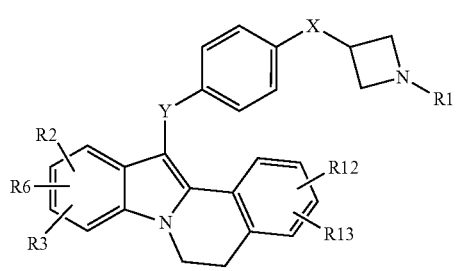

BA 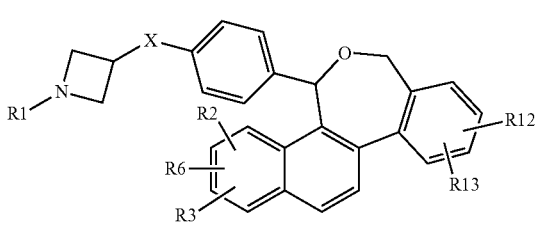

BB 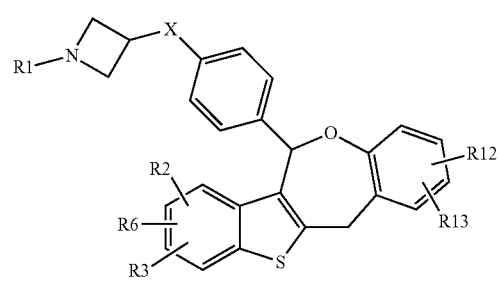

BC 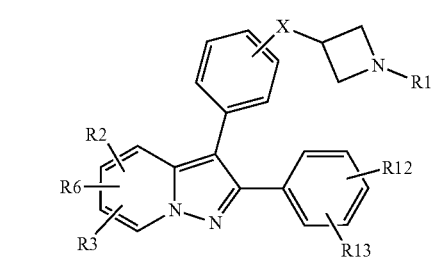

-continued

BD 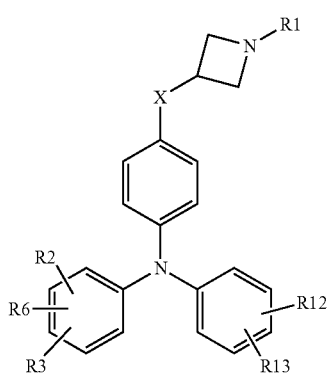

BE 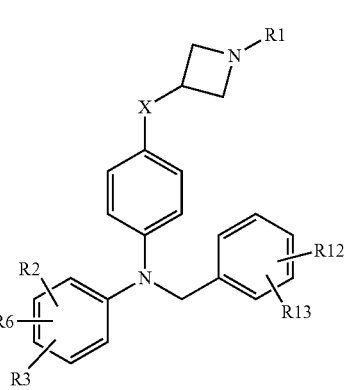

BF 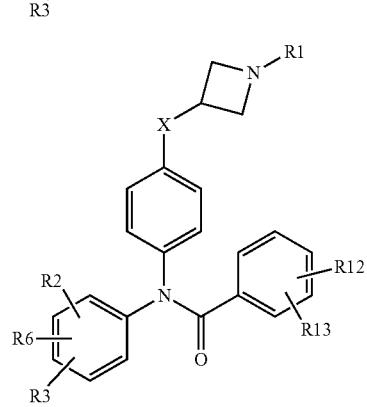

wherein

R1 is (C1-8)alkyl, (C3-8)cycloalkyl, (C3-6)heterocycloalkyl, (C2-6)alkenyl, (C2-6)-alkynyl, (C1-4)alkylcarbonyl, (C1-4)alkoxy(C2-4)alkyl, (C3-6)cycloalkyl(C1-3)alkyl, (C3-6)heterocycloalkyl(C1-3)alkyl, each independently optionally substituted with one or more halogen, nitrile, hydroxyl or (C1-2)alkyl;

X is no atom, O, S, CH$_2$, carbonyl, N—R5;

(h)Ar is a (hetero)aromatic ring, optionally substituted with R12 and R13;

R2 and R3 are independently of each other H, fluorine, chlorine, (C1-3)alkyl, (C1-3)alkoxy, (C1-3)alkylthio, CF$_3$ or nitrile;

R4 and R7 are independently of each other H, fluorine, chlorine, (C1-2)alkyl, CF$_3$ or nitrile;

R12 is H, fluorine, chlorine, (C1-2)alkyl, (C1-2)alkoxy, nitrile or hydroxyl;

R13 is H, fluorine, chlorine, (C1-3)alkyl, (C1-3)alkoxy, (C1-3)alkylthio, CF$_3$ or nitrile;

R6 is H, hydroxyl, amine or (C1-6)alkoxy;

R6 and R2 may be linked to form a (hetero)aromatic ring which is optionally substituted with fluorine, chlorine or (C1-3)alkyl;

R5 is H, (C1-3)alkyl, optionally substituted with one or more fluorine;

V is O, S, CH$_2$, CHOH, CH(C1-3)alkoxy, C=CH$_2$, carbonyl, N—R16;

R15 is H, halogen, nitro, nitrile or (C1-6)alkyl, optionally substituted with one or more halogen;

R16 is H, (C1-4)alkyl, (C1-4)alkenyl, optionally substituted with one or more halogen;

R20 is (C1-3)alkyl, optionally substituted with one or more fluorine.

In another embodiment of the present invention, the N-substituted azetidine derivative is selected from the group consisting of compounds according to any one of Formulae 4A to 4N and 4Z, shown hereinbelow, wherein R1 is (C1-8)alkyl, (C3-8)cycloalkyl, (C3-6)heterocycloalkyl, (C2-6)alkenyl, (C2-6)-alkynyl, (C1-4)alkylcarbonyl, (C1-4)alkoxy(C2-4)alkyl, (C3-6)cycloalkyl(C1-3)alkyl, (C3-6)heterocycloalkyl(C1-3)alkyl, each independently optionally substituted with one or more halogen, nitrile, hydroxyl or (C1-2)alkyl;

X is no atom, O, S, CH$_2$, carbonyl, N—R5;

(h)Ar is a (hetero)aromatic ring, optionally substituted with R12 and R13;

R2 and R3 are independently of each other H, fluorine, chlorine, (C1-3)alkyl, (C1-3)alkoxy, (C1-3)alkylthio, CF$_3$ or nitrile;

R4 and R7 are independently of each other H, fluorine, chlorine, (C1-2)alkyl, CF$_3$ or nitrile;

R12 is H, fluorine, chlorine, (C1-2)alkyl, (C1-2)alkoxy, nitrile or hydroxyl;

R13 is H, fluorine, chlorine, (C1-3)alkyl, (C1-3)alkoxy, (C1-3)alkylthio, CF$_3$ or nitrile;

R6 is H, hydroxyl, amine or (C1-6)alkoxy;

R6 and R2 may be linked to form a (hetero)aromatic ring which is optionally substituted with fluorine, chlorine or (C1-3)alkyl;

R5 is H, (C1-3)alkyl, optionally substituted with one or more fluorine;

V is O, S, CH$_2$, CHOH, CH(C1-3)alkoxy, C=CH$_2$, carbonyl, N—R16;

Formulae 4

A

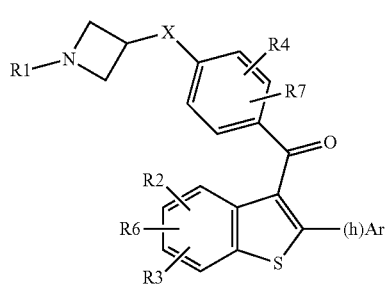

B

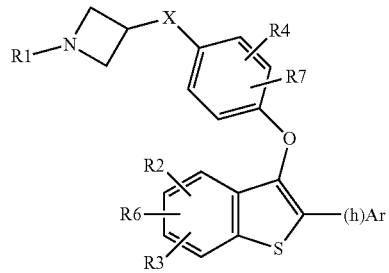

C

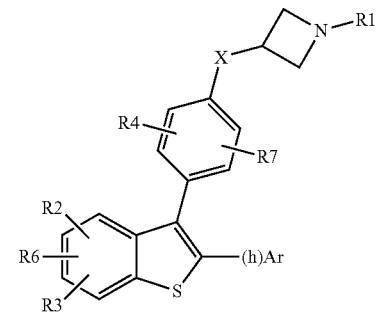

D

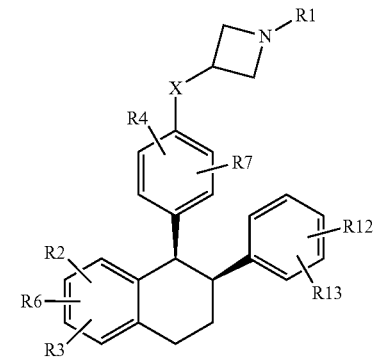

E

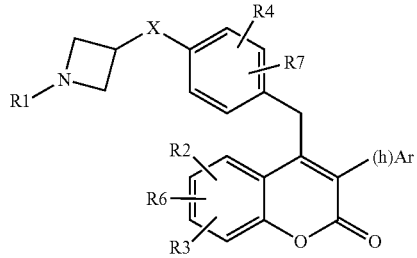

F

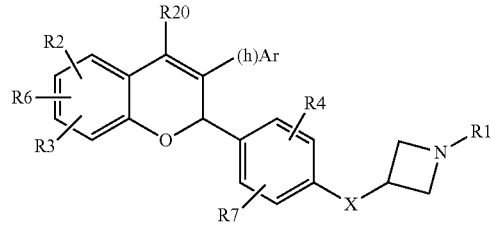

-continued
G
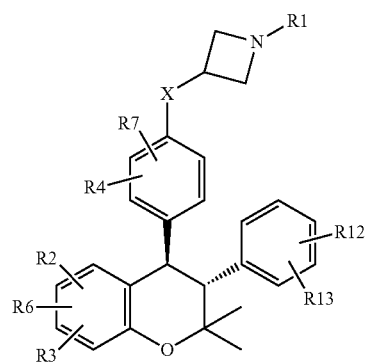
H
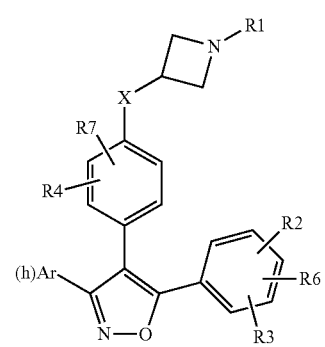
I
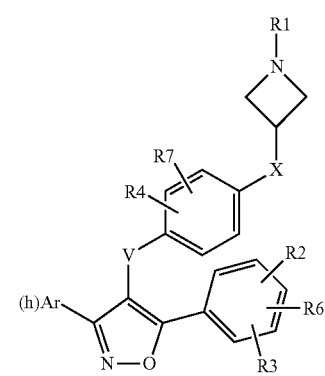
J
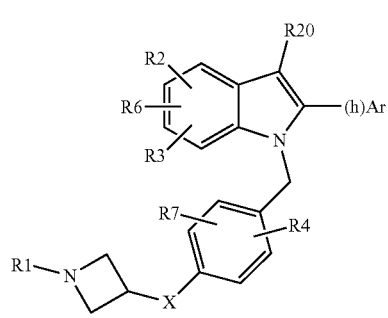
-continued
K
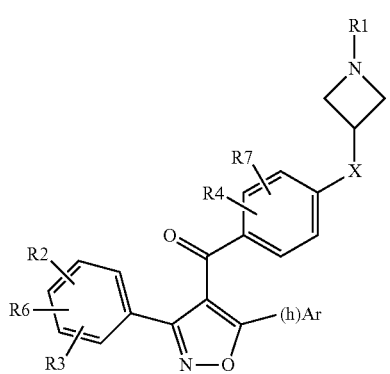
L
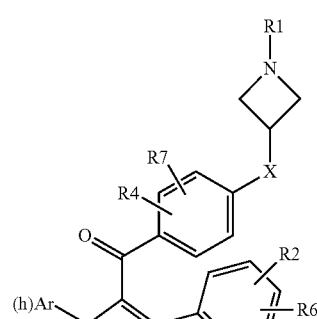
M
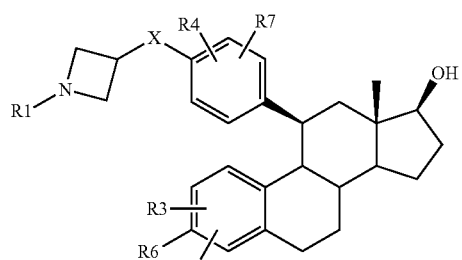
N
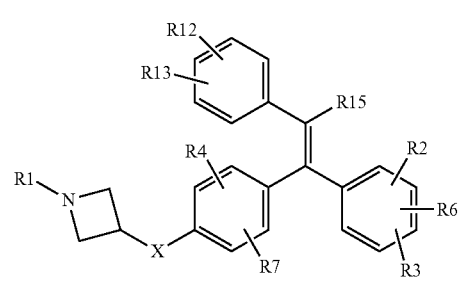
Z
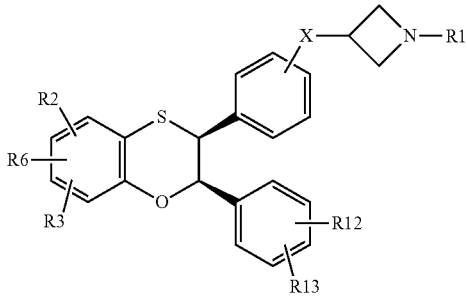
R15 is H, halogen, nitro, nitrile or (C1-6)alkyl, optionally substituted with one or more halogen;

R16 is H, (C1-4)alkyl, (C1-4)alkenyl, optionally substituted with one or more halogen;

R20 is (C1-3)alkyl, optionally substituted with one or more fluorine.

The term (h)Ar or (hetero)aromatic ring means an aromatic or heteroaromatic ring system, the aromatic skeleton of which containing five to ten atoms of which zero to four atoms other than carbon, selected from oxygen, nitrogen or sulfur. Examples are phenyl, naphthyl, pyridyl, thienyl, furanyl, thiazolyl, oxazolyl, pyrrolyl, thiadiazolyl, tetrazolyl, benzopyrrolyl and benzopyrrazolyl.

The term CH(C1-3)alkoxy means a methylene linker that is substituted with an alkoxy group containing 1-3 carbon atoms, being methoxymethylene, ethoxymethylene and propyloxymethylene.

In one embodiment, the present invention relates to compounds of Formulae 3 or 4 wherein R1 is (C1-4)alkyl, (C3-6)cycloalkyl, (C3-6)heterocycloalkyl, (C2-6)-alkenyl, (C1-2)alkoxy(C2-4)alkyl, (C3-6)cycloalkyl(C1-3)alkyl, (C3-6)heterocycloalkyl(C1-3)alkyl, each independently optionally substituted with one or more fluorine.

In another embodiment, R1 is (C1-4)alkyl, (C3-6)cycloalkyl, (C3-6)heterocycloalkyl, (C2-6)alkenyl, (C1-2) alkoxy(C2-4)alkyl, (C3-6)cycloalkyl(C1-3)alkyl, each independently optionally substituted with one or more fluorine.

In another embodiment of the present invention, R1 is methyl, ethyl, n-propyl, iso-butyl, cyclopropyl, cyclobutyl, cyclopentyl, cyclopropylmethyl, cyclobutylmethyl, (3-tetrahydrofuranyl)methyl, 3-methoxypropyl, 3,3,3-trifluoropropyl, 3-fluoropropyl or 2-propenyl.

In one embodiment, the present invention relates to compounds of Formulae 3 or 4 wherein X is O, S or N—R5. In another embodiment, X is O or S. In yet another embodiment, X is O.

In another embodiment, the invention relates to compounds of Formulae 3 or 4 wherein R2 and R3 are independently of each other H, fluorine, chlorine, (C1-2)-alkyl, CF$_3$ or nitrile. In yet another embodiment, R2 and R3 are independently of each other H, fluorine, chlorine or (C1-2) alkyl.

In another embodiment, the invention relates to compounds of Formulae 3 or 4 wherein R4 and R7 are independently of each other H, fluorine, chlorine or (C1-2)-alkyl. In yet another embodiment, R4 and R7 are independently of each other H or fluorine.

In another embodiment, the invention relates to compounds of Formulae 3 or 4 wherein R5 is H or methyl.

In another embodiment, the invention relates to compounds of Formulae 3 or 4 wherein R6 is H, hydroxyl or (C1-2)alkoxy or wherein R6 is, together with R2, part of a (hetero)aromatic ring. In yet another embodiment, R6 is H, hydroxyl or (C1-2)-alkoxy.

In another embodiment, the invention relates to compounds of Formulae 3 or 4 wherein R12 is H, fluorine, chlorine, (C1-2)alkyl, nitrile or hydroxyl.

In another embodiment, the invention relates to compounds of Formulae 3 or 4 wherein R13 is H, fluorine, chlorine, (C1-2)alkyl, (C1-2)alkoxy, CF$_3$ or nitrile. In yet another embodiment, R13 is H, fluorine, chlorine or (C1-2) alkyl.

In another embodiment, the invention relates to compounds of Formulae 3 or 4 wherein R15 is H, chlorine, nitrile or (C1-4)alkyl, optionally substituted with one or more halogen. In yet another embodiment, R15 is H, chlorine or (C1-3)alkyl, optionally substituted with one or more fluorine or chlorine.

In another embodiment, the invention relates to compounds of Formulae 4 wherein V is O, CH$_2$, CHOH, CH(C1-2)alkoxy, C=CH$_2$ or carbonyl.

In another embodiment, the invention relates to compounds of Formulae 4 wherein R16 is H, (C1-3)alkyl, optionally substituted with one or more halogen. In yet another embodiment, R16 is H or methyl.

In one embodiment, the present invention relates to compounds of Formulae 4 wherein R20 is methyl or CF$_3$.

In yet another embodiment of the present invention, the N-substituted azetidine derivative is selected from the group consisting of compounds according to any one of Formulae 5A to 5T, shown hereinbelow, wherein R1 is (C1-8)alkyl, (C3-8)cycloalkyl, (C3-6)heterocycloalkyl, (C2-6)alkenyl, (C2-6)-alkynyl, (C1-4)alkylcarbonyl, (C1-4)alkoxy(C2-4)alkyl, (C3-6)cycloalkyl(C1-3)alkyl, (C3-6)heterocycloalkyl(C1-3)alkyl, each independently optionally substituted with one or more halogen, nitrile, hydroxyl or (C1-2)alkyl;

(h)Ar is a (hetero)aromatic ring, optionally substituted with R12 and R13;

R2 and R3 are independently of each other H, fluorine, chlorine, (C1-3)alkyl, (C1-3)alkoxy, (C1-3)alkylthio, CF$_3$ or nitrile;

R4 and R7 are independently of each other H, fluorine, chlorine, (C1-2)alkyl, CF$_3$ or nitrile;

R12 is H, fluorine, chlorine, (C1-2)alkyl, (C1-2)alkoxy, nitrile or hydroxyl;

R13 is H, fluorine, chlorine, (C1-3)alkyl, (C1-3)alkoxy, (C1-3)alkylthio, CF$_3$ or nitrile;

R6 is H, hydroxyl, amine or (C1-6)alkoxy;

R6 and R2 may be linked to form a (hetero)aromatic ring which is optionally substituted with fluorine, chlorine or (C1-3)alkyl.

Formulae 5

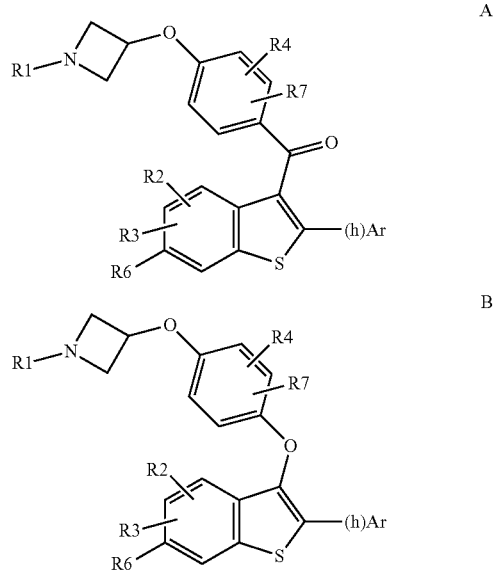

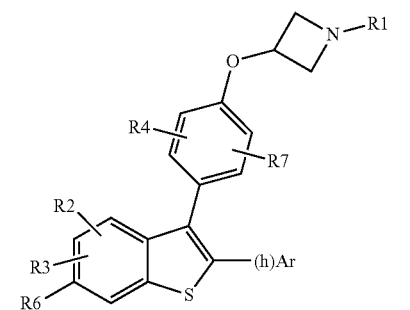
C
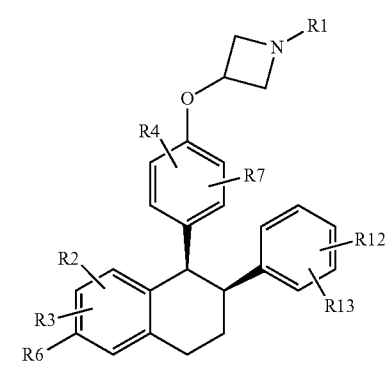
D
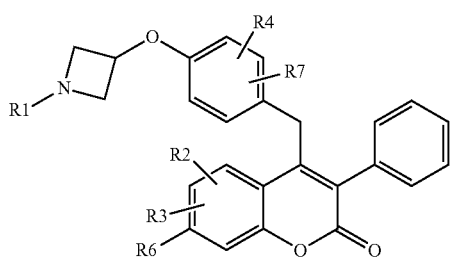
E
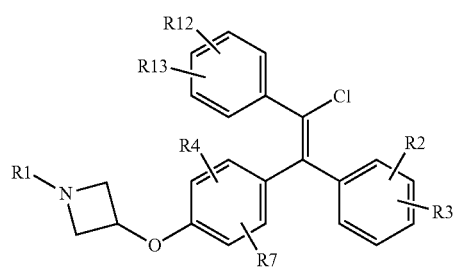
F
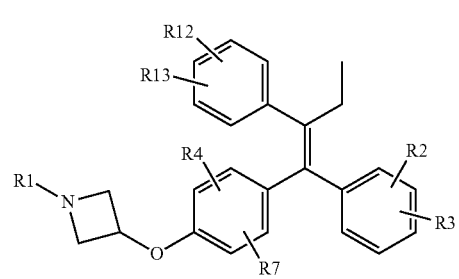
G
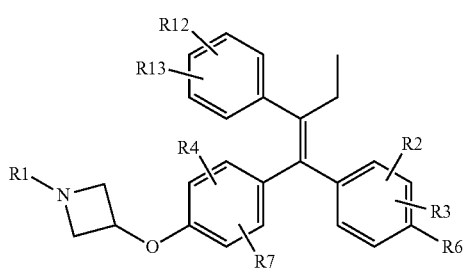
H
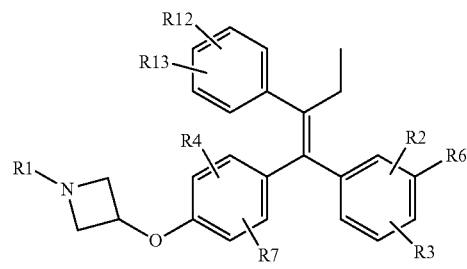
I
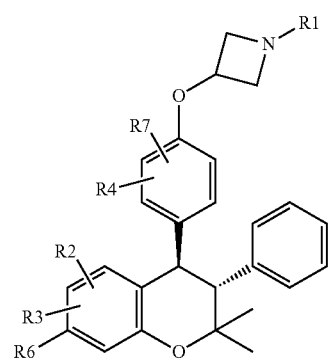
J
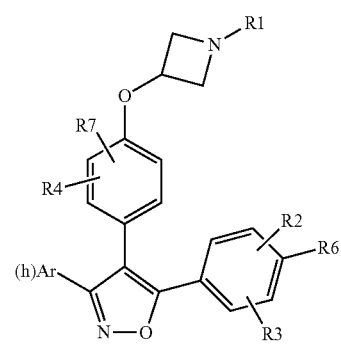
K
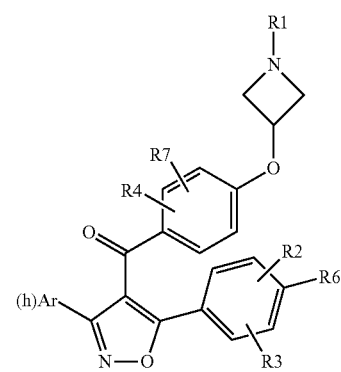
L -continued

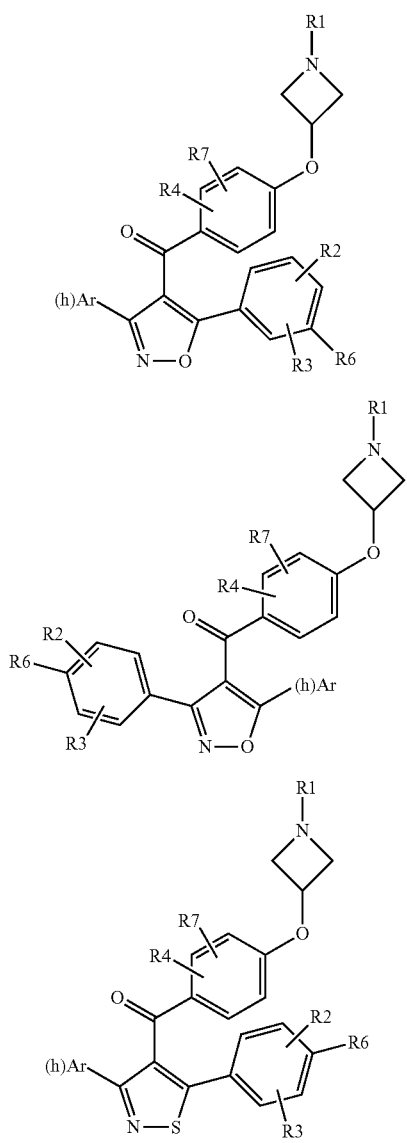

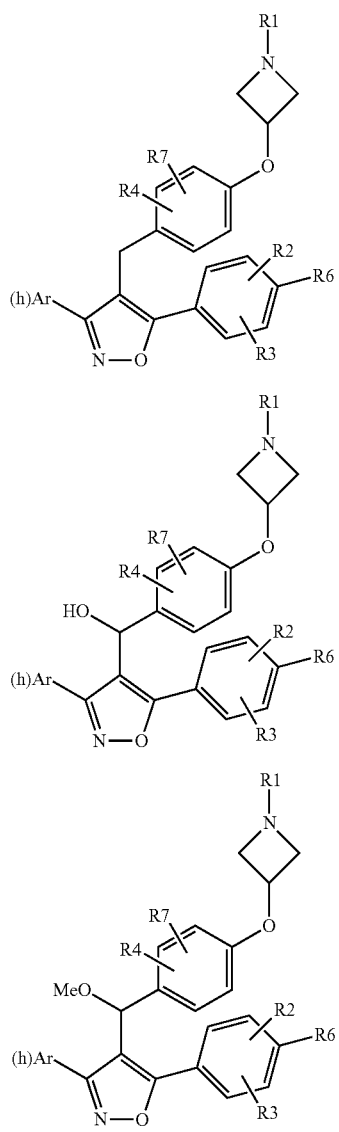

In one embodiment the present invention relates to compounds of Formulae 5 wherein R1 is (C1-4)alkyl, (C3-6)cycloalkyl, (C3-6)heterocycloalkyl, (C2-6)alkenyl, (C1-2)alkoxy(C2-4)alkyl, (C3-6)cycloalkyl(C1-3)alkyl, (C3-6)heterocycloalkyl(C1-3)alkyl, each independently optionally substituted with one or more fluorine.

Formulae 5

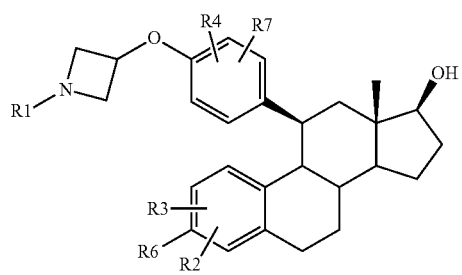

In another embodiment, R1 is methyl, ethyl, n-propyl, iso-butyl, cyclopropyl, cyclobutyl, cyclopentyl, cyclopropylmethyl, cyclobutylmethyl, (3-tetrahydrofuranyl)-methyl, 3-methoxypropyl, 3,3,3-trifluoropropyl, 3-fluoropropyl or 2-propenyl.

In another embodiment, the invention relates to compounds of Formulae 5 wherein R2 and R3 are independently of each other H, fluorine, chlorine, (C1-2)alkyl, CF$_3$ or nitrile. In yet another embodiment, R2 and R3 are independently of each other H, fluorine, chlorine or (C1-2)alkyl.

In another embodiment, the invention relates to compounds of Formulae 5 wherein R4 and R7 are independently of each other H, fluorine, chlorine or (C1-2)alkyl. In yet another embodiment, R4 and R7 are independently of each other H or fluorine.

In another embodiment, the invention relates to compounds of Formulae 5 wherein R6 is H, hydroxyl or (C1-2)alkoxy or wherein R6 is, together with R2, part of a (hetero)aromatic ring. In yet another embodiment, R6 is H, hydroxyl or (C1-2)-alkoxy.

In another embodiment, the invention relates to compounds of Formulae 5 wherein R12 is H, fluorine, chlorine, (C1-2)alkyl, nitrile or hydroxyl.

In another embodiment, the invention relates to compounds of Formulae 5 wherein R13 is H, fluorine, chlorine, (C1-2)alkyl, (C1-2)alkoxy, CF$_3$ or nitrile. In yet another embodiment, R13 is H, fluorine, chlorine or (C1-2)alkyl.

In one embodiment of the present invention, the N-substituted azetidine derivative is selected from the group consisting of compounds according to any one of Formulae 6a-6x, shown hereinbelow.

The N-substituted azetidine derivatives of Formulae 6 are ERα antagonists with pIC50>7 as defined hereinabove (see also Table 3 hereinbelow).

Formulae 6

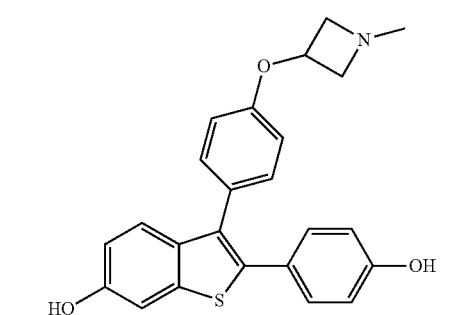
6a

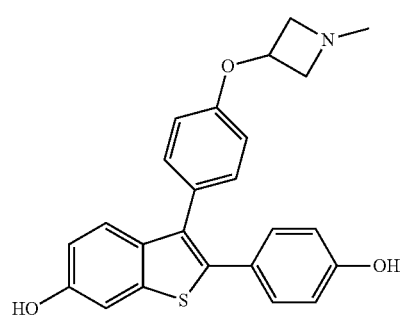
6b

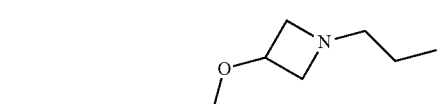
6c

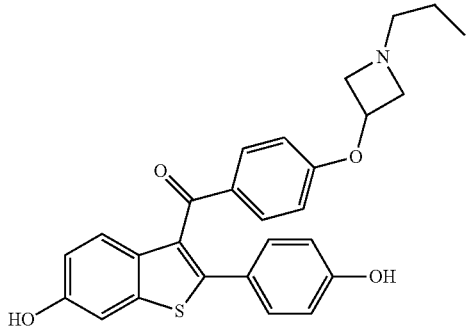
6d

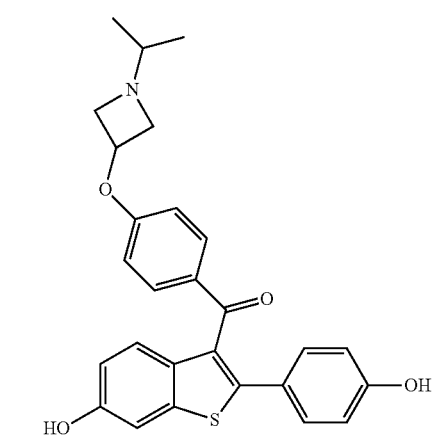
6e

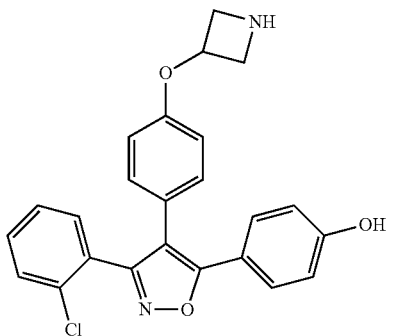
6f

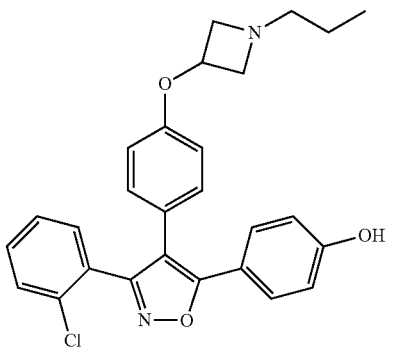
6g

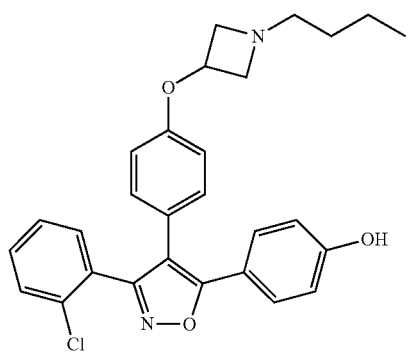
6h
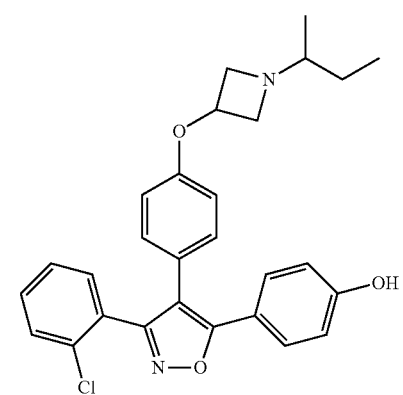
6i
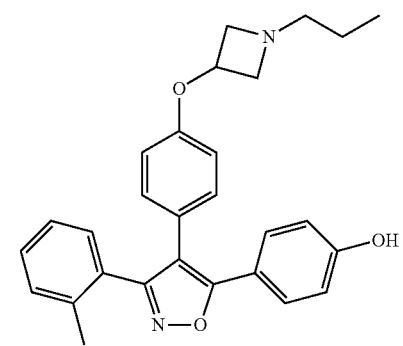
6j
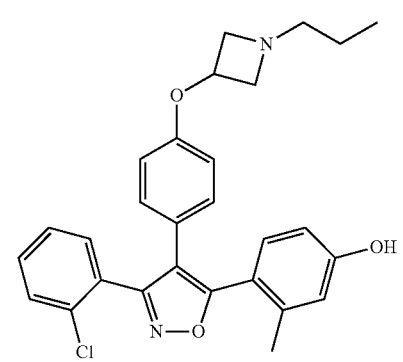
6k
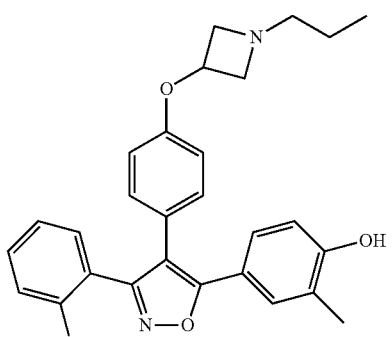
6l
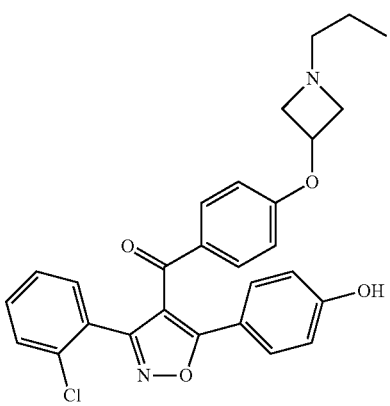
6m
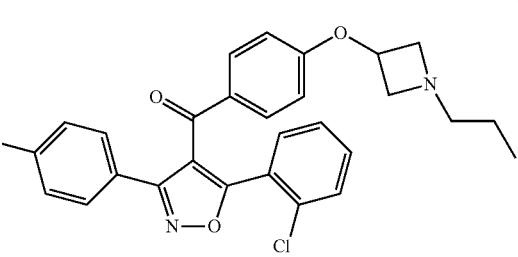
6n
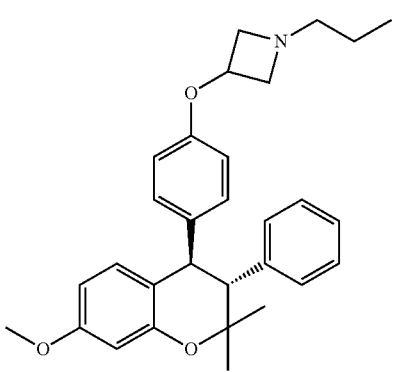
6o

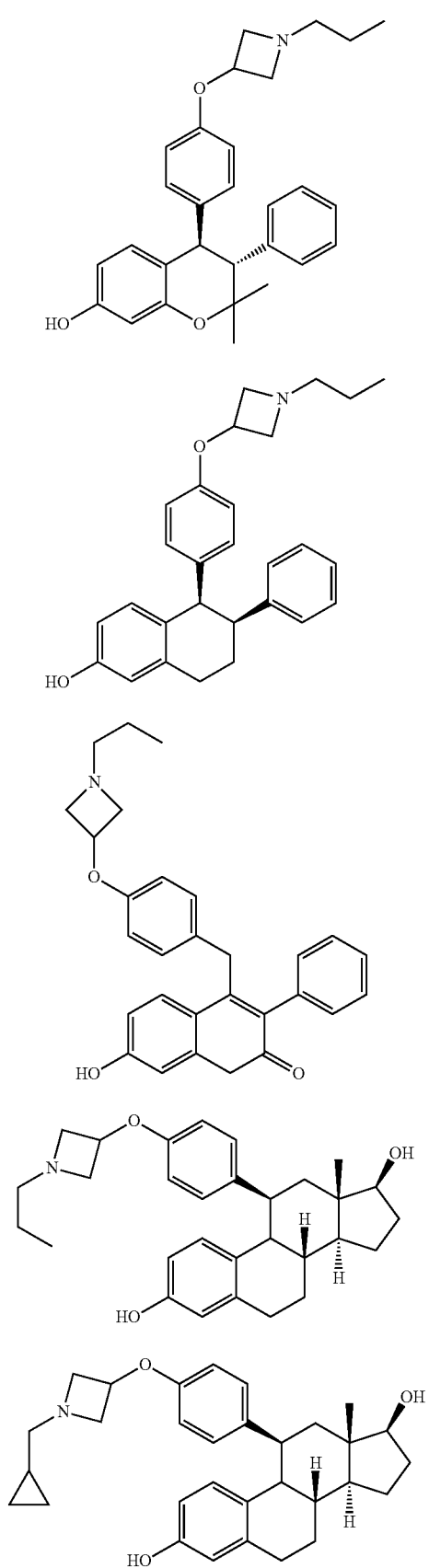
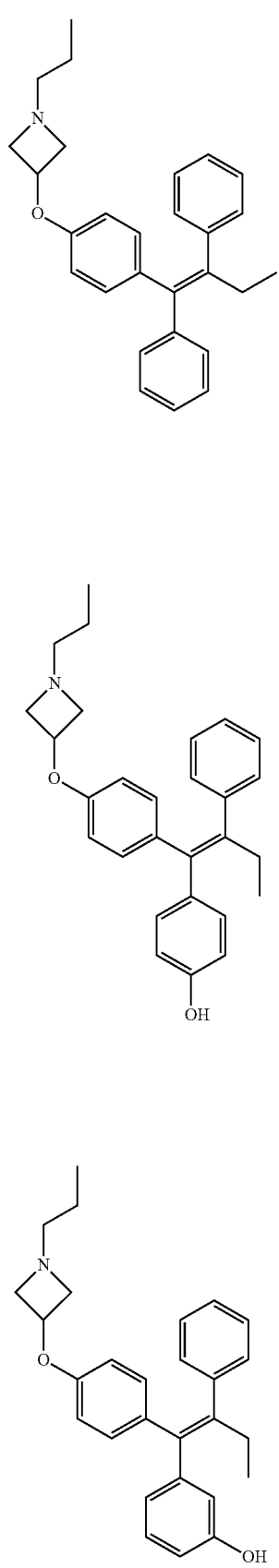

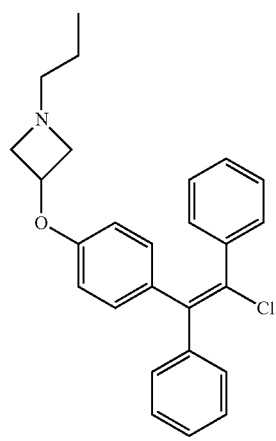
6x
In another embodiment of the present invention, the N-substituted azetidine derivative is selected from the group consisting of compounds according to any one of Formulae 7a-7bj
Formulae 7
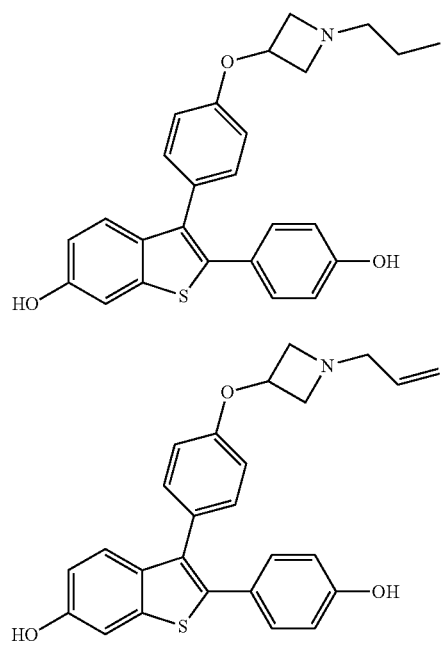
7a
7b
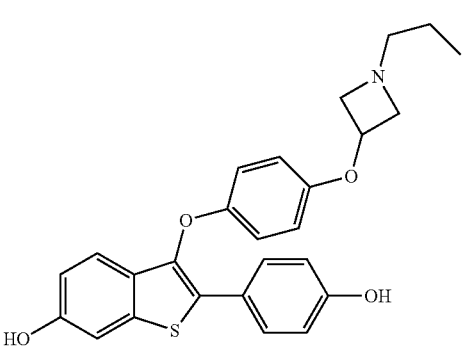
7c
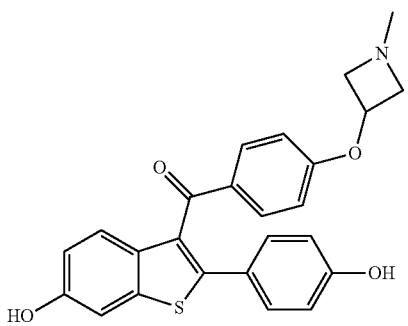
7d
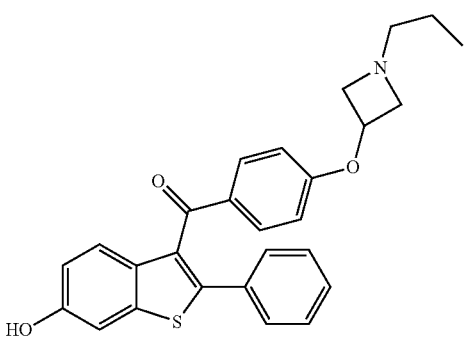
7e
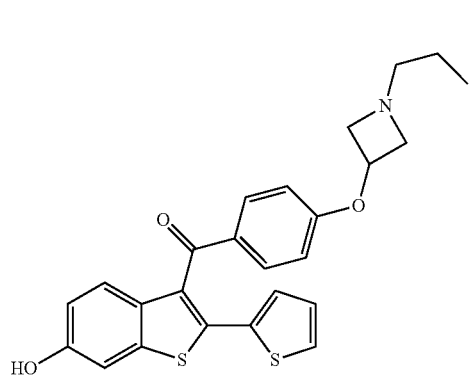
7f
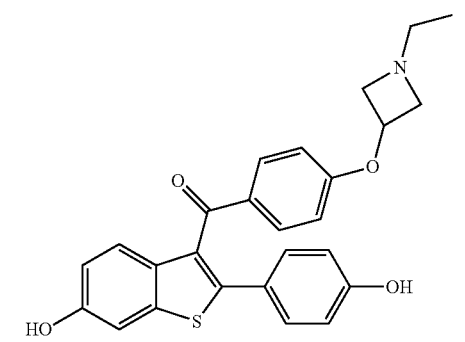
7g

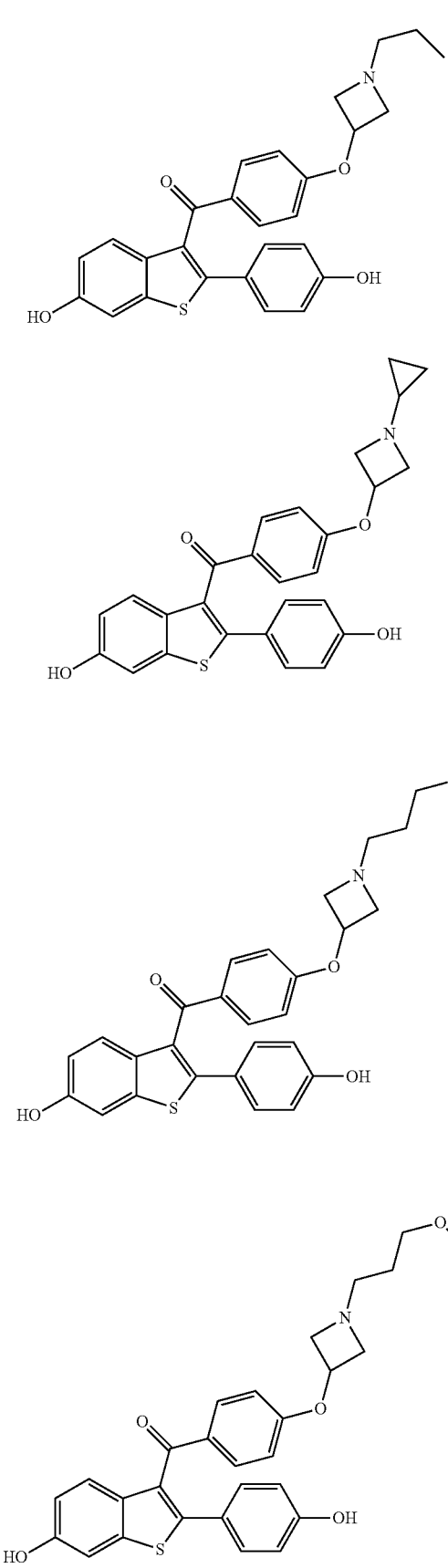
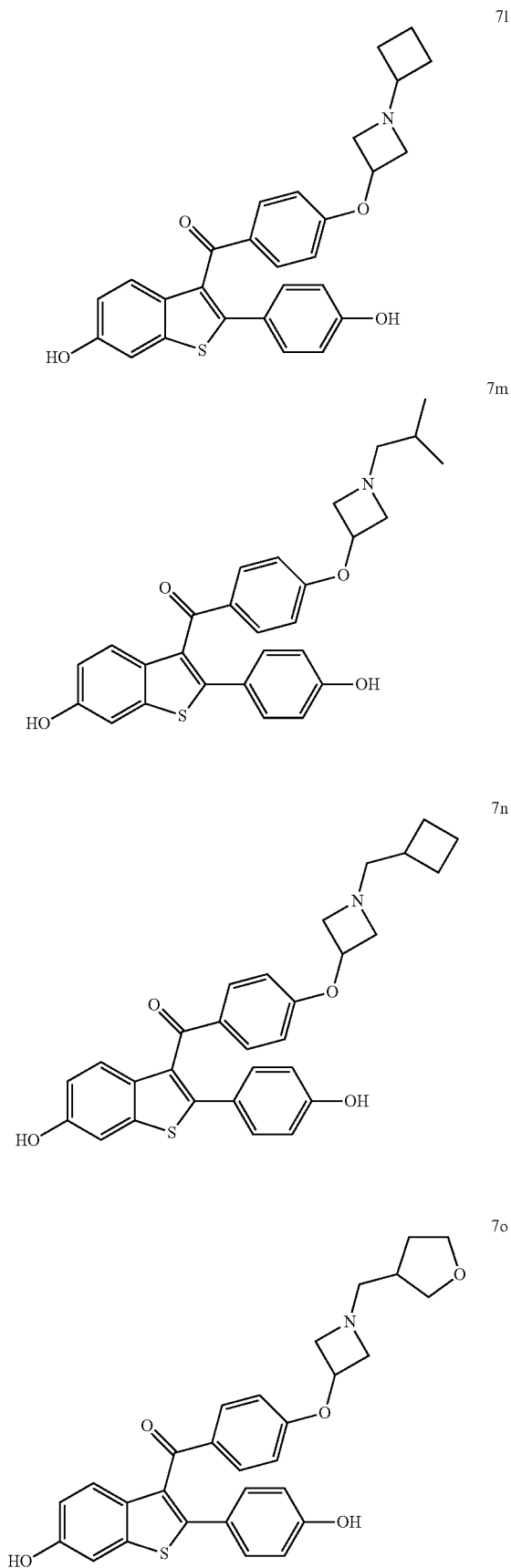

-continued
7p
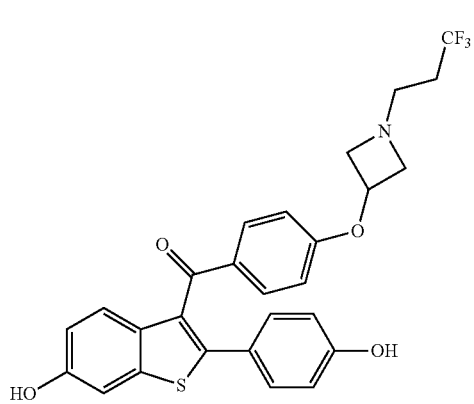
7q
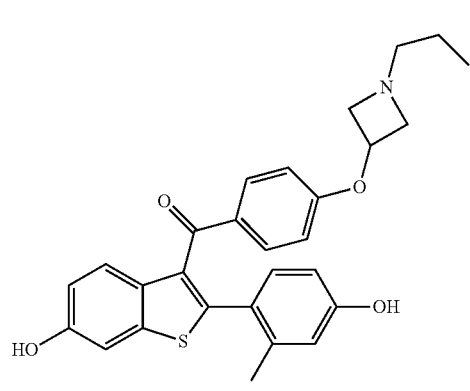
7r
7s
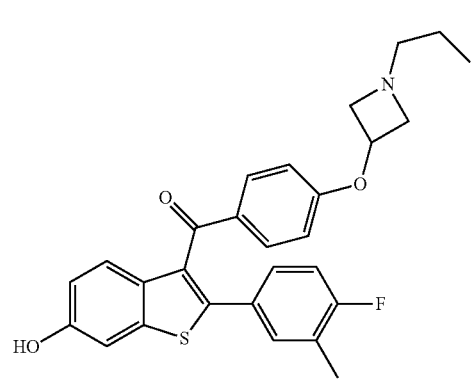
-continued
7t
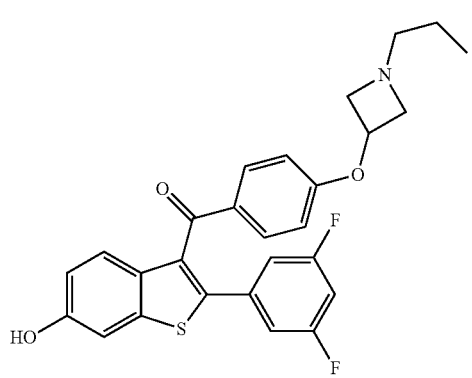
7u
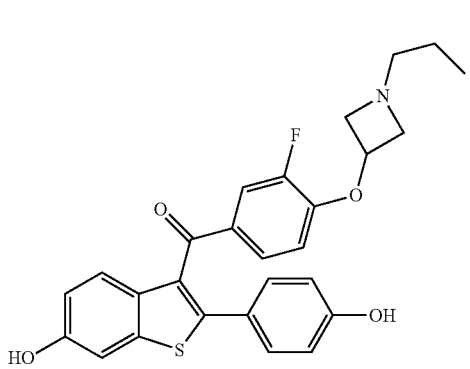
7v
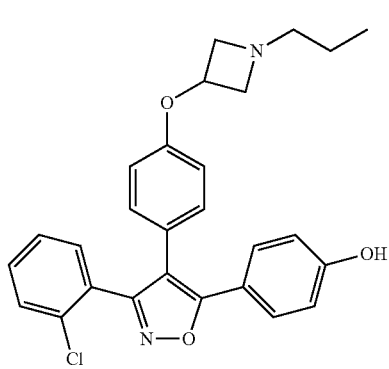
7w
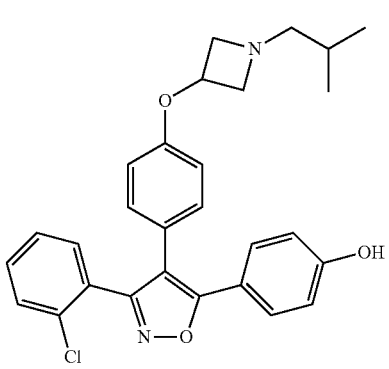

-continued
| | |
|---|---|
| 7x 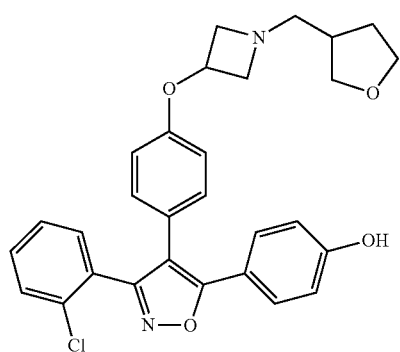 | 7ab 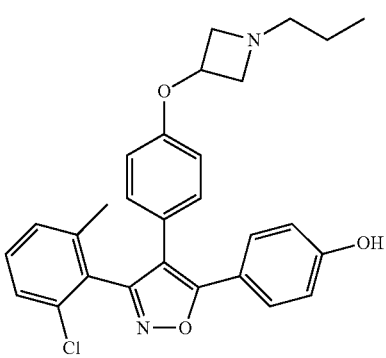 |
| 7y 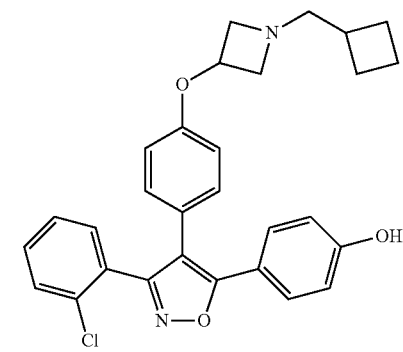 | 7ac 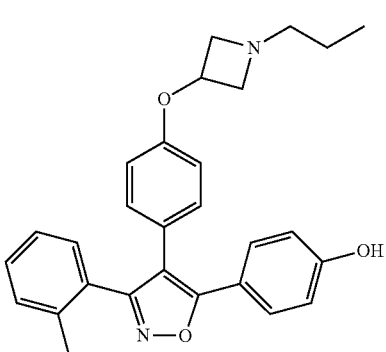 |
| 7z 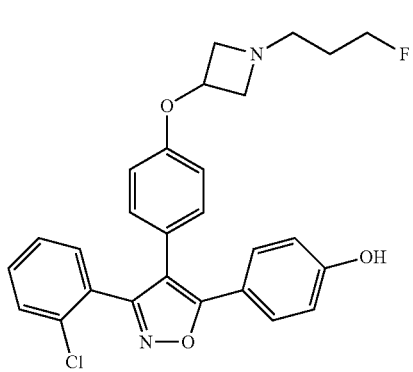 | 7ad 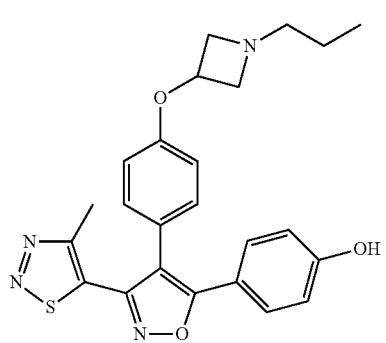 |
| 7aa | 7ae |

-continued
7af
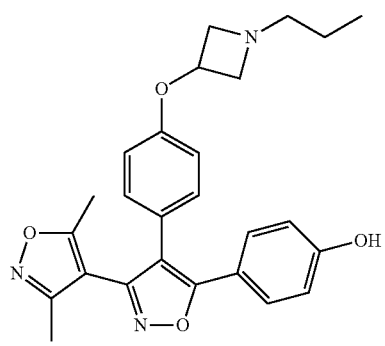
7ag
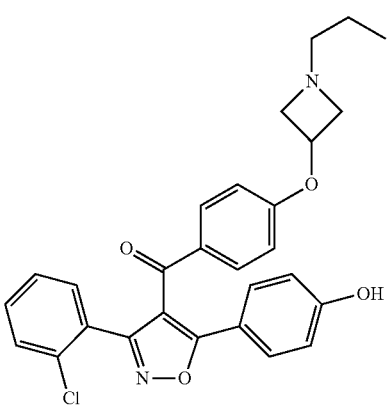
7ah
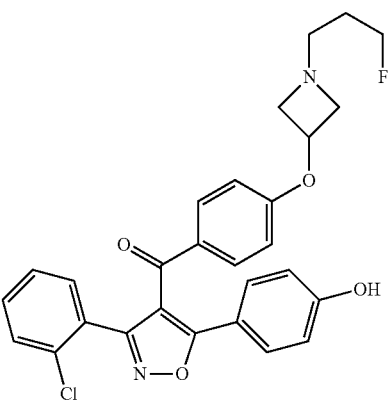
7ai
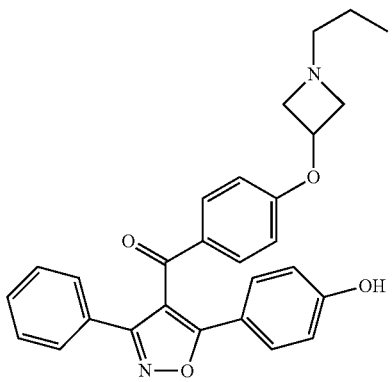
-continued
7aj
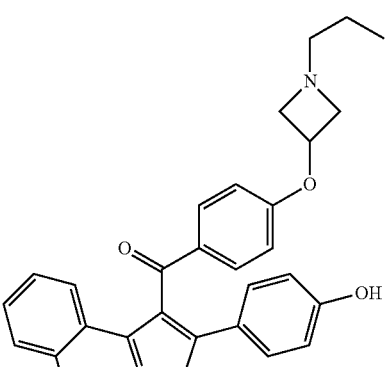
7ak
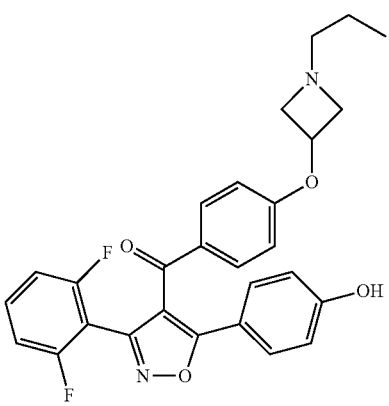
7al
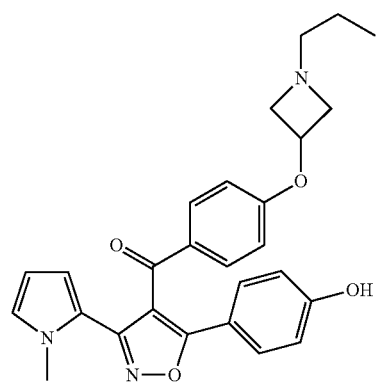
7am
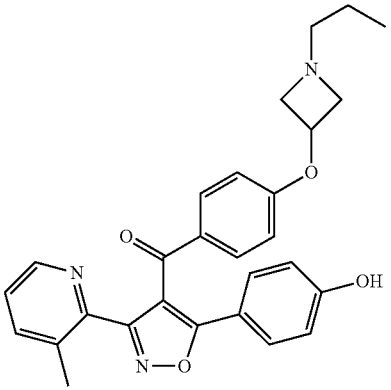

7an

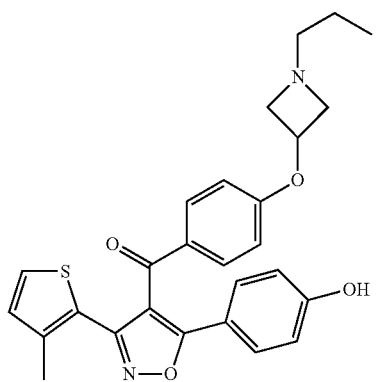

Besides being ERα antagonists with pIC50>7, the N-substituted azetidine derivatives of Formulae 7 are SERDs, showing a minimum of 20% downregulation of ERα in T47D cells, as defined hereinabove (see also Table 4 hereinbelow). In some embodiments, the N-substituted azetidines of the present invention show a relative shift towards estrogen receptor downregulation, when compared to the corresponding compounds having a classical SERM basic amine side chain (see footnotes (c) and (d) in Table 4 hereinbelow).

Formulae 7

7ao

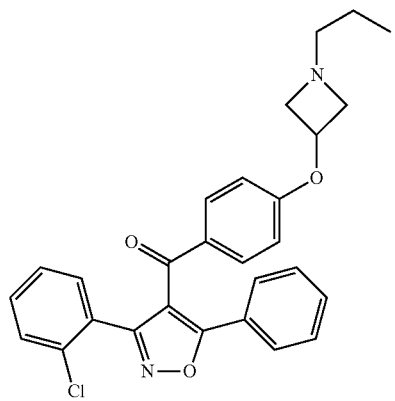

7ap

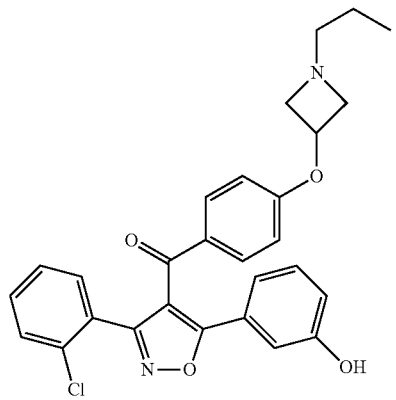

7aq

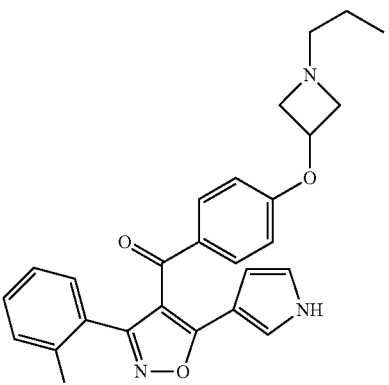

7ar

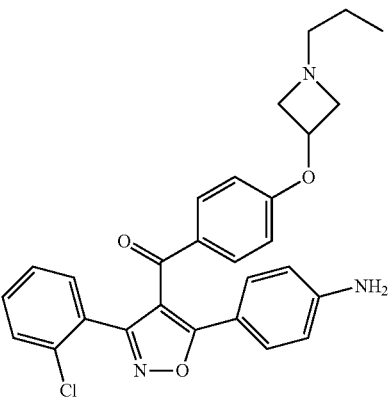

7as

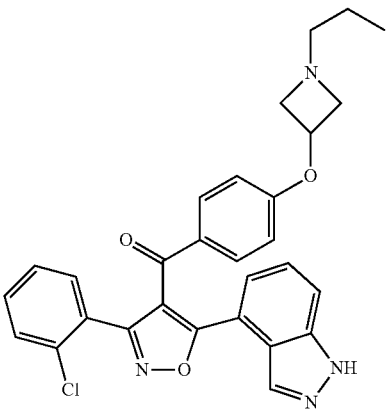

7at

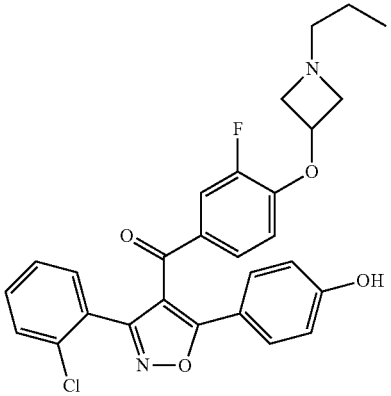

7au
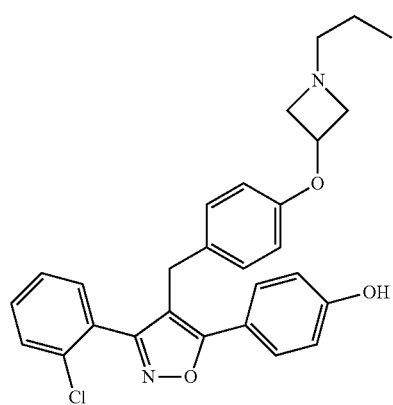
7av
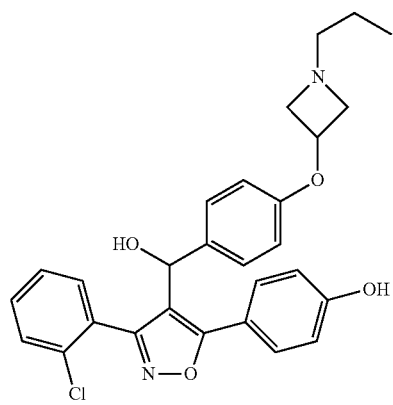
7aw
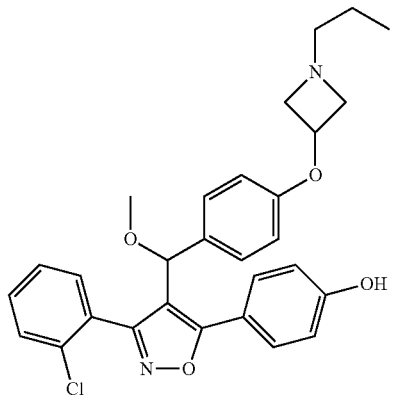
7ax
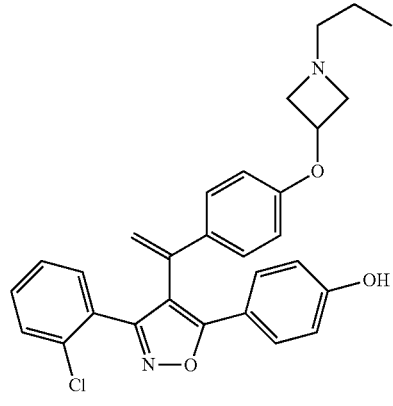
7ay
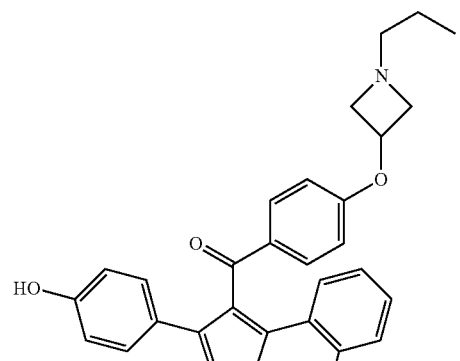
7az
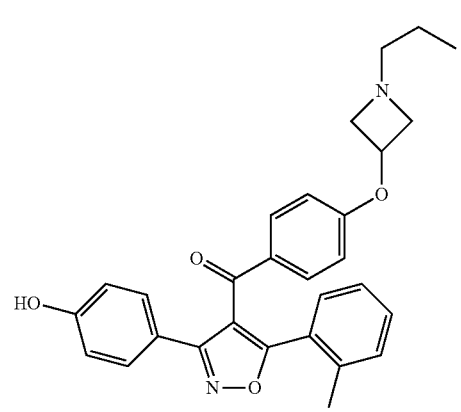
7ba
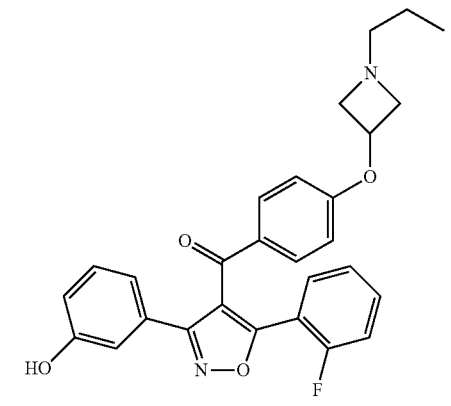
7bb
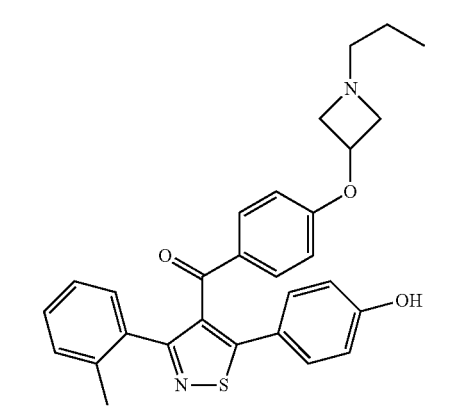

7bc 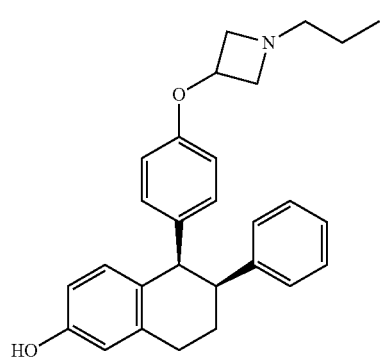
7bd 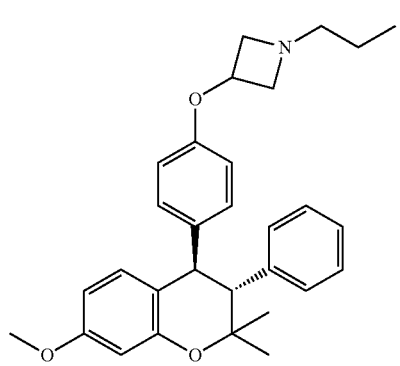
7be 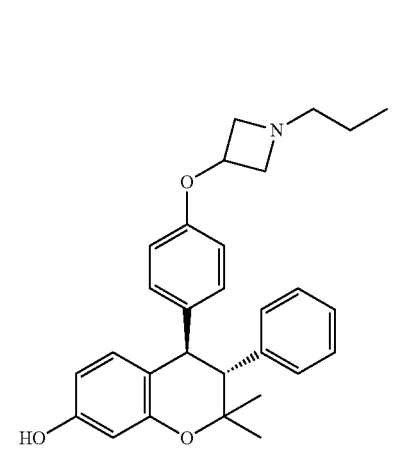
7bf 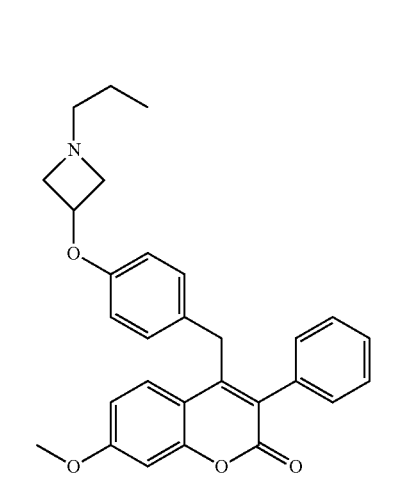
7bg 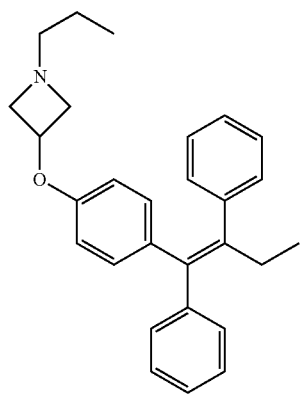
7bh 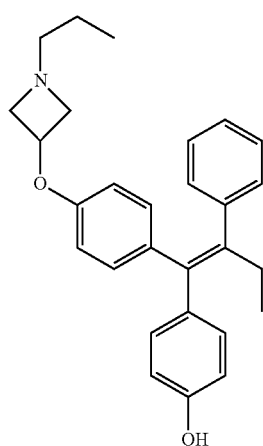
7bi 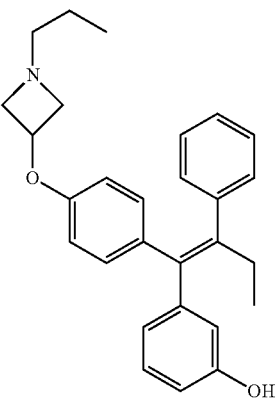
7bj 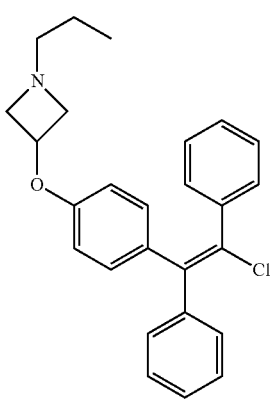

In yet another embodiment of the present invention, the N-substituted azetidine derivative is selected from the group consisting of compounds according to any one of Formulae 8a-8k, shown hereinbelow.

The N-substituted azetidine derivatives of Formulae 8 are ERα antagonists with pIC50>7, are SERDs showing a minimum of 20% downregulation of ERα in T47D cells, and do not (efficacy equal to or <0.10) stimulate proliferation in ER-positive, tamoxifen-resistant MCF-7H breast cancer cells, as defined hereinabove (see also Table 5 hereinbelow).

Formulae 8

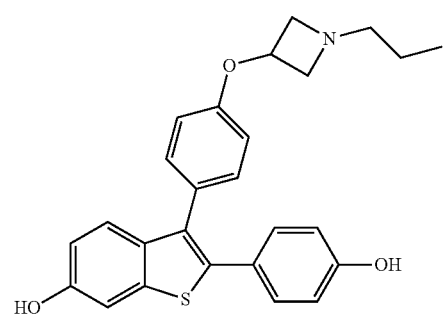
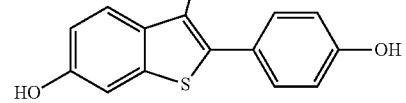

8a

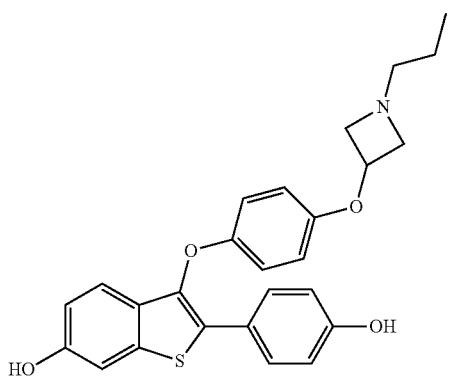
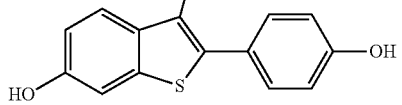

8b

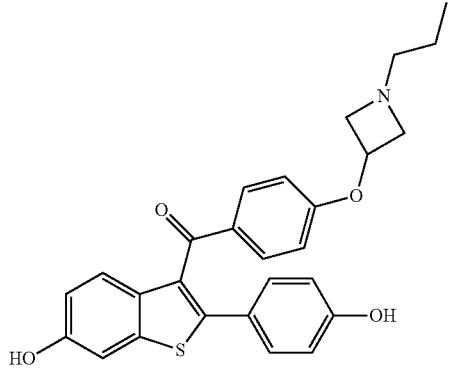

8c

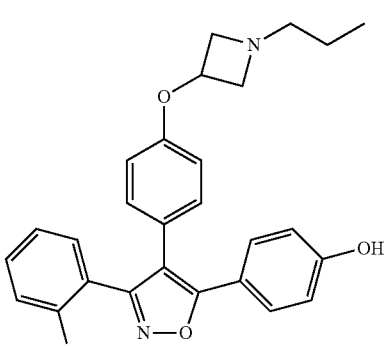

8d

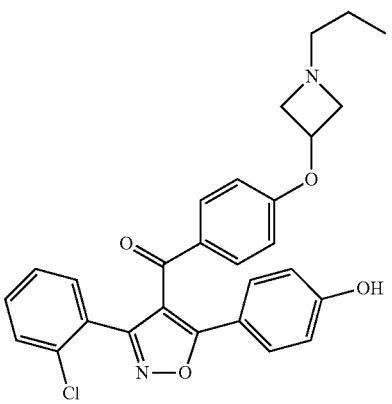

8e

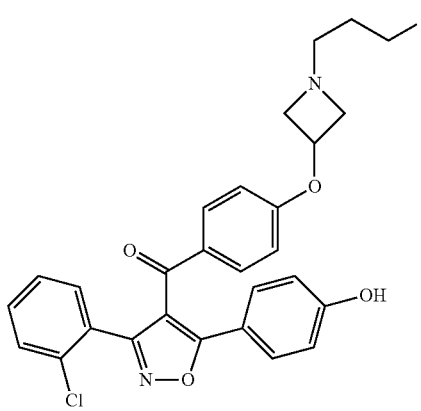

8f

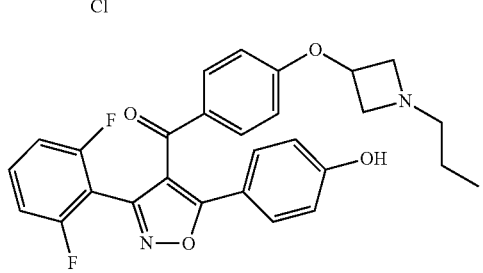

8g

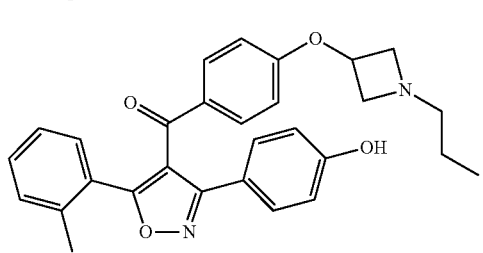

8h

-continued

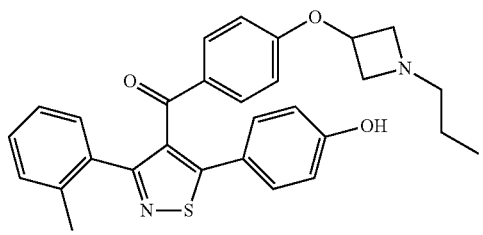
8i

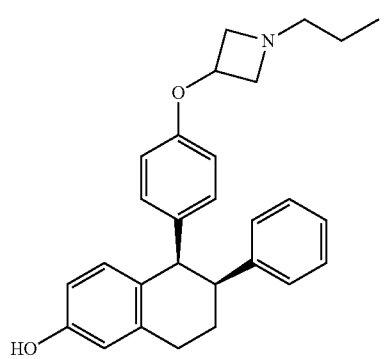
8j

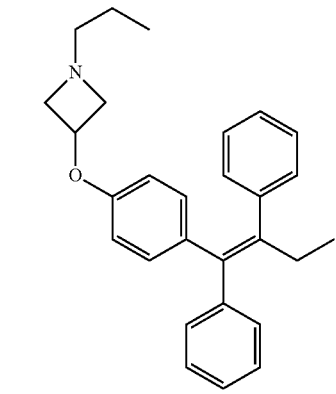
8k

Formulae 9

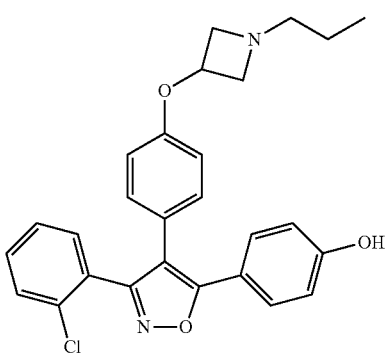
9a

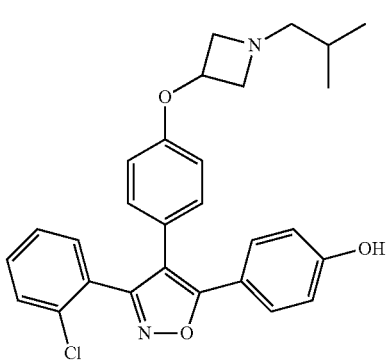
9b

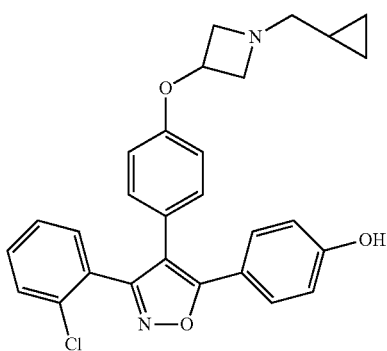
9c

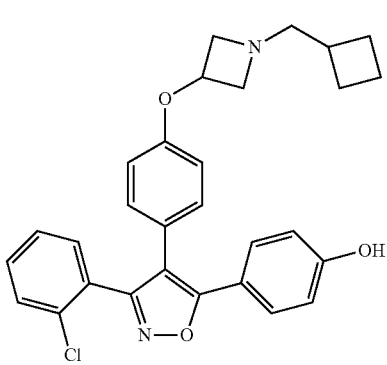
9d

In yet another embodiment of the present invention, the N-substituted azetidine derivative is selected from the group consisting of compounds according to any one of Formulae 9a-9h, shown hereinbelow.

The N-substituted azetidine derivatives of Formulae 9 are ERα antagonists with pIC50>7, are SERDs showing a minimum of 20% downregulation of ERα in T47D cells, do not (efficacy equal to or <0.10) stimulate proliferation in ER-positive, tamoxifen-resistant MCF-7H breast cancer cells, and are also orally bioavailable in the rat (see also Table 6 hereinbelow).

In the context of the present invention with "orally bioavailable" is meant that compounds, when dosed orally to a rat show oral exposure as determined by quantification of compound plasma levels in that rat. Typically, compounds are dosed orally at 20 µmol/kg, as described in Example 14 hereinbelow. Oral exposure is determined by measuring plasma levels over the time range of 0-6 h after dosing and is expressed by AUC(0-6h). Compounds are considered orally bioavailable with an AUC(0-6h)>0.3 µM·h, and preferably with an AUC(0-6h)>1 µM·h.

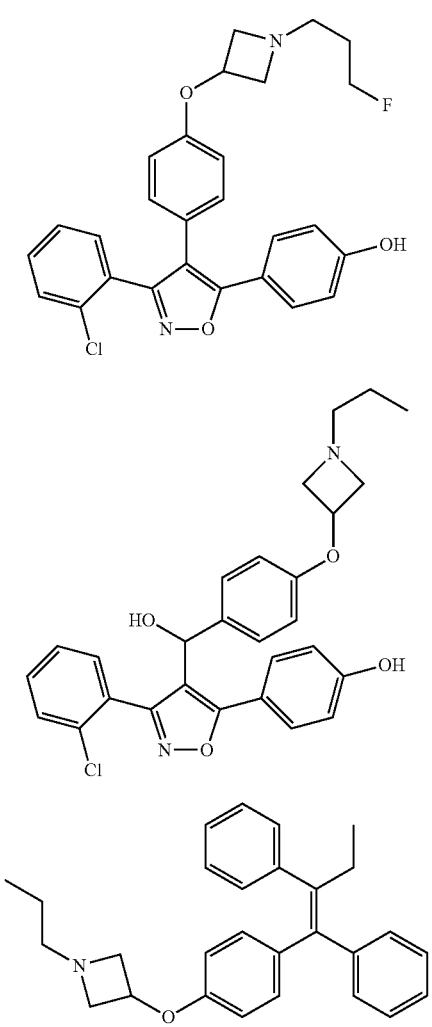

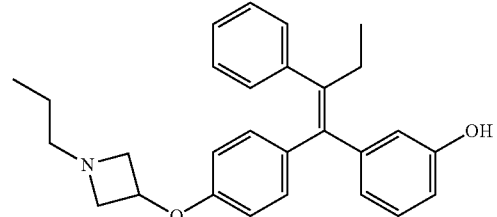

The compounds of the present invention can be produced by various methods known in the art of organic chemistry. The general synthetic procedures used to prepare the compounds described in the examples below are depicted in the following reaction schemes. Variations to these schemes can easily be made by one skilled in the art. In the following schemes, PG refers to any suitable protecting group and the R groups are as defined in the Formulae depicted above; where needed a functional group can be capped with a suitable protecting group during the synthesis.

A SERM typically contains a phenolic hydroxyl group. During the synthetic sequences described below, this phenolic hydroxyl group, when present in intermediates, generally needs to be protected. In Schemes 1-4, a methoxy group is used as an example of a protected phenolic hydroxyl group. These groups are indicated in the reaction schemes shown hereinbelow as MeO- and HO-attached to a SERMF fragment.

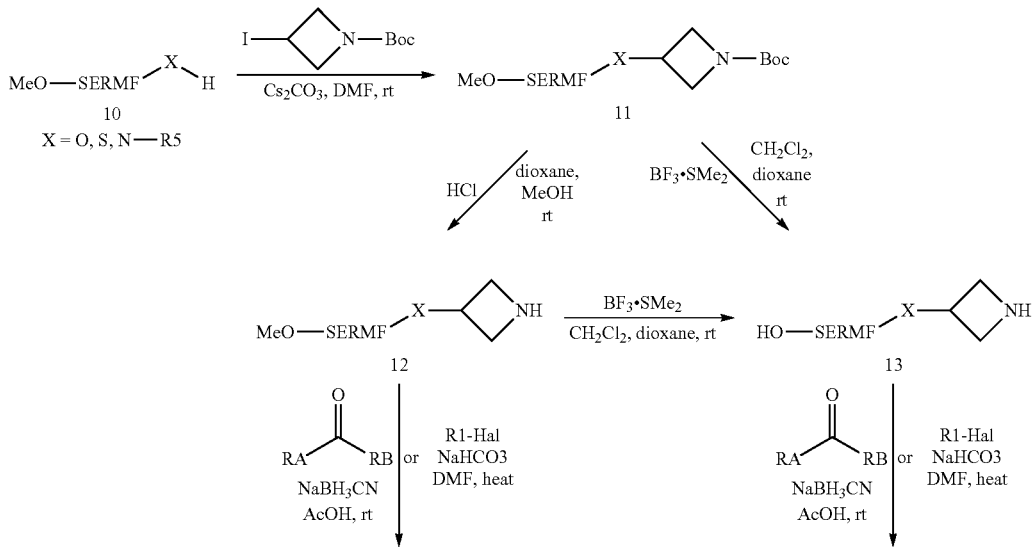

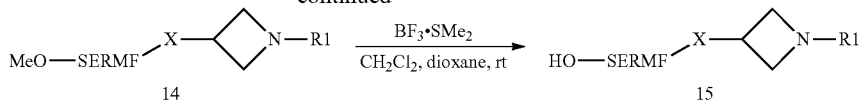

14

15

Starting from scaffold 10, containing a hydroxyl (X is O), thiol (X is S) or amine (X is N—R5) group on one side of the fragment SERMF, and on the other side a phenolic methoxy group, the X—H group is substituted by tert-butyl 3-iodoazetidine-1-carboxylate in dimethylformamide (DMF) as solvent and a suitable base, like cesium carbonate, to give the N-Boc azetidine compound 11. Deprotection of the azetidine nitrogen by removal of the Boc group, under acidic conditions, for example by treatment with hydrochloric acid in methanol and 1,4-dioxane as co-solvent, gives azetidine compound 12. The phenolic methoxy group of compound 12 can be converted to a phenol group by reaction with borontrifluoride dimethylsulfide complex in methylene chloride to give compound 13. The azetidine nitrogen of compounds 12 and 13 can be substituted by R1, for example by reaction with a suitable halide R1-Hal (Hal is Cl, Br or I) in the presence of NaHCO₃ as a base in dimethylformamide (DMF) as solvent in a sealed tube at elevated temperature under microwave irradiation to give compounds 14 and 15, respectively. Alternatively, R1 groups may be introduced by other commonly known methods in the art of organic chemistry, like reductive amination, in which R1 is introduced by reaction of unprotected azetidine 12 or 13 with an appropriate aldehyde or ketone ($R_A$(C=O)$R_B$ in which $R_A$ and $R_B$, together with the carbon atom of the carbonyl moiety, form R1) under reductive conditions, for example in the presence of sodium cyanoborohydride in a suitable solvent, like methanol or acetic acid, to give compounds 14 and 15, respectively.

An alternative route to introduce an N-substituted azetidine-X moiety onto a SERMF fragment is outlined in Scheme 2. In case the SERMF fragment contains a fluorophenyl group with an electron withdrawing group W ortho or para relative to the fluorine, like compound 22, then direct substitution on the fluorine is possible to arrive at compound 11 by an aromatic substitution reaction. The required electron withdrawing substituent can be one or both of the substituents R4 or R7 or can be the linker W connecting the fluorophenyl group to the SERMF fragment. An example of such an electron withdrawing group W is a carbonyl group. Compound 22 can be converted to compound 15 according to Scheme 1, but can also directly be converted to compound 15 by reaction with an azetidine moiety to which R1 is already attached as shown in the lower part of Scheme 2.

Scheme 2. Synthesis of compound 11 by aromatic substitution

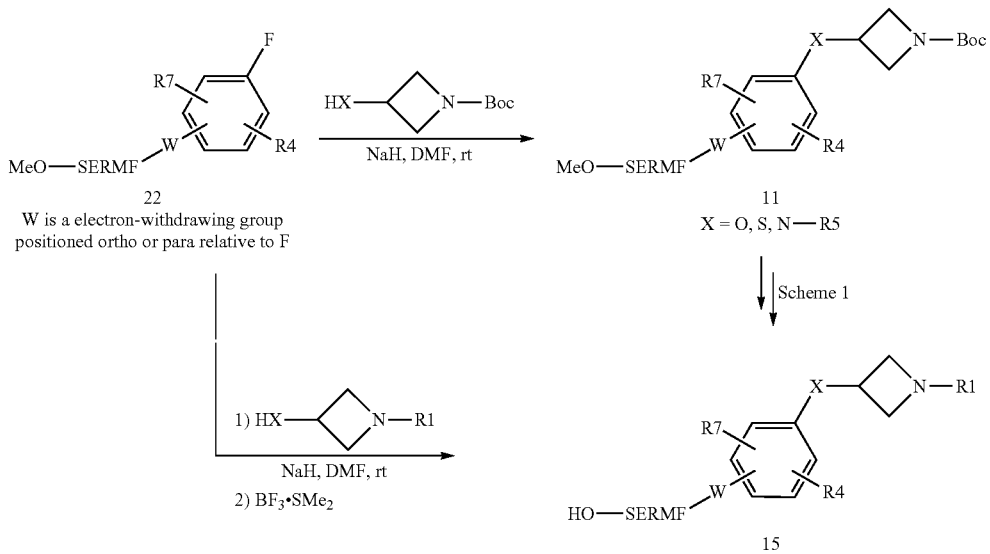

An alternative way to prepare N-substituted azetidine compounds 15 is outlined in Scheme 3. In this approach, compound 10 is substituted by 5-iodo-2-phenyl-1,3-dioxane under basic conditions, for example with sodium hydride in dimethylformamide (DMF), to give compound 16. Simultaneous deprotection of the 2-phenyl-1,3-dioxane moiety and the phenolic methoxy group on the SERMF fragment with boron tribromide in methylene chloride gives compound 17. The hydroxyl groups in compound 17 can be converted to sulfonates by reaction with a suitable sulfonyl chloride (for example tosyl chloride or mesyl chloride) under basic conditions, like sodium hydroxide in a tetrahydrofuran/water mixture, to give compound 18. The 1,3-bis-sulfonate moiety in compound 18 can be converted to an N-substituted azetidine by reaction with amine H₂N—R1 under basic conditions, for example with N,N-diisopropylethylamine in acetonitrile, resulting in the formation of compound 19. The sulfonate group attached to the phenolic hydroxyl group in compound 18 will not react under the conditions used for the conversion of compound 18 to compound 19 and will therefore still be present in compound 19. In the case of a tosyl group, it may be removed by reaction with potassium hydroxide in methanol, to give compound 15. In case the sulfonate group in compound 18 is a mesyl group, then compound 18 can be converted directly into compound 15 when the mesylate group attached to the phenolic hydroxyl group is deprotected during work-up/purification to give phenolic compound 15.

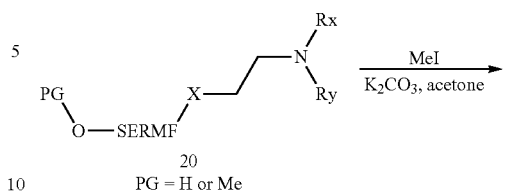

Scheme 4. Removal of basic amine side chain of a SERM

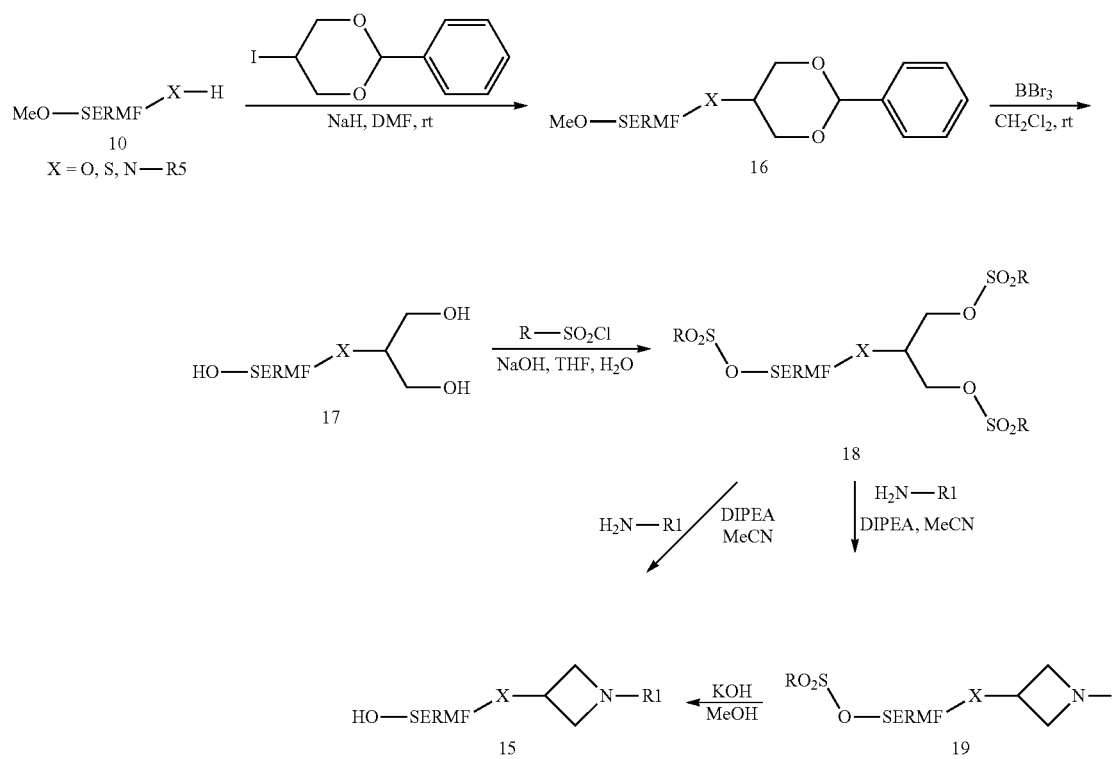

Scheme 3. Preparation of substituted azetidine derivatives through sulfonates

In those cases where the final product is an R1-substituted azetidine-X analogue of a SERM compound 20, the starting material 10 may be prepared starting from compound 20 containing a typical basic amine side chain of the general formula XCH₂CH₂NRxRy attached to the SERMF fragment, as outlined in Scheme 4.

In the first step, the amine group in compound 20 is converted to the ammonium salt by reaction with iodomethane in the presence of potassium carbonate as base in acetone as solvent, to give compound 21. Simultaneously, an unprotected phenolic hydroxyl group on the SERMF fragment of compound 20 (i.e. when PG=H) will be converted to a methoxy group. The ethylammonium side chain of 21 can be removed by a Hofmann elimination reaction, under basic conditions, for example by the use of potassium tert.-butoxide in dimethylsulfoxide (DMSO) as solvent, to give compound 10. Compound 10 can then be converted into compound 15 according to Scheme 1.

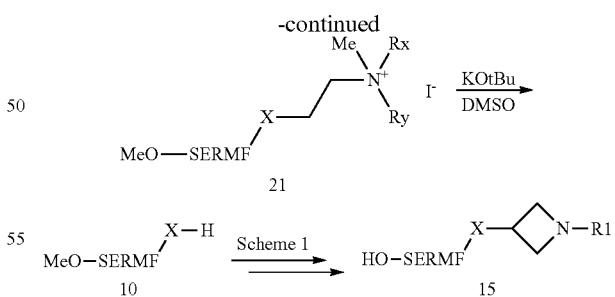

The required starting materials 10 and 22 in Schemes 1-4 can be prepared according to methods described in the literature.

In Scheme 5, synthetic routes are given for the preparation of a benzothiophene analogue of compound 10 (i.e. compound 25) and a benzothiophene analogue of compound 22 (i.e. compound 26). Such compounds can be further converted to final compounds according to Schemes 1-3. Compound 24 can also directly be converted to final compound 54 by reaction with a boronate that already contains the N-substituted azetidine moiety. Introduction of heteroaryl groups on the 2-position of a benzothiophene scaffold can be accomplished according to route C in Scheme 5. The benzothiophene compounds in Scheme 5 can be substituted with R groups as defined in any one of the relevant Formulae 4 and 5, shown hereinabove.

Scheme 5. Synthesis of benzothiophene compounds

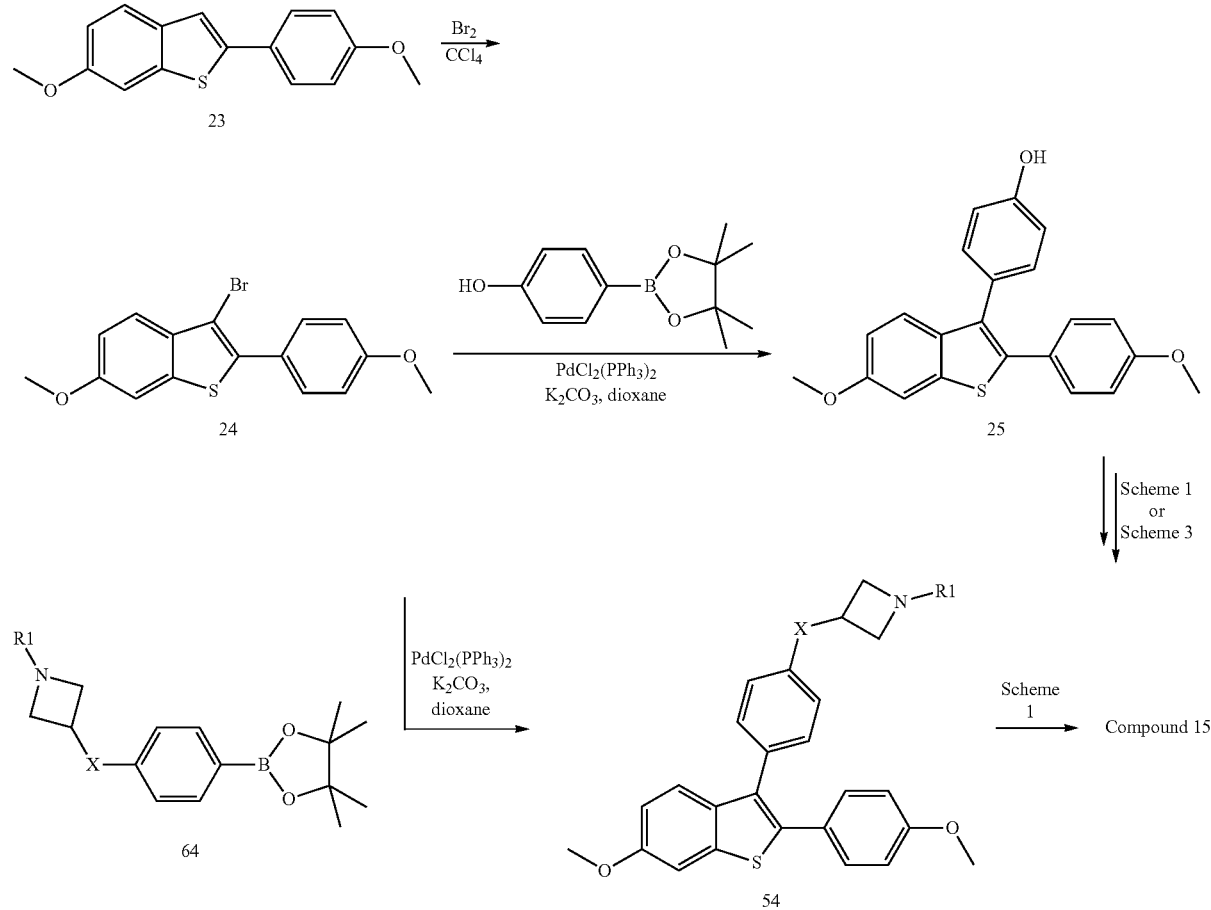

route B

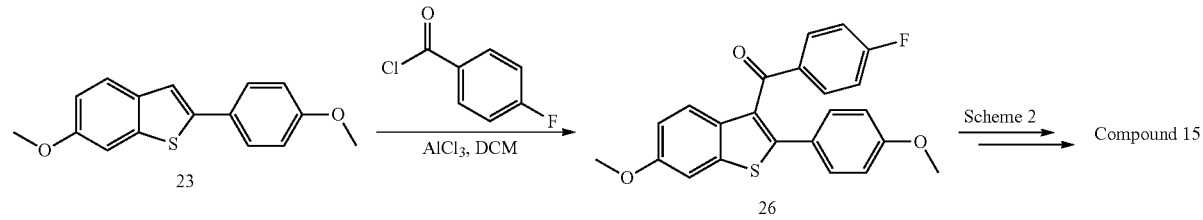

route C

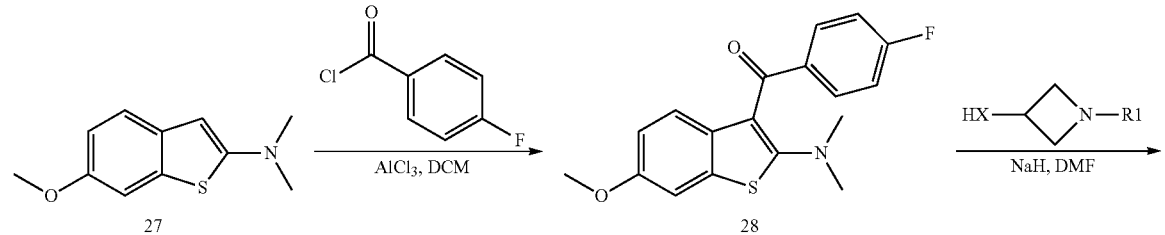

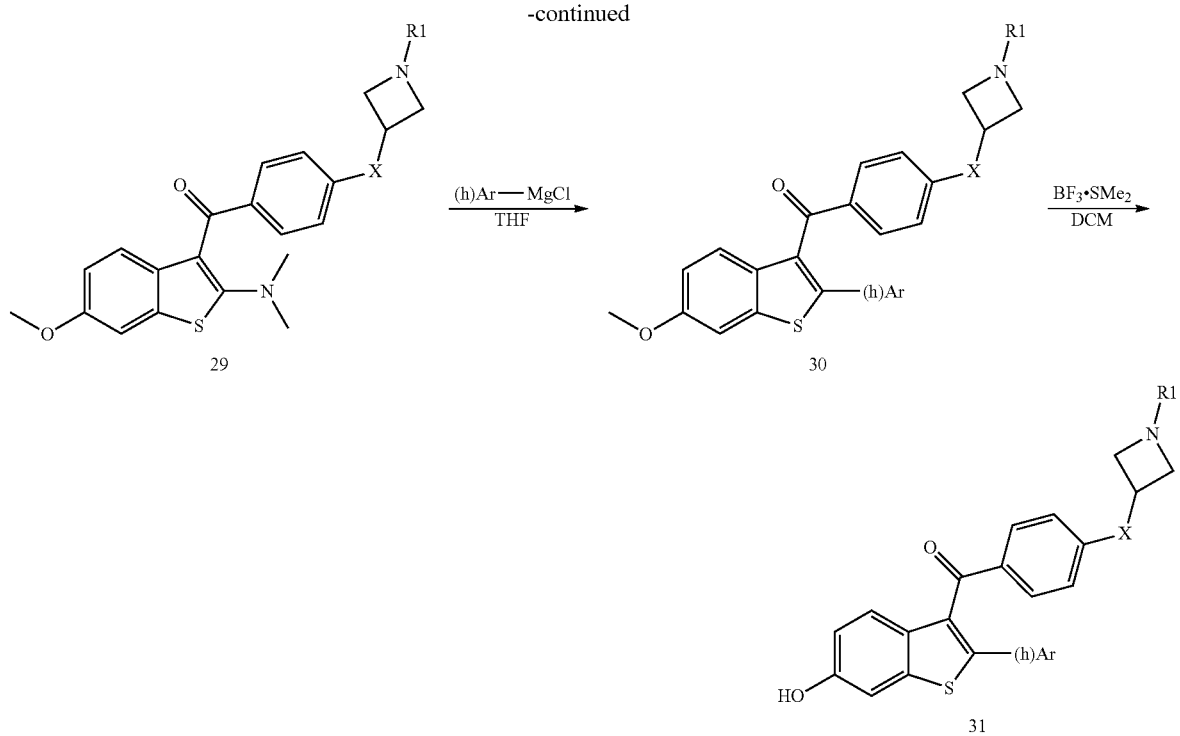

preparation of reagent 64:

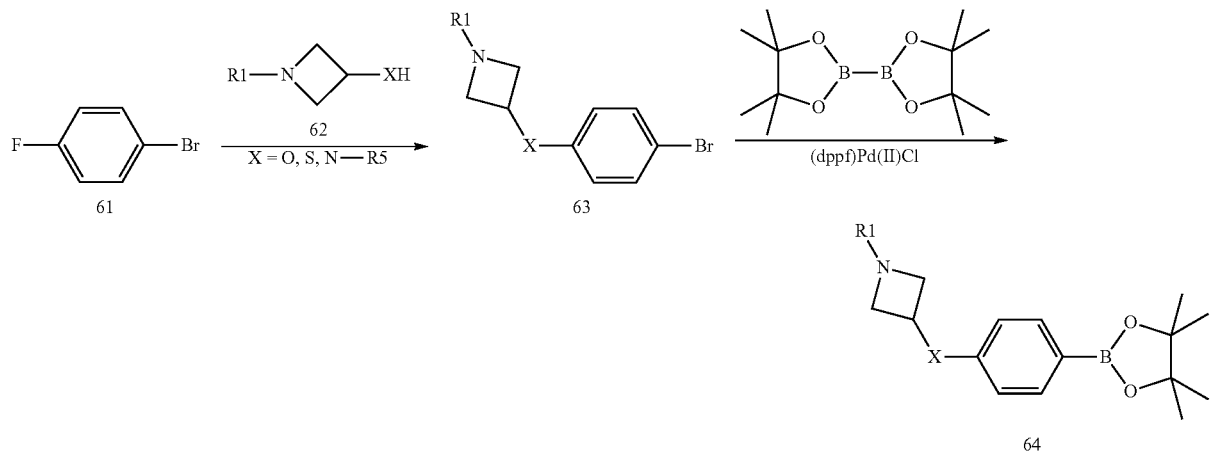

In Scheme 6, synthetic routes are given for the preparation of an isoxazole analogue of compound 10 (i.e. compound 36) and an isoxazole analogue of compound 22 (i.e. compounds 44 and 47). Such compounds can be further converted to final compounds according to Schemes 1-3. Compounds like 35 and 41 can also directly be converted to final compound 55 by reaction with a boronate that already contains the N-substituted azetidine moiety. The isoxazole compounds in Scheme 6 can be substituted with R groups as defined in any one of the relevant Formulae 4 and 5, shown hereinabove.

Scheme 6. Synthesis of isoxazole compounds

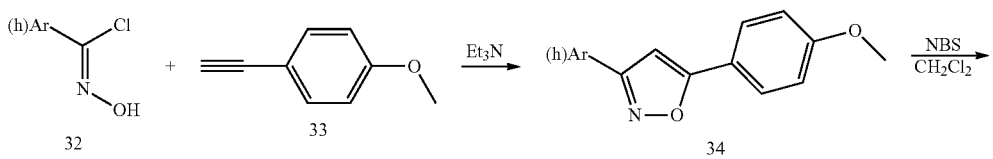

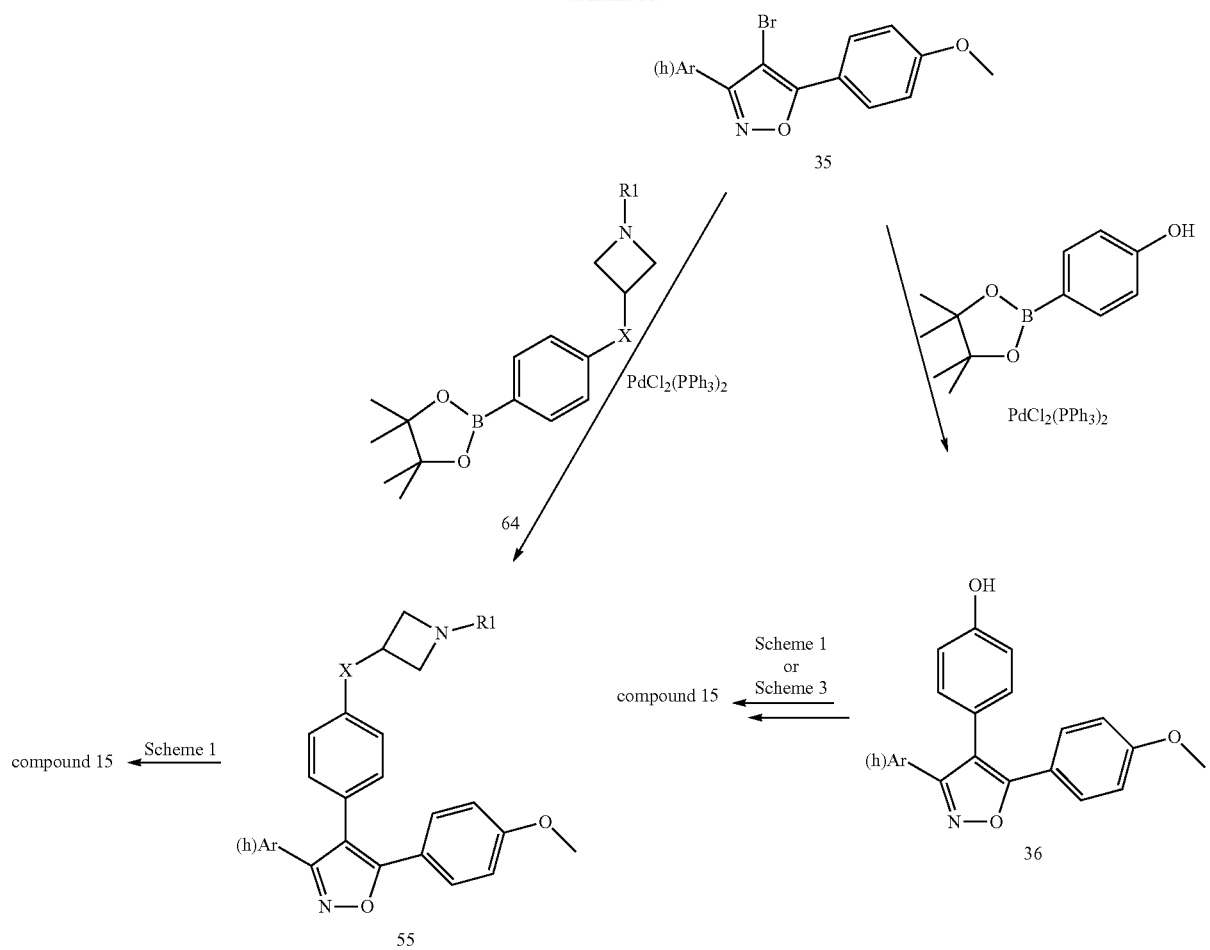
route B
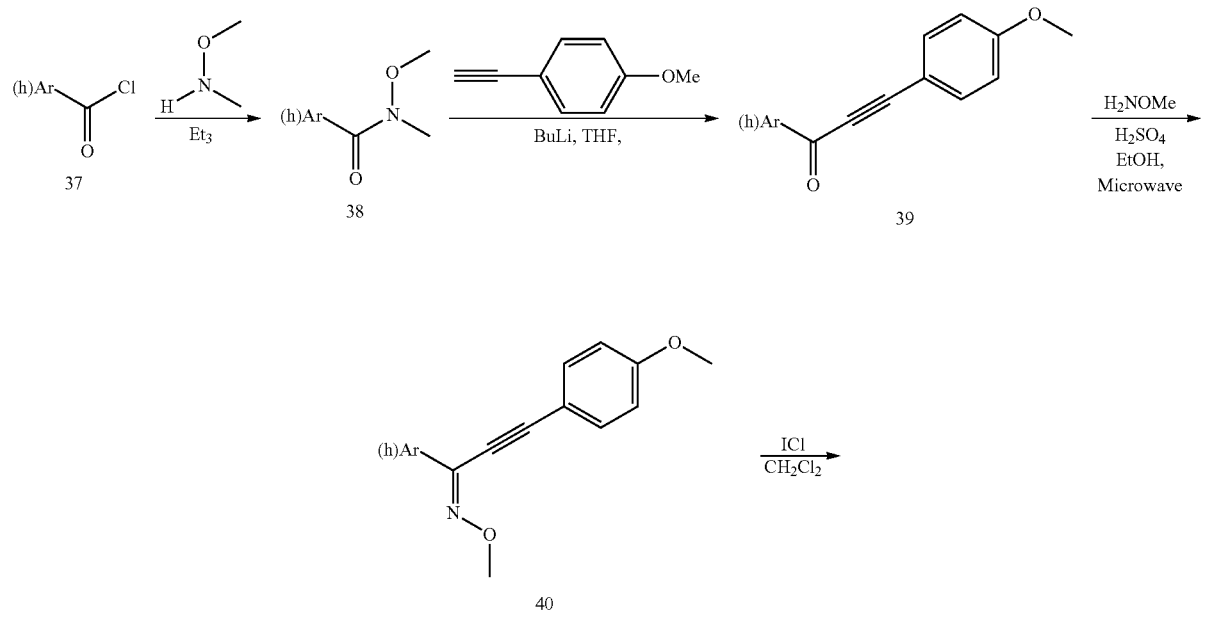

-continued
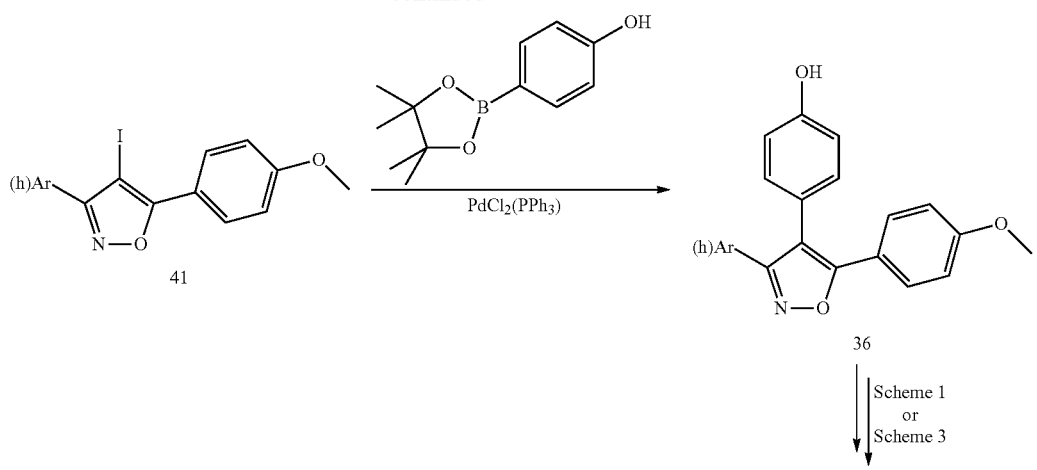
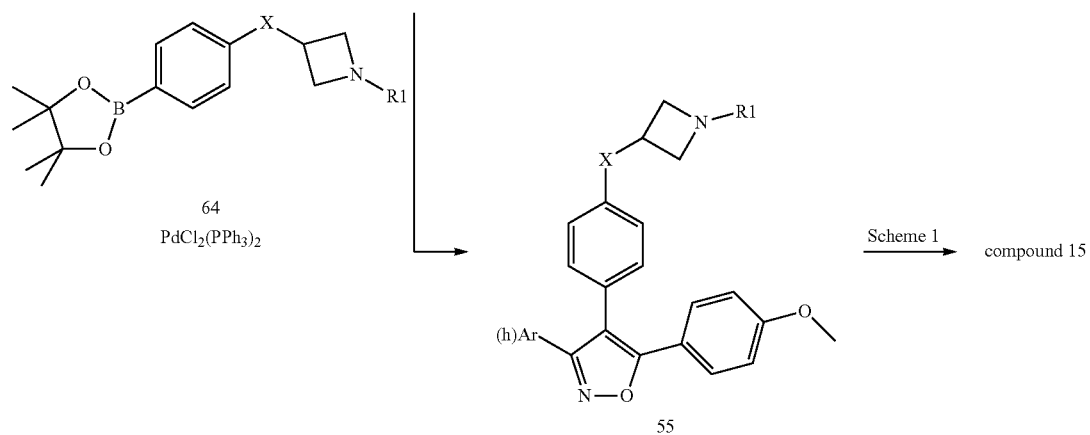
route C
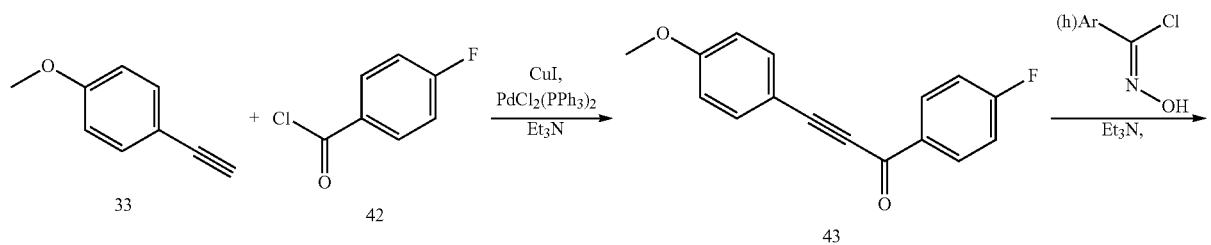
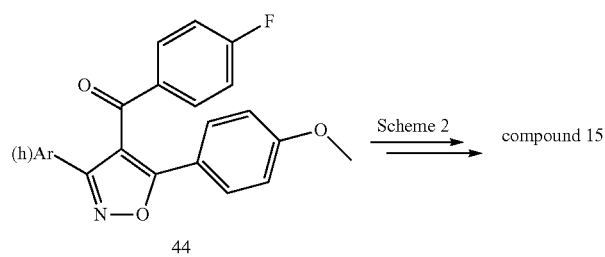

route D

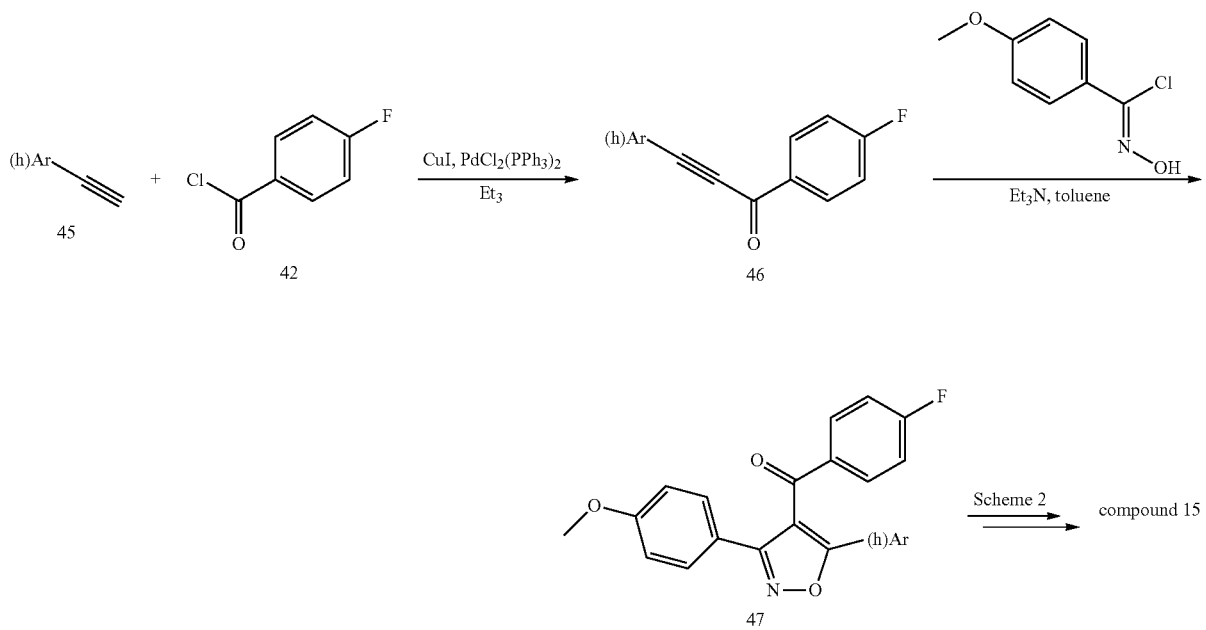

Analogues with different linker moieties V, as indicated in Formula 4, can be prepared as exemplified in Scheme 7. For example, isoxazole 56, which has a carbonyl group as linker V, can be converted to a hydroxymethylene linker analogue by reduction with sodium borohydride to give compound 57, which can be further reduced to a methylene linker analogue by reduction with triethylsilane and trifluoro acetic acid (TFA) to give compound 58. Compound 56 can also be converted to a linker with V being C=CH2, by reaction with methyllithium, to give compound 59. A compound with linker V being CH(OMe) can be obtained by stirring compound 57 in a methanolic HCl solution to give compound 60.

Scheme 7. Modification of carbonyl linker

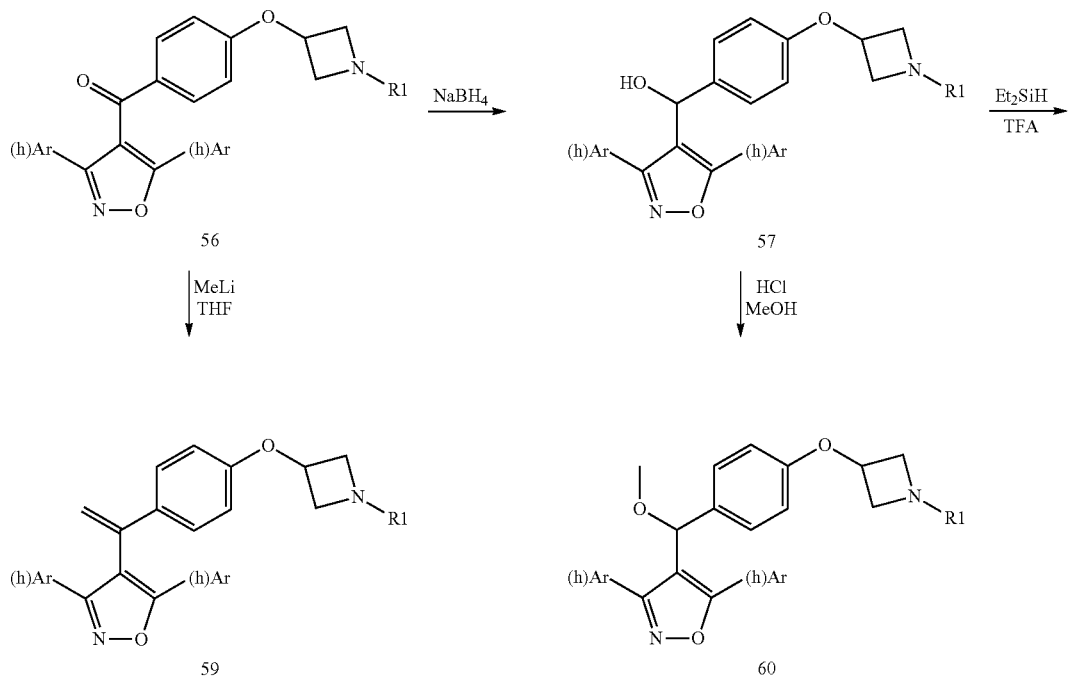

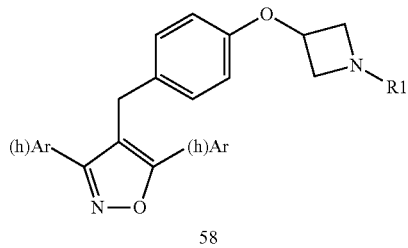

58

Isothiazoles can be prepared from isoxazoles according to the synthetic sequence shown in Scheme 8. Reductive ring-opening of isoxazole 48 gives compound 49, which can be ring-closed with phosphorus pentasulfide to give isothiazole 50. Subsequent saponification and reaction with oxalyl chloride gives acid chloride 52, which can be converted with a Grignard reagent to compound 53. Such compounds can be further converted to final compounds according to Schemes 1-3. The isothiazole compound in Scheme 8 can be substituted with R groups as defined in any one of the Formulae 4 and 5, shown hereinabove.

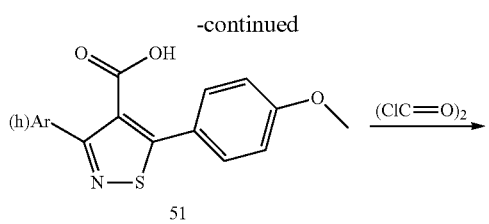

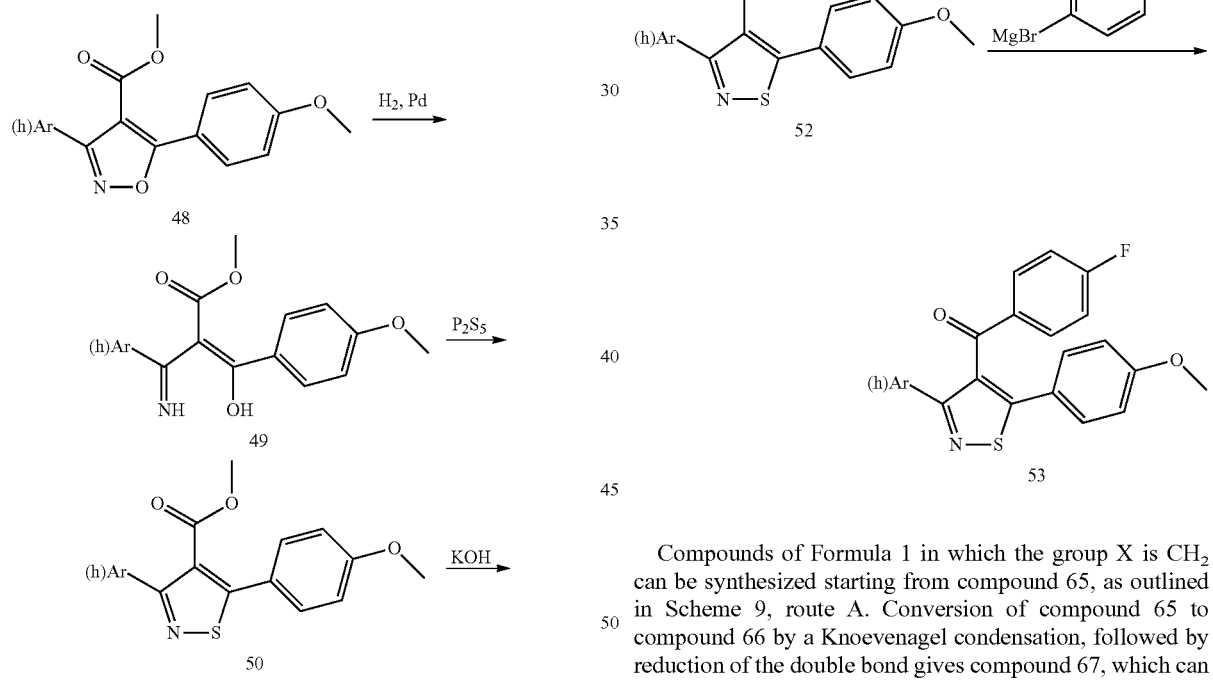

Compounds of Formula 1 in which the group X is CH$_2$ can be synthesized starting from compound 65, as outlined in Scheme 9, route A. Conversion of compound 65 to compound 66 by a Knoevenagel condensation, followed by reduction of the double bond gives compound 67, which can be converted to compound 68 according to Scheme 3.

Scheme 9. Synthesis of compounds of Formula 1 in which X is CH2, carbonyl or a direct bond route A

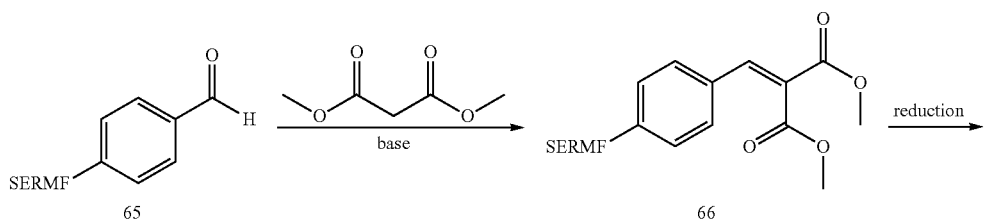

-continued

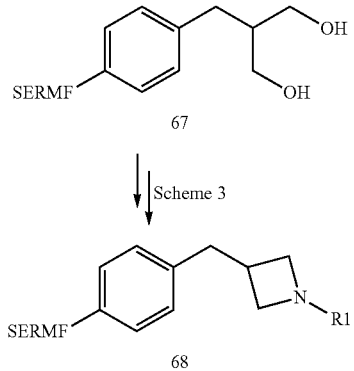

route B

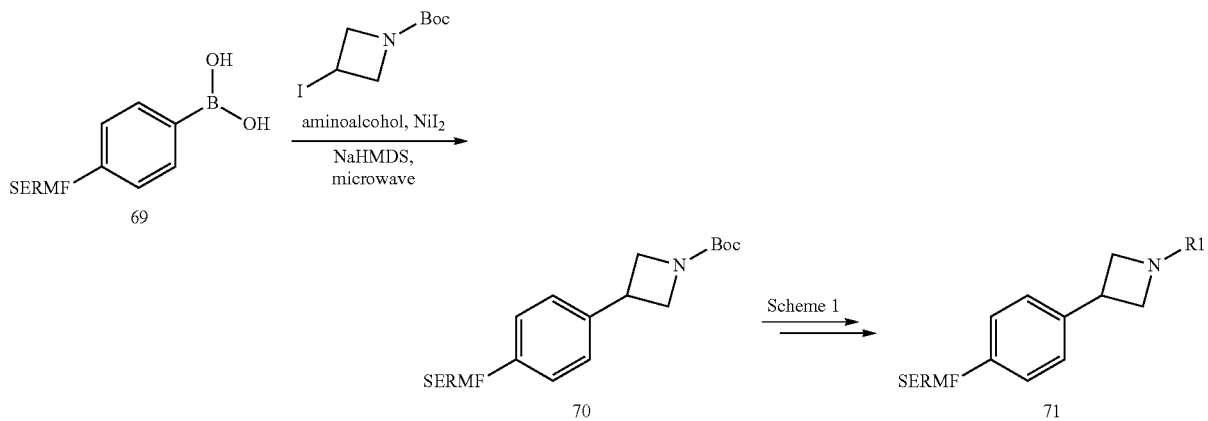

route C

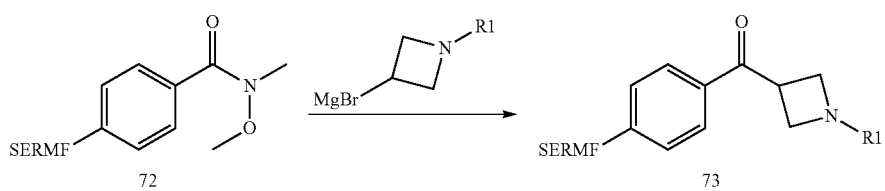

Compounds of Formula 1 in which the group X is a direct bond can be synthesized starting from compound 69, as outlined in Scheme 9, route B. Compound 69 can be converted to compound 70 by a Suzuki reaction. Compound 70 can be converted to compound 71 according to Scheme 1.

Compounds of Formula 1 in which the group X is carbonyl can be synthesized starting from compound 72, as outlined in Scheme 9, route C. Weinreb amide 72 can be converted to compound 73 by a Grignard reaction.

The enantiomers of chiral compounds may be separated in a conventional way by chiral HPLC or chiral supercritical fluid carbondioxide (SFC) HPLC, using an appropriate chiral HPLC column, for example a Chiralpak AD, OD or AS column, to give single enantiomers associated with less than 5%, preferably less than 2%, in particular less than 1% of the other enantiomer.

Ester prodrugs can be made of the parent compounds by esterification of free hydroxyl groups, for example by reaction with an appropriate acid anhydride in pyridine.

In a further aspect, the N-substituted azetidine derivatives of the present invention and their prodrugs, isotopically-labelled derivatives or pharmaceutically acceptable salts thereof, i.e. in accordance with any one of the Formulae described hereinabove, are useful in therapy. As such the N-substituted azetidine derivatives of the present invention are useful for the prevention or treatment of ovulatory dysfunction, uterine cancer, endometrium cancer, ovarian cancer, endometriosis, osteoporosis, prostate cancer, benign prostatic hypertrophy, and breast cancer, in particular ER-positive, hormone treatment-resistant breast cancer.

The present invention further includes a method for the treatment of a mammal, including a human and an animal, suffering from or liable to suffer from any of the aforementioned diseases or disorders, which comprises administering a therapeutically effective amount of an N-substituted azetidine derivative according to the present invention or a prodrug, isotopically-labelled derivative or pharmaceutically acceptable salt thereof to a mammal in need thereof. By effective amount or therapeutically effective amount is meant an amount of compound or a composition of the present invention effective in inhibiting the above-noted diseases and thus producing the desired therapeutic, ameliorative, inhibitory or preventative effect.

The present invention also relates to a method of preventing or treating ovulatory dysfunction, uterine cancer, endometrium cancer, ovarian cancer, endometriosis, osteoporosis, prostate cancer, benign prostatic hypertrophy, and breast cancer, in particular ER-positive, hormone treatment-resistant breast cancer, comprising administering therapeutically effective amounts of an N-substituted azetidine derivative in accordance with the present invention to a mammal in need thereof.

In another aspect, the present invention relates to the use of an N-substituted azetidine derivative, in accordance with any one of the Formulae described hereinabove, in combination with an agent, or a therapy, that reduces circulating levels of estrogens in premenopausal women suffering from endometriosis. Examples of such agents or therapies being treatment with progestagens, selective progesterone receptor modulators (SPRMs), gonadotropin releasing hormone receptor (GnRH-R) agonists or antagonists, or combined estrogen-progestagen preparations—also known as contraceptives.

In a still further aspect, the present invention relates to a pharmaceutical composition comprising an N-substituted azetidine derivative in accordance with the present invention in admixture with a pharmaceutically acceptable excipient. With a pharmaceutically acceptable excipient is meant one or more pharmaceutically acceptable excipients.

The present invention also relates to a method of preventing or treating ovulatory dysfunction, uterine cancer, endometrium cancer, ovarian cancer, endometriosis, osteoporosis, prostate cancer, benign prostatic hypertrophy, and breast cancer, in particular ER-positive, hormone treatment-resistant breast cancer, comprising administering therapeutically effective amounts of a pharmaceutical composition comprising an N-substituted azetidine derivative in admixture with a pharmaceutically acceptable excipient in accordance with the present invention to a mammal in need thereof.

In a preferred embodiment, the present invention relates to the use of an N-substituted azetidine derivative in accordance with any one of Formulae 6, 7, 8 or 9 for the prevention or treatment of ovulatory dysfunction, uterine cancer, endometrium cancer, ovarian cancer, endometriosis, osteoporosis, prostate cancer, benign prostatic hypertrophy, and breast cancer, in particular ER-positive, hormone treatment-resistant breast cancer. Relevant biological activity data of the compounds according to any one of Formulae 6, 7, 8 or 9 can be found in Tables 3, 4, 5 and 6, respectively, as depicted hereinbelow.

In another preferred embodiment, the present invention relates to the use of an N-substituted azetidine derivative in accordance with any one of Formulae 6, 7, 8 or 9 for the treatment of ER-positive, tamoxifen-resistant breast cancer.

The amount of N-substituted azetidine derivative in accordance with the present invention, also referred to herein as the active ingredient, which is required to achieve a therapeutic effect will, of course, vary with the particular compound, the route of administration, the age and condition of the recipient and the particular disorder or disease being treated.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a suitable dosage for humans may be 0.0001-10 mg per kilogram body weight, more in particular 0.01-10 mg per kilogram body weight. The desired dose may be presented as one dose or as multiple subdoses administered at appropriate intervals throughout the day or as doses to be administered at appropriate daily intervals. It may also be administered once-a-week or once-a-month. The dosage as well as the regimen of administration may differ between a female and a male recipient.

Whilst it is possible for the active ingredient to be administered alone, it is preferable to present it as a pharmaceutical composition. The present invention therefore also provides a pharmaceutical composition comprising an N-substituted azetidine derivative according to the present invention in admixture with one or more pharmaceutically acceptable excipients, such as the ones described in Gennaro et al., Remmington: *The Science and Practice of Pharmacy*, 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, pulmonary, topical (including buccal, sublingual and transdermal), parenteral (including subcutaneous, intravenous and intramuscular) or rectal administration.

The mixtures of an N-substituted azetidine derivative according to the present invention and one or more pharmaceutically acceptable excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The present invention further includes a pharmaceutical composition, as hereinbefore described, in combination with packaging material suitable for said composition, said packaging material including instructions for the use of the composition as described hereinbefore.

The present invention is illustrated in the following examples.

EXAMPLES

In the following examples, the numbering of compounds follows the numbering of compounds shown in the Schemes of the description above. Analytical data on the compounds of Formulae 6, 7, 8 and 9 synthesized can be found in Tables 3, 4, 5 and 6, respectively hereinbelow.

General Procedure A

Synthesis According to Scheme 1

Step 1—Coupling with 1-Boc-3-Iodo-Azetidine

A suspension of compound 10 and cesium carbonate (4 equivalents) in dimethylformamide (DMF) was stirred for 5 minutes at room temperature under N₂ atm. Then 1-Boc-3-iodo-azetidine (2 equivalents) was added. This reaction mixture was stirred overnight at room temperature. The reaction mixture was poured into water and extracted with ethyl acetate. The combined organic layers were washed with brine, dried (Na₂SO₄) and evaporated to dryness to afford the crude compound, which was purified by column chromatography (EtOAc/Heptane) to give the desired Boc azetidine 11.

Step 2—Acidic Cleavage of Boc Group

To a solution of Boc azetidine 11 in methanol, 15 equivalents of hydrogen chloride (4 N in dioxane) was added. The reaction mixture was stirred for 3h at room temperature. According to LCMS desired product was formed. The reaction mixture was diluted with methanol and was concentrated. The resulting residue was used in the next step without purification or was triturated with diethyl ether and subsequently filtered over a medium fritted glass funnel, rinsed with diethyl ether, and collected to give compound 12 as a white solid.

Step 3—Reductive Amination of Azetidine

To a mixture of compound 12, aldehyde R1-CHO (2 equivalents) and sodium cyanoborohydride (2 equivalents) in methanol and molsieves (3 Å), acetic acid (1 equivalent) was added. This reaction mixture was stirred overnight at room temperature under N₂ atm. The reaction mixture was diluted with methanol, filtered and then flushed over a SCX-2 column with methanol to get rid of the impurities. Then the desired product was eluted with 0.7 N ammonia/methanol solution to give compound 14.

Step 4—Demethylation of Methoxy (and Cleavage of Boc, if Present)

To a solution of compound 14 in dichloromethane (DCM) borontrifluoride-methyl sulfide complex (20 equivalents) was added. This reaction mixture was stirred overnight at room temperature under N₂ atm. The reaction mixture was quenched with methanol and stirred at room temperature for 30 min. The mixture was further diluted with methanol, filtered and loaded onto a SCX-2 column. The SCX-2 column was flushed with methanol to get rid of the impurities and was then eluted with 0.7 N ammonia solution to obtain the desired product. The crude product was concentrated and purified by prep. HPLC (acetonitrile/water). The product-containing fractions were freeze-dried to afford compound 15 as a white solid.

General Procedure B

Synthesis According to Scheme 2

To a suspension of 1-Boc-3-(hydroxy)azetidine (0.5 mmol) and cesium carbonate (1.5 mmol) in dimethylformamide (4 ml) was added compound 22 (0.25 mmol). The mixture was stirred under a nitrogen atmosphere at room temperature for 16 h. Then water was added and the mixture was extracted with ethyl acetate (2×). The combined organic layers were washed with brine (1×), dried (Na₂SO₄) and concentrated. The crude product was purified by prep. HPLC (acetonitrile/water) to give compound 11 in good purity.

Under a nitrogen atmosphere, at room temperature, sodium hydride (70 mmol; washed with heptane) was suspended in dimethylformamide (120 ml). Then 1-propylazetidin-3-ol hydrochloride (19.9 mmol) was added slowly and the resulting mixture was stirred at room temperature for 15 min. Then, compound 22 (PG=H or Me) (11.7 mmol) was added and the mixture was stirred at room temperature for 16 h. Water was added and the mixture was extracted with ethyl acetate (4×). The combined organic layers were washed with brine (1×), dried (Na₂SO₄) and concentrated. The crude product was purified by prep. HPLC (acetonitrile/water). The product-containing fractions were freeze-dried from acetonitrile/2N HCl to afford the target compound as HCl salt as a white solid in good purity.

Compound 14 (PG=Me) can be converted to compound 15 (PG=H) according to General Procedure A, Step 4.

General Procedure C

Synthesis According to Scheme 3

Step 1

To a stirring solution of 2-phenyl-1,3-dioxan-5-ol (60 mmol) in dimethylformamide (145 ml), at room temperature and under a nitrogen atmosphere, was added sodium hydride (159 mmol) and the mixture was stirred for 20 min. To this mixture a solution of compound 10 (26 mmol) in dimethylformamide (105 ml) was added. The resulting mixture was stirred at room temperature for 16 h. The reaction was quenched with saturated aqueous ammonium chloride solution and the mixture was extracted with ethyl acetate (4×). The combined organic layers were washed with water (1×) and brine (1×), dried (Na₂SO₄) and concentrated to give compound 16, which was used as such in the next step.

Step 2

Under a nitrogen atmosphere, compound 16 (29 mmol) was dissolved in methylene chloride (700 ml). The mixture was cooled to 0° C. and boron tribromide (147 mmol) was added. The reaction mixture was stirred at 0° C. for 90 min and was then poured into ice/water. The resulting mixture was extracted with ethyl acetate (2×). The combined organic layers were washed with brine (1×), dried (Na₂SO₄) and concentrated. The crude product was purified by column chromatography over silica to give compound 17 in good purity.

Step 3

Under a nitrogen atmosphere at 0° C. compound 17 (18 mmol) and triethylamine (151 mmol) were dissolved in ethyl acetate (250 ml), methanesulphonyl chloride (149 mmol) was added and the resulting mixture was stirred for 16 h. Then, ethyl acetate was added and the mixture was washed with water. The organic layer was dried (Na₂SO₄) and concentrated to give compound 18, which was used as such in the next step.

Step 4

A solution of compound 18 (SO₂R=mesyl) (0.21 mmol) and amine R1-NH₂ (5 equivalents) in acetonitrile (6 ml) was stirred at 100° C. in a sealed tube for 16 h. The reaction mixture was concentrated and was purified by prep. HPLC (acetonitrile/water). To the product-containing fractions 4N HCl was added and the mixture was freeze-dried to afford compound 15 as a white solid in good purity.

Step 5

A solution of compound 18 (SO$_2$R=tosyl) (0.20 mmol) and amine R1-NH$_2$ (5 equivalents) in acetonitrile (6 ml) was stirred at 100° C. in a sealed tube for 16 h. The reaction mixture was concentrated and was purified by prep. HPLC (acetonitrile/water). To the product-containing fractions 4N HCl was added and the mixture was freeze-dried to afford compound 19 as a white solid in good purity.

Step 6

To a solution of compound 19 (0.04 mmol) in methanol (3 ml) was added potassium hydroxide (200 mg). The mixture was stirred at 80° C. in a sealed tube for 2 h and was then cooled to room temperature and loaded onto an SCX-2 column (10 g column material). The column was washed with methanol and then the product was eluted with 0.7M ammonia in methanol. The crude product was further purified by prep. HPLC (acetonitrile/water). The product-containing fractions were mixed with 4N HCl and the mixture was freeze-dried to afford compound 15 as a white solid in good purity.

General Procedure D

Synthesis According to Scheme 4

Step 1—Converting the Amine Group to the Ammonium Salt

A yellow suspension of compound 20, iodomethane (8 equivalents), and potassium carbonate (8 equivalents) in acetone was stirred at room temperature for 16 h. The reaction mixture was diluted with methanol and was concentrated. The resulting crude product was either used directly in the next step without purification or was triturated with diethyl ether, filtered through a medium fritted glass funnel, rinsed with diethyl ether, giving the desired ammonium salt 21 after collection as a yellow solid in quantitative yield.

Step 2—Cleavage of Ethylammonium Side Chain

A solution of compound 21 and potassium tert-butoxide (5 equivalents) in DMSO was stirred for 3h at room temperature. The reaction mixture was diluted with water and HCl was added until pH=1. The mixture was stirred for another 15 min and was then extracted with ethyl acetate. The combined organic layers were washed with water, brine, dried (Na$_2$SO$_4$) and evaporated to dryness to afford the crude compound, which was purified by column chromatography (EtOAc/Heptane) to give the desired phenol 10 in excellent yield.

Compound 10 can be converted to compound 15 according to General Procedure A.

General Procedure E

Syntheses According to Scheme 5

Compound 24 can be prepared as described in literature (A. D. Palkowitz et al., *J. Med. Chem.* 40 (1997) 1407-1416).

A solution of compound 24 (1.0 mmol), 4-(4,4,5,5-tetramethyl-1,3,2-dioxaborolan-2-yl)phenol (2.0 mmol), K$_3$PO$_4$.7H$_2$O (3.0 mmol) and PdCl$_2$(PPh$_3$)$_2$ (0.05 mmol) in dioxane (10 ml) was stirred under N$_2$ atmosphere at 90° C. for 16 h. The reaction mixture was then cooled to room temperature. Water was added and the mixture was extracted with ethylacetate (3×). The combined organic layers were washed with brine (1×), dried (Na$_2$SO$_4$) and concentrated. The crude product was purified by column chromatography to give compound 25 in good purity.

Synthesis of Pinacolboronate 64

Step 1

Under a nitrogen atmosphere, sodium hydride (30 mmol) was added to anhydrous dimethylformamide (10 ml) and then compound 62 (15 mmol) was added. The mixture was stirred at room temperature for 30 min. Then a solution of 4-bromofluorobenzene (18 mmol) in dimethylformamide (5 ml) was added dropwise. The mixture was stirred at 60° C. for 16 h. Then, ethyl acetate was added and the mixture was poured into water. The organic phase was separated and washed with water (3×) and brine (1×), dried (Na$_2$SO$_4$) and concentrated. The crude product was purified by column chromatography over silica(methylene chloride/-methanol) to afford compound 63 in good purity.

Step 2

Under a nitrogen atmosphere, compound 63 (10 mmol), bis(pinacolato)diboron (15 mmol) and potassium acetate (10 mmol) were dissolved in dioxane (30 ml). Then 1,1'bis (diphenylphosphino)ferrocene palladium(II) chloride (0.5 mmol) was added and the mixture was stirred at 80° C. for 16 h. The reaction mixture was poured into water and was extracted with ethyl acetate (2×). The organic layers were dried (Na$_2$SO$_4$) and concentrated. The crude product was purified by column chromatography over silica(methylene chloride/methanol) to afford compound 64 in good purity.

A solution of compound 24 (1.0 mmol), compound 64 (2.0 mmol), K$_3$PO$_4$.7H$_2$O (3.0 mmol) and PdCl$_2$(PPh$_3$)$_2$ (0.05 mmol) in dioxane (10 ml) was stirred under N$_2$ atmosphere at 90° C. for 16 h. The reaction mixture was then cooled to room temperature. Water was added and the mixture was extracted with ethylacetate (3×). The combined organic layers were washed with brine (1×), dried (Na$_2$SO$_4$) and concentrated. The crude product was purified by column chromatography to give compound 54 in good purity.

Compounds 25 and 54 can be converted to compound 15 according to General Procedure A.

Compound 26 can be prepared according to the method described by C. Yang et al., *Bioorg. Med. Chem. Lett.* 15 (2005) 1505-1507. Compound 26 can be converted to compound 15 according to General Procedure A.

The syntheses in Scheme 5, route C were performed analogously to the methods described by D. A. Bradley et al. in *Tetrahedron Letters* 40 (1999) 5155-5159.

General Procedure F

Synthesis According to Scheme 6, Route A

Step 1

(E/Z)-2-chlorobenzaldehyde oxime

To a cooled (5° C.) solution of 2-chlorobenzaldehyde (40.1 ml, 356 mmol) in ethanol (100 ml) was added an aqueous solution of hydroxylamine (27.2 g; 391 mmol) in water (100 ml), followed by addition of 5N sodium hydroxide (73.6 ml). The mixture was stirred at 5° C. for 90 min. The mixture was then acidified with 6N HCl until pH6 was reached and was extracted with tert.butylmethylether (3×). The combined organic layers were dried (Na$_2$SO$_4$) and concentrated to give the target compound as a white solid (55 g; 99% yield; HPLC purity 97%). The product was used as such in the next step.

Step 2

(E/Z)-2-Chloro-N-Hydroxybenzimidoyl Chloride (an example of compound 32)

To a cooled (10° C.) solution of (E/Z)-2-chlorobenzaldehyde oxime (4.0 g, 25.7 mmol) in DMF (12 ml) was added N-chlorosuccinimide (3.43 g, 25.7 mmol) in portions. After the addition was complete, water (50 ml) was added and the reaction mixture was extracted 3× with THF. The combined organic layers were washed with water (1×), dried (Na$_2$SO$_4$) and concentrated to give the target compound as a yellow oil (4.98 g, HPLC purity 74%, quant.). The crude product was used as such in the next step.

Step 3

3-(2-Chlorophenyl)-5-(4-methoxyphenyl)isoxazole (an example of compound 34)

To a cooled (0° C.) solution of (E/Z)-2-chloro-N-hydroxybenzimidoyl chloride (0.50 g, 1.71 mmol) and 1-eth-1-ynyl-4-methoxybenzene (0.271 g, 2.05 mmol) in THF (7 ml) was added triethylamine (0.238 ml, 1.71 mmol). The mixture was stirred at room temperature for 16 h and was then filtered. The filtrate was concentrated and was recrystallized from ethanol to give the target compound as a white solid (0.33 g, HPLC purity: 99%; 68% yield).

Step 4

4-Bromo-3-(2-chlorophenyl)-5-(4-methoxyphenyl) isoxazole (an example of compound 35)

To a solution of 3-(2-chlorophenyl)-5-(4-methoxyphenyl) isoxazole (285 mg, 0.997 mmol) in DCM (3 ml) was added at room temperature N-bromosuccinimide (231 mg, 1.297 mmol) in portions, followed by p-toluenesulfonic acid (9.5 mg, 0.05 mmol). The mixture was stirred at room temperature for 17 h. The mixture was then washed with sat. aqueous Na$_2$S$_2$O$_3$ solution (2×), sat. aqueous NaHCO$_3$ solution (1×) and water (2×). The organic phase was dried (Na$_2$SO$_4$) and concentrated. The crude product was purified by prep. HPLC to give the target compound as a white solid (264 mg, HPLC purity 99%; yield: 73%).

Step 5

4-(3-(2-chlorophenyl)-5-(4-methoxyphenyl)isoxazol-4-yl)phenol (an example of compound 36)

A solution of 4-bromo-3-(2-chlorophenyl)-5-(4-methoxyphenyl)isoxazole (1.26 g, 3.46 mmol), 4-(4,4,5,5-tetramethyl-1,3,2-dioxaborolan-2-yl)phenol (1.52 g, 6.92 mmol), K$_3$PO$_4$.7H$_2$O (3.51 g, 10.38 mmol) and PdCl$_2$(PPh$_3$)$_2$ in dioxane (20 ml) was stirred under N$_2$ atmosphere at 90° C. for 16 h. The reaction mixture was then cooled to room temperature. Water was added and the mixture was extracted with ethyl acetate (3×). The combined organic layers were washed with brine (1×), dried (Na$_2$SO$_4$) and concentrated. The crude product was purified by column chromatography to give the target compound as a white solid (910 mg, yield: 70%).

Step 6 (is General Procedure A, Step 1)

tert-butyl 3-(4-(3-(2-chlorophenyl)-5-(4-methoxyphenyl)isoxazol-4-yl)-phenoxy)-azetidine-1-carboxylate To a solution of 4-(3-(2-chlorophenyl)-5-(4-methoxyphenyl)isoxazol-4-yl)phenol (740 mg, 1.959 mmol) and 1-Boc-3-iodo-azetidine (832 mg, 2.94 mmol) in DMF (20 ml) was added cesium carbonate (2.55 g, 7.83 mmol). The mixture was stirred at room temperature for 16 h. Then, ethyl acetate was added and the mixture was washed with water. The organic layer was dried (Na2SO4) and concentrated. The crude product was purified by column chromatography to give the target compound as a white solid (700 mg; yield: 67%.

$^1$H-NMR (400 MHz, CDCl$_3$): δ 4.83 (m, 1H, azetidine 3-H).

Step 7 (is General Procedure A, Step 4)

4-(4-(4-(azetidin-3-yloxy)phenyl)-3-(2-chlorophenyl)isoxazol-5-yl)phenol (compound 6f)

To a solution of tert-butyl 3-(4-(3-(2-chlorophenyl)-5-(4-methoxyphenyl)isoxazol-4-yl)phenoxy)-azetidine-1-carboxylate (533 mg, 1.00 mmol) in methylene chloride (20 ml) under N$_2$ atmosphere was added boron trifluoride-methyl sulfide complex (2.10 ml, 20.0 mmol) at room temperature. The reaction mixture was stirred for 16 h. Then water was added and the mixture was extracted with ethyl acetate (3×). The combined organic layers were dried (Na$_2$SO$_4$) and concentrated. The crude product was dissolved in methanol and was purified over a SCX column (impurities washed with methanol; product eluted with 0.7N NH$_3$ in methanol to give the target compound (387 mg; yield: 92%).

Step 8 (is General Procedure A, Step 3)

4-(4-(4-(N-propylazetidin-3-yloxy)phenyl)-3-(2-chlorophenyl)isoxazol-5-yl)-phenol (compound 6g=7v=8d=9a)

To a solution of 4-(4-(4-(azetidin-3-yloxy)phenyl)-3-(2-chlorophenyl)isoxazol-5-yl)-phenol (630 mg, 1.504 mmol) and propionaldehyde (219 μl, 3.01 mmol) in methanol (50 ml) was added acetic acid (86 μl, 1.50 mmol) and sodium cyanoborohydride (189 mg, 3.01 mmol). The mixture was stirred at room temperature for 16 h and was then filtered and loaded onto a SCX column. The impurities were rinsed from the column by methanol and the product was eluted with 0.7N NH$_3$ in methanol. The obtained crude product was further purified by prep. HPLC (10 to 60% acetonitrile/water/3% TFA). To the product-containing fractions 2N HCl was added and the mixture was freeze dried to give the target compound as HCl salt as a white solid (174 mg, yield: 23%).

$^1$H-NMR (400 MHz, DMSO-D$_6$): δ 0.88 (t, 3H), 1.51 (m, 2H), 3.14 (t, br, 2H), 4.10 (m, br, 1H), 4.18 (m, br, 1H), 4.39 (m, br, 1H), 4.62 (m, br, 1H), 4.97 and 5.09 (2× m, br, 1H, azetidine H-3), 6.81 and 7.10 (2× d, AB system, 4H), 7.37-7.53 (m, 8H), 10.14 (s, br, 1H, OH), 10.54 and 10.68 (2× s, br, 1H; HCl).

A solution of compound 35 (1.0 mmol), compound 64 (2.0 mmol), $K_3PO_4 \cdot 7H_2O$ (3.0 mmol) and $PdCl_2(PPh_3)_2$ (0.05 mmol) in dioxane (10 ml) was stirred under $N_2$ atmosphere at 90° C. for 16 h. The reaction mixture was then cooled to room temperature. Water was added and the mixture was extracted with ethyl acetate (3×). The combined organic layers were washed with brine (1×), dried ($Na_2SO_4$) and concentrated. The crude product was purified by column chromatography to give compound 55 in good purity.

Compound 55 can be converted to compound 15 according to General Procedure A.

General Procedure G

Synthesis According to Scheme 6, Route B

Step 1

Under a nitrogen atmosphere 1-ethynyl-4-methoxybenzene (12 mmol) was dissolved in tetrahydrofuran (30 ml). The solution was cooled to −78° C. and n-butyl-lithium (1.6M in hexanes; 13 mmol) was added. The mixture was stirred at −40° C. and then a solution of compound 38 (11 mmol) in tetrahydrofuran (10 ml) was added. The mixture was stirred at room temperature for 1 h. Then water (50 ml) was added and the mixture was extracted with ethyl acetate (2×). The combined organic layers were dried ($Na_2SO_4$) and concentrated. The crude compound was triturated with diisopropylethylether (10 ml) to give compound 39 in good purity.

Step 2

Methoxylamine hydrochloride (45 mmol) was added at room temperature to a solution of sodium hydroxide (54 mmol) in ethanol (50 ml). The resulting suspension was stirred at room temperature for 1 h. Then $Na_2SO_4$ was added and the mixture was filtered. The filtrate was added dropwise to a cooled (0° C.) solution of sulfuric acid (4 ml) and compound 39 (9 mmol) in ethanol (5 ml) to give a very exothermic reaction. The mixture was stirred at 80° C. for 30 min. Then, water (100 ml) was added and the mixture was extracted with ethyl acetate (2×). The combined organic layers were dried ($Na_2SO_4$) and concentrated. The crude product contained both E and Z-isomer. Purification by prep. HPLC (acetonitrile/-water) afforded the desired Z-isomer of compound 40 in good purity.

Step 3

To a cooled (0° C.) solution of compound 40 (1.4 mmol) in methylene chloride (10 ml) was added iodine monochloride (2.1 mmol). The mixture was stirred at 0° C. for 1 h. Then, $NaS_2O_3$ and water were added and the mixture was extracted with methylene chloride (2×). The combined organic layers were dried ($Na_2SO_4$) and concentrated. The crude product was triturated from diisopropylethylether to afford compound 41 in good purity.

Compound 41 can be converted to compound 15 in several steps analogous to the conversion of compound 35 to compound 15 (according to General Procedure F, Step 5 and onwards).

General Procedure H

Synthesis According to Scheme 6, Route C

Step 1

Under a nitrogen atmosphere, to a solution of 4-fluorobenzoyl chloride (119 mmol) in triethylamine (660 ml) was added bis(triphenylphosphine)palladium(II) chloride (0.79 mmol) and copper(I) iodide (95 mmol). The mixture was stirred at room temperature for 30 min. Then, 1-ethynyl-4-methoxybenzene (79 mmol) was added to give an exothermic reaction. The mixture was stirred at room temperature for 16 h. The saturated aqueous $NH_4Cl$ solution was added and the mixture was extracted with ethyl acetate (3×). The combined organic layers were dried ($Na_2SO_4$) and concentrated. The crude product was purified by column chromatography over silica (heptane/ethyl acetate 9:1) to give compound 43 in good purity.

Step 2

Under a nitrogen atmosphere, to a solution of compound 43 (30 mmol) in toluene (100 ml) was added, at room temperature, (E)-2-chloro-N-hydroxybenzimidoyl chloride (38 mmol) and triethylamine (33 mmol). The mixture was stirred at 60° C. for 16 h. Then, water was added and the mixture was extracted with ethyl acetate (3×). The combined organic layers were dried ($Na_2SO_4$) and concentrated. The crude product was purified by column chromatography over silica to give compound 44 in good purity.

Compound 44 can be converted to compound 15 in several steps according to General Procedure B.

General Procedure I

Synthesis According to Scheme 6, Route D

Step 1

Compound 46 was prepared according to General procedure H, Step 1.

Step 2

Compound 47 was prepared according to General procedure H, Step 2.

Compound 47 can be converted to compound 15 in several steps according to General Procedure B.

2-(4-hydroxyphenyl)-3-(4-(1-methylazetidin-3-yloxy)phenyl)benzo[b]thiophen-6-ol 2,2,2-trifluoroacetate (compound 6a)

Synthesis according to General procedure C (Scheme 3)

2-(4-hydroxyphenyl)-3-(4-(1-propylazetidin-3-yloxy)phenyl)benzo[b]thiophen-6-ol 2,2,2-trifluoroacetate (compound 6b=7a=8a)

Synthesis according to General procedure A (Scheme 1)

2-(4-hydroxyphenyl)-3-(4-(1-propylazetidin-3-yloxy)phenoxy)benzo[b]thiophen-6-ol 2,2,2-trifluoroacetate (compound 6c=7c=8b)

Synthesis according to General procedure A (Scheme 1)
The title compound was obtained as white solid after freeze drying (106 mg; 62% yield).
$^1$H-NMR (400 MHz, DMSO) 0.87 (t, 3H), 1.48 (m, 2H), 3.12 (m, 2H), 4.10 (br m, 2H), 4.50 (br m, 2H), 4.95 (br m, 1H), 6.80 (m, 5H), 6.90 (d, 2H), 7.10 (d, 1H), 7.28 (d, 1H), 7.50 (d, 2H), 9.79 (s, 1H), 9.82 (s, 1H).

(6-hydroxy-2-(4-hydroxyphenyl)benzo[b]thiophen-3-yl)(4-(1-propylazetidin-3-yloxy)phenyl)methanone 2,2,2-trifluoroacetate (compound 6d=7h=8c)

Synthesis according to General procedure A (Scheme 1)

(6-hydroxy-2-(4-hydroxyphenyl)benzo[b]thiophen-3-yl)(4-(1-isopropylazetidin-3-yloxy)phenyl)methanone hydrochloride (compound 6e)

Synthesis according to General procedure A (Scheme 1)

4-(4-(4-(1-butylazetidin-3-yloxy)phenyl)-3-(2-chlorophenyl)isoxazol-5-yl)-phenol hydrochloride (compound 6h)

Synthesis according to General Procedure F (Scheme 6, route A)

4-(4-(4-(1-sec-butylazetidin-3-yloxy)phenyl)-3-(2-chlorophenyl)isoxazol-5-yl)-phenol hydrochloride (compound 6i)

Synthesis according to General procedure A (Scheme 1)

4-(4-(4-(1-propylazetidin-3-yloxy)phenyl)-3-o-tolylisoxazol-5-yl)phenol 2,2,2-trifluoroacetate (compound 6j)

Synthesis according to General procedure F (Scheme 6, route A)

4-(3-(2-chlorophenyl)-4-(4-(1-propylazetidin-3-yloxy)phenyl)isoxazol-5-yl)-3-methylphenol 2,2,2-trifluoroacetate (compound 6k)

Synthesis according to General procedure F (Scheme 6, route A)

4-(3-(2-chlorophenyl)-4-(4-(1-propylazetidin-3-yloxy)phenyl)isoxazol-5-yl)-2-methylphenol 2,2,2-trifluoroacetate (compound 6l)

Synthesis according to General procedure F (Scheme 6, route A)

(3-(2-chlorophenyl)-5-(4-hydroxyphenyl)isoxazol-4-yl)(4-(1-propylazetidin-3-yloxy)phenyl)methanone hydrochloride (compound 6m=7ag=8e)

Synthesis according to General procedure B (Scheme 2)

(5-(2-chlorophenyl)-3-(4-hydroxyphenyl)isoxazol-4-yl)(4-(1-propylazetidin-3-yloxy)phenyl)methanone (compound 6n=7ay)

Synthesis according to General procedure B (Scheme 2)

3-(4-((3S,4S)-7-methoxy-2,2-dimethyl-3-phenyl-chroman-4-yl)phenoxy)-1-propylazetidine 2,2,2-trifluoroacetate (compound 6o=7bd)

Synthesis according to General procedure A (Scheme 1)
Product was obtained as white solid after freeze drying (67.2 mg; 53% yield).
$^1$H-NMR (400 MHz, DMSO) 0.85 (t, 3H), 1.18 (s, 3H), 1.28 (s, 3H), 1.48 (m, 2H), 3.12 (t, 2H), 3.30 (d, 1H), 3.69 (s, 3H), 4.10 (br m, 2H), 4.49 (d, 1H), 4.60 (br m, 2H), 4.91 (br m, 1H), 6.32 (dd, 1H), 6.39 (m, 2H), 6.61 (br d, 1H), 7.05 (d, 2H), 7.12 (m, 1H), 7.20 (m, 2H), 7.31 (br m, 2H).

(3S,4S)-2,2-dimethyl-3-phenyl-4-(4-(1-propylazetidin-3-yloxy)phenyl)chroman-7-ol 2,2,2-trifluoroacetate (compound 6p=7be)

Synthesis according to General procedure A (Scheme 1)
Product was obtained as white solid after freeze drying (32.5 mg; 49% yield).
$^1$H-NMR (400 MHz, DMSO) 0.85 (t, 3H), 1.15 (s, 3H), 1.25 (s, 3H), 1.47 (m, 2H), 3.12 (t 2H), 3.28 (d, 1H), 4.10 (br m, 2H), 4.49 (d, 1H), 4.60 (br m, 2H), 4.92 (br m, 1H), 6.17 (dd, 1H), 6.19 (d, 1H), 6.29 (d, 1H), 6.61 (d, 2H), 7.02 (d, 2H), 7.12 (m, 1H), 7.19 (m, 2H), 7.30 (br m, 2H), 9.21 (s, 1H).

(5R,6S)-6-phenyl-5-(4-(1-propylazetidin-3-yloxy)phenyl)-5,6,7,8-tetrahydronaphthalen-2-ol hydrochloride (compound 6q=7bc=8j)

Synthesis according to General procedure A (Scheme 1)

7-hydroxy-3-phenyl-4-(4-(1-propylazetidin-3-yloxy)benzyl)-2H-chromen-2-one 2,2,2-trifluoroacetate (compound 6r)

Synthesis according to General procedure A (Scheme 1)
The title compound was obtained as white solid after freeze drying (55 mg; yield 60%).
$^1$H-NMR (400 MHz, CDCl$_3$) 1.00 (t, 3H), 1.69 (m, 2H), 3.11 (t, 2H), 3.75 (br m, 2H), 3.99 (s, 2H), 4.80 (br m, 2H), 5.12 (br m, 1H), 6.62 (d, 2H), 6.75 (d, 1H), 6.82 (d, 1H), 6.98 (d, 2H), 7.23 (d, 2H), 7.31 (d 1H), 7.38 (m, 3H).

(8S,11S,13S,14S,17S)-13-methyl-11-(4-(1-propylazetidin-3-yloxy)phenyl)-7,-8,9,10,11,12,13,14,15,16,17-decahydro-6H-cyclopenta[a]phenanthrene-3,17-diol (compound 6s)

Synthesis according to General procedure A (Scheme 1)

(8S,11S,13S,14S,17S)-11-(4-(1-(cyclopropylmethyl)azetidin-3-yloxy)phenyl)-13-methyl-7,8,9,10,11,12,13,14,15,16,17-decahydro-6H-cyclopenta[a]phenanthrene-3,17-diol (compound 6t)

Synthesis according to General procedure A (Scheme 1)

3-(4-(1,2-diphenylbut-1-enyl)phenoxy)-1-propylazetidine 2,2,2-trifluoroacetate (compound 6u=7bg=8k=9g)

Synthesis according to General procedure A (Scheme 1)

The title compound was obtained as colorless oil (126 mg; 46% yield).

$^1$H-NMR (400 MHz, DMSO) 0.80-0.94 (m, 12H), 1.50 (m, 4H), 2.40 (m 4H), 3.12, 3.19 2× (br t, 2H), 4.00-4.30 (br m, 4H), 4.30-4.75 (br m, 4H), 4.82-5.17 2× (br m, 2H), 6.55 (br m, 2H), 6.75-6.93 (m, 6H), 6.95-7.07 (m, 3H), 7.07-7.25 (m, 14H), 7.30 (m, 1H), 7.40 (m, 2H).

(E/Z)-4-(2-phenyl-1-(4-(1-propylazetidin-3-yloxy)phenyl)but-1-enyl)phenol 2,-2,2-trifluoroacetate (compound 6v=7bh)

Synthesis according to General procedure A (Scheme 1)

The title compound was obtained as white solid after freeze drying (117 mg; 58% yield).

$^1$H-NMR (400 MHz, DMSO) 0.87 4× (t, 3H), 1.48 2× (m, 2H), 2.40 2× (m 2H), 3.13 2× (t, 2H), 4.10 2× (br m, 2H), 4.50 2× (br m, 2H), 4.90, 5.09 2× (br m, 1H), 6.40 (d, 2H), 6.53 (d, 2H), 6.60 (d, 2H), 6.77 (d, 4H), 6.88 (d, 2H), 6.98 (d, 2H), 7.07-7.21 (m, 12H), 9.21 (s, 1H), 9.46 (s, 1H).

(E/Z)-3-(2-phenyl-1-(4-(1-propylazetidin-3-yloxy)phenyl)but-1-enyl)phenol (compound 6w=7bi=9h)

Synthesis according to General procedure A (Scheme 1)

The title compound was obtained as white solid after freeze drying (107 mg; 64% yield).

$^1$H-NMR (400 MHz, DMSO) 0.85 4× (t, 3H), 1.45 2× (m, 2H), 2.38 2× (m 2H), 3.15 2× (t, 2H), 4.15 2× (br m, 2H), 4.60 2× (br m, 2H), 5.01 2× (br m, 1H), 6.25 (m, 2H), 6.39 (d, 1H), 6.55 (m, 3H), 6.62 (d, 1H), 6.69 (d, 1H), 6.80 (m, 3H), 6.89 (br d, 2H), 7.08-7.22 (m, 13H), 9.09 (s, 1H), 9.42 (s, 1H).

(E/Z)-3-(4-(2-chloro-1,2-diphenylvinyl)phenoxy)-1-propylazetidine 2,2,2-trifluoroacetate (compound 6x=7bj)

Synthesis according to General procedure A (Scheme 1)

The title compound was obtained as white solid after freeze drying (60 mg; 46% yield).

$^1$H-NMR (400 MHz, DMSO) 0.88 2× (t, 3H), 1.45 2× (m, 2H), 3.15 2× (t, 2H), 4.15 2× (br m, 2H), 4.60 2× (br m, 2H), 5.01 2× (br m, 1H), 6.65 (d, 2H), 6.90 (d, 4H), 6.96 (m, 2H), 7.15 (m, 4H), 7.20-7.38 (m, 14H), 7.42 (m, 2H).

3-(4-(1-allylazetidin-3-yloxy)phenyl)-2-(4-hydroxyphenyl)benzo[b]thiophen-6-ol 2,2,2-trifluoroacetate (compound 7b)

Synthesis according to General procedure C (Scheme 3)

(6-hydroxy-2-(4-hydroxyphenyl)benzo[b]thiophen-3-yl)(4-(1-methylazetidin-3-yloxy)phenyl)methanone hydrochloride (compound 7d)

Synthesis according to General procedure A (Scheme 1)

(6-hydroxy-2-phenylbenzo[b]thiophen-3-yl)(4-(1-propylazetidin-3-yloxy)-phenyl)methanone hydrochloride (compound 7e)

Synthesis according to General Procedure E (Scheme 5, route C)

(6-hydroxy-2-(thiophen-2-yl)benzo[b]thiophen-3-yl)(4-(1-propylazetidin-3-yl-oxy)phenyl)methanone hydrochloride (compound 7f)

Synthesis according to General Procedure E (Scheme 5, route C)

(4-(1-ethylazetidin-3-yloxy)phenyl)(6-hydroxy-2-(4-hydroxyphenyl)benzo[b]-thiophen-3-yl)methanone 2,2,2-trifluoroacetate (compound 7g)

Synthesis according to General Procedure E (Scheme 5, route C)

(4-(1-cyclopropylazetidin-3-yloxy)phenyl)(6-hydroxy-2-(4-hydroxyphenyl)-benzo[b]thiophen-3-yl)methanone 2,2,2-trifluoroacetate (compound 7i)

Synthesis according to General procedure C (Scheme 3)

(4-(1-(3-fluoropropyl)azetidin-3-yloxy)phenyl)(6-hydroxy-2-(4-hydroxyphenyl)benzo[b]thiophen-3-yl)methanone 2,2,2-trifluoroacetate (compound 7j)

Synthesis according to General procedure A (Scheme 1)

(6-hydroxy-2-(4-hydroxyphenyl)benzo[b]thiophen-3-yl)(4-(1-(3-methoxypropyl)azetidin-3-yloxy)phenyl)methanone 2,2,2-trifluoroacetate (compound 7k)

Synthesis according to General procedure C (Scheme 3)

(4-(1-cyclobutylazetidin-3-yloxy)phenyl)(6-hydroxy-2-(4-hydroxyphenyl)-benzo[b]thiophen-3-yl)methanone hydrochloride (compound 7l)

Synthesis according to General procedure A (Scheme 1)

(6-hydroxy-2-(4-hydroxyphenyl)benzo[b]thiophen-3-yl)(4-(1-isobutylazetidin-3-yloxy)phenyl)methanone hydrochloride (compound 7m)

Synthesis according to General procedure C (Scheme 3)

(4-(1-(cyclobutylmethyl)azetidin-3-yloxy)phenyl)(6-hydroxy-2-(4-hydroxyphenyl)benzo[b]thiophen-3-yl)methanone hydrochloride (compound 7n)

Synthesis according to General procedure C (Scheme 3)

(6-hydroxy-2-(4-hydroxyphenyl)benzo[b]thiophen-3-yl)(4-(1-((tetrahydrofuran-3-yl)methyl)azetidin-3-yloxy)phenyl)methanone hydrochloride (compound 7o)

Synthesis according to General procedure C (Scheme 3)

(6-hydroxy-2-(4-hydroxyphenyl)benzo[b]thiophen-3-yl)(4-(1-(3,3,3-trifluoropropyl)azetidin-3-yloxy)phenyl)methanone hydrochloride (compound 7p)

Synthesis according to General procedure A (Scheme 1)

(6-hydroxy-2-(4-hydroxy-2-methylphenyl)benzo[b]thiophen-3-yl)(4-(1-propylazetidin-3-yloxy)phenyl)methanone hydrochloride (compound 7q)

Synthesis according to General Procedure E (Scheme 5, route C)

(6-hydroxy-2-(4-hydroxy-3-methylphenyl)benzo[b]thiophen-3-yl)(4-(1-propylazetidin-3-yloxy)phenyl)methanone hydrochloride (compound 7r)

Synthesis according to General Procedure E (Scheme 5, route C)

(2-(4-fluoro-3-methylphenyl)-6-hydroxybenzo[b]thiophen-3-yl)(4-(1-propylazetidin-3-yloxy)phenyl)methanone hydrochloride (compound 7s)

Synthesis according to General Procedure E (Scheme 5, route C)

(2-(3,5-difluorophenyl)-6-hydroxybenzo[b]thiophen-3-yl)(4-(1-propylazetidin-3-yloxy)phenyl)methanone hydrochloride (compound 7t)

Synthesis according to General Procedure E (Scheme 5, route C)

(3-fluoro-4-(1-propylazetidin-3-yloxy)phenyl)(6-hydroxy-2-(4-hydroxyphenyl)-benzo[b]thiophen-3-yl)methanone hydrochloride (compound 7u)

Synthesis according to General Procedure E (Scheme 5, route C)

4-(3-(2-chlorophenyl)-4-(4-(1-isobutylazetidin-3-yloxy)phenyl)isoxazol-5-yl)-phenol hydrochloride (compound 7w=9b)

Synthesis according to General procedure A (Scheme 1)

4-(3-(2-chlorophenyl)-4-(4-(1-((tetrahydrofuran-3-yl)methyl)azetidin-3-yloxy)-phenyl)isoxazol-5-yl) phenol hydrochloride (compound 7x)

Synthesis according to General procedure A (Scheme 1)

4-(3-(2-chlorophenyl)-4-(4-(1-(cyclopropylmethyl)azetidin-3-yloxy)phenyl)-isoxazol-5-yl)phenol hydrochloride (compound 7y=9c)

Synthesis according to General procedure A (Scheme 1)

4-(3-(2-chlorophenyl)-4-(4-(1-(cyclobutylmethyl)azetidin-3-yloxy)phenyl)-isoxazol-5-yl)phenol hydrochloride (compound 7z=9d)

Synthesis according to General procedure A (Scheme 1)

4-(3-(2-chlorophenyl)-4-(4-(1-(3-fluoropropyl)azetidin-3-yloxy)phenyl)isoxazol-5-yl)phenol hydrochloride (compound 7aa=9e)

Synthesis according to General procedure A (Scheme 1)

4-(3-(2-chloro-6-methylphenyl)-4-(4-(1-propylazetidin-3-yloxy)phenyl)isoxazol-5-yl)phenol 2,2,2-trifluoroacetate (compound 7ab)

Synthesis according to General procedure F (Scheme 6, route A)

4-(3-(2,3-dimethylphenyl)-4-(4-(1-propylazetidin-3-yloxy)phenyl)isoxazol-5-yl)phenol 2,2,2-trifluoroacetate (compound 7ac)

Synthesis according to General procedure F (Scheme 6, route A)

4-(3-(2-ethylphenyl)-4-(4-(1-propylazetidin-3-yloxy)phenyl)isoxazol-5-yl)-phenol 2,2,2-trifluoroacetate (compound 7ad)

Synthesis according to General procedure F (Scheme 6, route A)

4-(3-(4-methyl-1,2,3-thiadiazol-5-yl)-4-(4-(1-propylazetidin-3-yloxy)phenyl)isoxazol-5-yl)phenol hydrochloride (compound 7ae)

Synthesis according to General Procedure G (Scheme 6, route B)

4-(3',5'-dimethyl-4-(4-(1-propylazetidin-3-yloxy)phenyl)-3,4'-biisoxazol-5-yl)-phenol hydrochloride (compound 7af)

Synthesis according to General Procedure G (Scheme 6, route B)

(3-(2-chlorophenyl)-5-(4-hydroxyphenyl)isoxazol-4-yl)(4-(1-(-(3-fluoropropyl)azetidin-3-yloxy)phenyl)methanone 2,2,2-trifluoroacetate (compound 7ah=8f)

Synthesis according to General procedure C (Scheme 3)

(5-(4-hydroxyphenyl)-3-phenylisoxazol-4-yl)(4-(1-propylazetidin-3-yloxy)-phenyl)methanone hydrochloride (compound 7ai)

Synthesis according to General procedure B (Scheme 2)

(5-(4-hydroxyphenyl)-3-o-tolylisoxazol-4-yl)(4-(1-propylazetidin-3-yloxy)-phenyl)methanone hydrochloride (compound 7aj)

Synthesis according to General procedure B (Scheme 2)

(3-(2,6-difluorophenyl)-5-(4-hydroxyphenyl)isoxazol-4-yl)(4-(1-propylazetidin-3-yloxy)phenyl)methanone hydrochloride (compound 7ak=8g)

Synthesis according to General procedure B (Scheme 2)

(5-(4-hydroxyphenyl)-3-(1-methyl-1H-pyrrol-2-yl)
isoxazol-4-yl)(4-(1-propylazetidin-3-yloxy)phenyl)
methanone hydrochloride (compound 7am)

Synthesis according to General procedure B (Scheme 2)

(5-(4-hydroxyphenyl)-3-(3-methylpyridin-2-yl)isox-
azol-4-yl)(4-(1-propylazetidin-3-yloxy)phenyl)
methanone hydrochloride (compound 7am)

Synthesis according to General procedure B (Scheme 2)

(5-(4-hydroxyphenyl)-3-(3-methylthiophen-2-yl)
isoxazol-4-yl)(4-(1-propylazetidin-3-yloxy)phenyl)
methanone hydrochloride (compound 7an)

Synthesis according to General procedure B (Scheme 2)

(3-(2-chlorophenyl)-5-phenyl)isoxazol-4-yl)(4-(1-
propylazetidin-3-yloxy)-phenyl)methanone hydro-
chloride (compound 7ao)

Synthesis according to General procedure B (Scheme 2)

(3-(2-chlorophenyl)-5-(3-hydroxyphenyl)isoxazol-4-
yl)(4-(1-propylazetidin-3-yloxy)phenyl)methanone
hydrochloride (compound 7ap)

Synthesis according to General procedure B (Scheme 2)

(3-(2-chlorophenyl)-5-(1H-pyrrol-3-yl)isoxazol-4-yl)
(4-(1-propylazetidin-3-yl-oxy)phenyl)methanone
2,2,2-trifluoroacetate (compound 7aq)

Synthesis according to General procedure B (Scheme 2)

(5-(4-aminophenyl)-3-(2-chlorophenyl)isoxazol-4-
yl)(4-(1-propylazetidin-3-yl-oxy)phenyl)methanone
2,2,2-trifluoroacetate (compound 7ar)

Synthesis according to General procedure B (Scheme 2)

(3-(2-chlorophenyl)-5-(1H-indazol-4-yl)isoxazol-4-
yl)(4-(1-propylazetidin-3-yl-oxy)phenyl)methanone
2,2,2-trifluoroacetate (compound 7as)

Synthesis according to General procedure B (Scheme 2)

(3-(2-chlorophenyl)-5-(4-hydroxyphenyl)isoxazol-4-
yl)(3-fluoro-4-(1-propylazetidin-3-yloxy)phenyl)
methanone hydrochloride (compound 7at)

Synthesis according to General procedure B (Scheme 2)

4-(3-(2-chlorophenyl)-4-(4-(1-propylazetidin-3-
yloxy)phenyl)isoxazol-5-yl)-phenol hydrochloride
(compound 7au)

Synthesis according to Scheme 7

To a solution of 4-(3-(2-chlorophenyl)-4-(hydroxy(4-(1-propylazetidin-3-yloxy)-phenyl)methyl)isoxazol-5-yl)phenol (79 mg, 0.161 mmol) in methylene chloride (5 ml) was added triethylsilane (39 μl, 0.241 mmol). The reaction mixture was cooled to 0° C. and trifluoroacetic acid (1.195 ml, 16.1 mmol) was added. The mixture was stirred at room temperature for 2 h. Then water and saturated NaHCO₃ solution were added. The mixture was extracted with ethyl acetate. The combined organic layers were dried (Na₂SO₄) and concentrated. The crude product was purified by prep. HPLC (10-60% acetonitrile/water+3% TFA). To the product-containing fractions 4N HCl (0.5 ml) was added and the mixture was freeze-dried to give the target compound as a white solid (60 mg, 70% yield).

4-(3-(2-chlorophenyl)-4-(hydroxy(4-(1-propylazeti-
din-3-yloxy)phenyl)methyl)isoxazol-5-yl)phenol
(compound 7av=9f)

Synthesis according to Scheme 7

To a solution of (3-(2-chlorophenyl)-5-(4-hydroxyphenyl) isoxazol-4-yl)(4-(1-propylazetidin-3-yloxy)phenyl)methanone (100 mg, 0.190 mmol) in ethanol was added sodium borohydride (144 mg, 3.81 mmol). The reaction mixture was stirred at reflux for 48 h. Then water was added and the mixture was extracted with ethyl acetate. The combined organic layers were dried (Na₂SO₄) and concentrated. The crude product was purified by column chromatography over silica (elution with methylene chloride/methanol/triethylamine 95:5:0.1) to give the desired product as free base (60 mg, 43% yield)

4-(3-(2-chlorophenyl)-4-(methoxy(4-(1-propylazeti-
din-3-yloxy)phenyl)methyl)-isoxazol-5-yl)phenol
(compound 7aw)

Synthesis according to Scheme 7

To a solution of 4-(3-(2-chlorophenyl)-4-(4-(1-propylazetidin-3-yloxy)phenyl)isoxazol-5-yl)phenol (35 mg, 0.071 mmol) in acetonitrile (3 ml) was added hydrogen chloride (0.71 mmol) and methanol (2 ml). The mixture was stirred at room temperature for 16 h. Then NaHCO₃ was added and the mixture was extracted with ethyl acetate. The combined organic layers were dried (Na₂SO₄) and concentrated. The crude product was purified by column chromatography over silica (elution with methylene chloride/methanol/ammonia 95:5:0.1). The product-containing fractions were concentrated, redissolved in acetonitrile/water and freeze-dried to give the desired compound as a white solid (20 mg, 48% yield).

4-(3-(2-chlorophenyl)-4-(1-(4-(1-propylazetidin-3-
yloxy)phenyl)vinyl)isoxazol-5-yl)phenol (compound
7ax)

Synthesis according to Scheme 7

To a cooled (0° C.) solution of (3-(2-chlorophenyl)-5-(4-hydroxyphenyl)isoxazol-4-yl)(4-(1-propylazetidin-3-yloxy)phenyl)methanone (76 mg, 0.155 mmol) in anhydrous THF (2 ml), under a nitrogen atmosphere, was added methyllithium (0.971 ml, 1.554 mmol). The mixture was stirred for 2 h at room temperature. Then water was added and the mixture was extracted with ethyl acetate. The combined organic layers were dried (Na₂SO₄) and concentrated. The crude product was purified by column chromatography over silica (elution with methylene chloride/-methanol/ammonia 95:5:0.1). The obtained intermediate (50 mg) was dissolved in acetonitrile (2 ml) and a few drops of concentrated HCl were added. The mixture was stirred at room temperature for 2 h. Then NaHCO₃ was added and the mixture was extracted with ethyl acetate. The combined organic layers were dried (Na₂SO₄) and concentrated. The crude product was purified by column chromatography over silica (elution with methylene chloride/methanol/ammonia 95:5:0.1). The purified product was dissolved in acetonitrile/water and was freeze-dried to give the desired product as a white solid (39 mg, 38% yield).

(3-(4-hydroxyphenyl)-5-o-tolylisoxazol-4-yl)(4-(1-propylazetidin-3-yloxy)-phenyl)methanone hydrochloride (compound 7az=8h)

Synthesis according to General procedure B (Scheme 2)

(5-(2-fluorophenyl)-3-(3-hydroxyphenyl)isoxazol-4-yl)(4-(1-propylazetidin-3-yloxy)phenyl)methanone hydrochloride (compound 7ba)

Synthesis according to Scheme 6, route D (5-(4-hydroxyphenyl)-3-o-tolylisothiazol-4-yl)(4-(1-propylazetidin-3-yloxy)-phenyl)methanone hydrochloride (compound 7bb)

Synthesis according to Scheme 8

7-methoxy-3-phenyl-4-(4-(1-propylazetidin-3-yloxy) benzyl)-2H-chromen-2-one (compound 7bf)

Synthesis according to General procedure A (Scheme 1)
The title compound was obtained as white solid (75 mg; 85% yield).
$^1$H-NMR (400 MHz, CDCl$_3$) 0.90 (t, 3H), 1.39 (m, 2H), 2.46 (t, 2H), 3.03 (m, 2H), 3.80 (m, 2H), 3.88 (s, 3H), 3.99 (s 2H), 4.72 (m, 1H), 6.62 (d, 2H), 6.75 (d, 1H), 6.82 (d, 1H), 6.98 (d, 2H), 7.23 (d, 2H), 7.31 (d 1H), 7.38 (m, 3H).

Example 11

The antagonistic activity of compounds on the estrogen receptors was determined in an in vitro bioassay with recombinant Chinese Hamster Ovary (CHO) cells stably co-transfected with the human estrogen receptor α (hERα), the rat oxytocin promoter (RO) and the luciferase reporter gene (LUC). The potency of a test compound to antagonize the transactivation of the enzyme luciferase by 17β-estradiol and mediated via the estrogen receptors hERα is expressed as IC50 in mol/l and/or as pIC50 (−log(IC50)) and/or as percentage (%) relative to the IC50 of the standard anti-estrogen ICI 164.384 (potency test compound=(IC50 ICI 164,384/IC50 test compound)×100%). The antagonistic efficacy, i.e. the amount of maximal inhibition of the 17β-estradiol activated receptor by a compound, is expressed as fraction relative to the maximal inhibition as induced by the standard anti-estrogen ICI 164,384 (efficacy test compound= (maximal inhibition test compound/maximal inhibition ICI 164,384)). A more detailed description of the methodology can be found in De Gooyer et al., Steroids, 68 (2003) 21-30.

In certain embodiments, compounds of the present invention are antagonistic at ERα with a pIC50>7.

Example 12

To what extent compounds are capable of stimulating proliferation in ER-positive, tamoxifen-resistant breast cancer cells is tested in a 7-day in vitro proliferation assay using MCF-7H cells. More specifically, this in vitro bioassay is used to determine the efficacy (fraction of maximal response), pEC50, and relative potency of the compound to induce proliferation by comparing the data for this compound with those of the reference compound 17β-estradiol (E2) in the same test.

A more detailed description of the method used is as follows.

Cell culture: The human epithelial breast cancer cell line MCF-7H (origin: Hubrecht Laboratory, Utrecht, The Netherlands) was routinely maintained in complete medium which is a 1:1 mixture of Ham's F12 medium and Dulbecco's Modified Eagle Medium (DMEM; Invitrogen, Carlsbad, USA) without phenol red and enriched with 5% fetal calf serum (FCS; Hyclone, Utah, USA), 100 µg/ml streptomycin and 100 units/ml penicillin adapted to contain:

SOD DIHYD PHOS 2H20 EP 0.0706618 g/L
DISOD HYD PHOS ANHYD EP 0.07102 g/L
CUPRIC SULPH ANHYD 0.0008 g/L
L-GLUTAMINE 1.085 g/L
D-BIOTIN EP+ 0.0000037 g/L
SODIUM PYRUVATE 0.165 g/L
SOD SELENITE 5H20 0.000447 g/L
MERCAPTOETHANOL 0.0023 g/L
ETHANOLAMINE HCL 0.00198 g/L
BOVINE INSULIN 0.0005 g/L

Cells were grown in 80 cm$^2$ culture flasks (Nunc, Roskilde, Denmark) and kept in an atmosphere of 5% CO$_2$-95% air at 37 degrees Celsius. Cells were subcultured when they reached about 80-90% confluence, resulting in one passage a week. Subculturing includes detaching the cells using trypsin/EDTA and diluting the cell suspension 10 times.

Methyl-$^3$H-thymidine incorporation assay: MCF-7H cells were starved overnight in assay medium containing 5% charcoal-treated (CT) bovine calf serum (BCS; Hyclone) instead of FCS and a final concentration of 1.0 µg/ml bovine insulin, the day before plating. Cells were plated in assay medium containing 5% CT BCS, in white 24-wells plates (Perkin Elmer, Shelton, USA), at a density of 7.5×10$^3$ cells per well, each well containing 630 µL assay medium. Cells were allowed to attach and spread for 24 h before stimulation with reference and/or test compound(s). After a stimulation period of 7 days, 0.25 µCi/well of methyl-$^3$H-thymidine (GE Healthcare Limited, Buckinghamshire, UK) was added per well. Cultures were maintained in an atmosphere of 5% CO$_2$-95% air at 37 degrees Celsius. After overnight incubation, excess methyl-$^3$H-thymidine was aspirated and the cells were washed with phosphate-buffered saline (PBS). After 1 h of incubation with 1 ml scintillation fluid Microscint-20 (Perkin Elmer), radioactivity was measured in a Packard TOP-count NXT microplate scintillation counter (Perkin Elmer). 17β-Estradiol (E2) and Ethynyl Estradiol (EE) induce proliferation of MCF-7H breast cancer cells in the picomolar range and with full efficacy (efficacy of E2 is 1.0 by definition; data for selected compounds are given in Table 1).

TABLE 1

In vitro data for selected reference compounds in MCF-7H breast cancer cell proliferation assay

| Compound | % E2 | Efficacy (fractional to E2) |
| --- | --- | --- |
| E2 | 100 [a] | 1.00 [a] |
| EE | 137 | 0.99 |
| Tamoxifen | 0.008 | 0.58 |
| 4OHT[b] | 2.3 | 0.49 |
| Raloxifene | 21.1 | 0.33 |
| Arzoxifene | 99.1 | 0.34 |

TABLE 1-continued

In vitro data for selected reference compounds in MCF-7H breast cancer cell proliferation assay

| Compound | % E2 | Efficacy (fractional to E2) |
|---|---|---|
| Droloxifene | 5.9 | 0.38 |
| Fulvestrant | 18.9 | 0.02 |

[a] per definition; data for test compounds are normalized against those for E2
[b] 4-OH-tamoxifen is a potent pharmacologically active metabolite of tamoxifen In certain embodiments, compounds of the present invention show an efficacy equal to or <0.10 in the MCF-7H breast cancer cell proliferation assay.

Example 13

To what extent compounds are capable of stabilizing or downregulating (destabilizing) the estrogen receptor alpha in ER-positive breast cancer cells is tested in an in vitro assay using T47D cells. More specifically, this in vitro bioassay is used to determine the efficacy (fraction of maximal response) of the compound by comparing the data for this compound with those of the reference compound ICI 182,780 (fulvestrant) in the same test (downregulation of fulvestrant is 100% by definition). 4-OH-Tamoxifen is included as an example of a compound that stabilizes ERα protein levels in the cell (data for selected compounds are given in Table 2).

A more detailed description of the method used is as follows.

Cell culture. The human epithelial breast cancer cell line T47D (origin: ATCC) was routinely maintained in a 1:1 mixture of Ham's F12 medium and Dulbecco's Modified Eagle Medium (Gibco) enriched with 5% fetal calf serum (Hyclone), 10 mM HEPES pH 7.5 and 100 µg/ml penicillin-streptomycin solution. Cells were grown in 80 cm2 culture flasks (Nunc, Roskilde, Denmark) and kept in an atmosphere of 5% $CO_2$-95% air at 37 degrees Celsius. Cells were subcultured when they reached about 80-90% confluence, resulting in one passage a week. Subculturing includes detaching the cells using Cell Dissociation Buffer [Sigma] and subsequent inoculation at 1:5 or 1:10 in a new Roux flask (175 cc) and\or plating out in Nunclon™ Surface 96 wells microplates. The culture medium needs to be refreshed on day three or four of the incubation, if applicable.

Determination of ERα protein levels: T47D cells in the microplates are incubated with 1E-5 M test compound for 24 hours. The supernatant in all wells is carefully aspirated. Cells are lysed on the microplate and cell lysates are probed for ERα content using an ERα ELISA assay kit (Active Motif).

TABLE 2

In vitro data for selected reference compounds in the ERα downregulation assay in T47D breast cancer cells

| Compound | Downregulation (% of fulvestrant) |
|---|---|
| Fulvestrant | 100 [a] |
| 4OHT [b] | −330 [c] |
| Raloxifene | −39 [c] |
| Vehicle (1% DMSO) | 0 [d] |

[a] per definition; data for test compounds are normalized against those for fulvestrant
[b] 4-OH-tamoxifen is a potent pharmacologically active metabolite of tamoxifen
[c] a negative number indicates upregulation or stabilization of the receptor
[d] compound-induced effects are normalized against a vehicle control In certain embodiments, compounds of the present invention show a minimum of 20% downregulation of ERα in the T47D breast cancer cell assay.

Example 14

Rapid Rat PK

This test was used to determine the pharmacokinetic parameters (AUC(0-6h), Cmax and Tmax) after oral administration of compounds in male (intact or castrated) or female (intact or ovariectomized) rats (*Rattus Norvegicus*).

After oral administration of a compound at 20 µmol/kg, blood was collected at various time points (0.5, 1, 2, 3, 4 and 6 hours after compound administration) via the tail vein. Plasma samples were pooled per time point, after which the concentration was determined in plasma by means of LC-MS. Pharmacokinetic parameters (AUC(0-6h), Cmax and Tmax) were derived from the obtained concentration versus time curves using the non-compartmental analysis module in Animals! or WinNonlin.

In certain embodiments, compounds of the present invention are orally bioavailable in the rat with an AUC(0-6h)>1 µM·h.

TABLE 3

Biological and physicochemical data of cpds. according to Formulae 6

| compound | ERα pIC50 [a] | yield (%) | purity (%) | HPLC Rf (min) | HPLC method | MS-ESI [M + H] | azetidine NMR H-3 ppm |
|---|---|---|---|---|---|---|---|
| 6a | 9.1 | 17 | 95.7 | 2.07 | A | 404.1 | 5.12 (m, br) (MeOD) |
| 6b | 9.1 | 44 | 98 | 14.83 | E | 432.2 | 5.05, 5.15 (2xm, br) (DMSO) |
| 6c | 9.6 | 62 | 98 | 2.19 | A | 448.1 | 4.95 (m, br) (DMSO) |
| 6d | 8.8 | 19 | 99 | 2.13 | A | 460 | 5.05, 5.15 (2xm, br) (DMSO) |
| 6e | 8.8 | 24 | 99 | 2.05 | A | 460 | |
| 6f | 7.8 | 82 | 89.4 | 5.49 | D | | 5.12 (m) (MeOD) |
| 6g | 9.6 | 23 | 99.8 | 2.67 | A | 461.1 | 4.97, 5.09 (2xm, br) (DMSO) |
| 6h | 9.2 | 50 | 99.7 | 2.78 | A | 475.2 | 4.96, 5.08 (2xm, br) (DMSO) |
| 6i | 9.0 | 35 | 99.4 | 2.69 | A | 475.2 | 4.70 (m) (MeOD) |
| 6j | 9.4 | 32 | 100 | 0.93 | B | | 4.65, 5.05 (2xm, br) (DMSO) |
| 6k | 9.3 | 15 | 99 | 0.96 | B | | 4.94, 5.04 (2xm, br) (DMSO) |
| 6l | 9.2 | 16 | 100 | 1.08 | B | | 4.98, 5.08 (2xm, br) (DMSO) |
| 6m | 8.7 | 61 | 97.7 | 2.60 | A | 489.2 | 5.05, 5.15 (2xm, br) (DMSO) |
| 6n | 8.4 | 39 | 98.8 | 0.84 | B | 489.3 | 4.8 (m, br) (DMSO) |
| 6o | 7.6 | 53 | 100 | 2.79 | B | 458.19 | 4.91 (m, br) (DMSO) |
| 6p | 8.4 | 49 | 99 | 2.46 | B | 444.20 | 4.92 (m, br) (DMSO) |
| 6q | 9.6 | 46 | 98 | 0.93 | B | 414.3 | 4.85, 4.95 (2xm, br) (DMSO) |

TABLE 3-continued

Biological and physicochemical data of cpds. according to Formulae 6

| compound | ERα pIC50 [a] | yield (%) | purity (%) | HPLC Rf (min) | HPLC method | MS-ESI [M + H] | azetidine NMR H-3 ppm |
|---|---|---|---|---|---|---|---|
| 6r | 8.8 | 60 | 98 | 2.43 | A | 442.3 | 5.12 (m, br) (DMSO) |
| 6s | 8.6 | 42 | 95 | 2.75 | C | 460.1 | 4.70 (m) (CDCl$_3$) |
| 6t | 8.5 | 78 | 98 | 2.69 | C | 474.1 | 4.90 (m) (CDCl$_3$) |
| 6u | 7.5 | 46 | 93 | 1.82, 1.99 | C | 398.22 | 4.82-5.17 (4xm, br) (DMSO) |
| 6v | 9.3 | 58 | 97 | 2.66 | C | 414.19 | 4.90, 5.09 (2xm, br) (DMSO) |
| 6w | 8.3 | 64 | 97 | 1.49, 1.58 | B | 414.4 | 5.01 (2xm, br) (DMSO) |
| 6x | 8.1 | 46 | 100 | 1.53, 1.58 | B | 404.1 | 5.01 (m, br) (DMSO) |

[a] See Example 11
A: UPLC BEH C18, 1.7 um, 2.1x100 mm (0 to 60% acetonitrile/water/5% TFA)
B: UPLC BEH C18, 1.7 um, 2.1x100 mm (40 to 80% acetonitrile/water/5% TFA)
C: LCMS Xbridge, C18, 3.5 um, 3.5x20 mm (0 to 100% acetonitrile/water/5% TFA)
D: Luna C18, 3 um, 100x2 mm (25% acetonitrile/75% water)
E: Luna C18, 3 um, 100x2 mm (0-80% acetonitrile/5% TFA)

TABLE 4

Biological and physicochemical data of cpds. according to Formulae 7

| cpd | ERα pIC50 [a] | DR (%) [b] | yield (%) | purity (%) | HPLC Rf (min) | HPLC method | MS-ESI [M + H] | azetidine NMR H-3 ppm |
|---|---|---|---|---|---|---|---|---|
| 7a | 9.1 | 53 | 44 | 98 | 14.83 | E | 432.2 | 5.05, 5.15 (2xm, br) (DMSO) |
| 7b | 9.2 | 68 | 21 | 99.3 | 2.20 | A | 430.1 | 4.98 (m, br) (MeOD) |
| 7c | 9.6 | 7 [c] | 62 | 98 | 2.19 | A | 448.1 | 4.95 (m, br) (DMSO) |
| 7d | 8.7 | 48 | 18 | 97.2 | 1.91 | A | 432 | 5.10 (m, br) (DMSO) |
| 7e | 8.7 | 96 | 34 | 99.3 | 10.80 | F | 444 | 5.2 (m, br) (MeOD) |
| 7f | 8.6 | 88 | 60 | 98.2 | 0.67 | B | 450 | 5.16 (m, br) (MeOD) |
| 7g | 8.4 | 46 | 26 | 99 | 11.88 | G | | 5.06, 5.12 (2xm, br) (DMSO) |
| 7h | 8.8 | 79 | 19 | 99 | 2.13 | A | 460 | 5.05, 5.15 (2xm, br) (DMSO) |
| 7i | 8.6 | 66 | 62 | 98.8 | 2.07 | A | 458 | 5.09 (2xm, br) (DMSO) |
| 7j | 8.6 | 98 | 2 | 98.8 | 2.07 | A | 478 | 5.13 (m, br) (DMSO) |
| 7k | 8.7 | 57 | 14 | 94.4 | 2.12 | A | 490 | 5.05, 5.14 (2xm, br) (DMSO) |
| 7l | 9.1 | 30 | 15 | 99.4 | 2.07 | A | 472 | 5.09 (m, br) (DMSO) |
| 7m | 9.0 | 73 | 24 | 99.3 | 2.24 | A | 474 | 5.11 (m, br) (MeOD) |
| 7n | 8.9 | 77 | 36 | 99.6 | 2.28 | A | 486 | 5.11 (m, br) (MeOD) |
| 7o | 8.3 | 73 | 39 | 96.4 | 1.98 | A | 502 | 5.14 (m, br) (MeOD) |
| 7p | 8.3 | 35 | 14 | 95.1 | 2.21 | A | 514 | |
| 7q | 8.9 | 64 | 14 | 91.7 | 8.71 | G | | 5.12 (m, br) (MeOD) |
| 7r | 8.7 | 94 | 14 | 99.2 | 9.64 | F | | 5.09 (m, br) (MeOD) |
| 7s | 8.3 | 101 | 25 | 98.9 | 10.90 | F | | 5.13 (m, br) (MeOD) |
| 7t | 8.7 | 98 | 27 | 97 | 10.82 | F | | 5.24 (m, br) (MeOD) |
| 7u | 9.1 | 78 | 48 | 96.4 | 8.91 | F | | 5.22 (m, br) (MeOD) |
| 7v | 9.6 | 57 | 23 | 99.8 | 2.67 | A | 461.1 | 4.97, 5.09 (2xm, br) (DMSO) |
| 7w | 9.5 | 32 | 62 | 99.9 | 2.74 | A | 475.2 | 4.72 (m) (MeOD) |
| 7x | 9.3 | 66 | 61 | 98.4 | 2.52 | A | 503.2 | 4.72 (m) (MeOD) |
| 7y | 9.5 | 57 | 23 | 99.1 | 2.65 | A | 473.2 | 4.63 (m) (MeOD) |
| 7z | 9.4 | 58 | 42 | 100 | 2.84 | A | | 4.74 (m) (MeOD) |
| 7aa | 9.0 | 93 | 29 | 100 | 2.72 | A | | 5.10 (m) (MeOD) |
| 7ab | 9.4 | 86 | 17 | 98 | 1.00 | B | | 5.00 (m, br) (DMSO) |
| 7ac | 8.8 | 94 | 39 | 100 | 1.04 | B | | 5.02 (m, br) (DMSO) |
| 7ad | 9.0 | 92 | 80 | 100 | 1.19 | B | | 5.04 (m, br) (DMSO) |
| 7ae | 7.9 | 99 | 58 | 99.4 | 2.50 | A | 449.2 | 5.12, 5.22 (2xm, br) (DMSO) |
| 7af | 8.5 | 92 | 12 | 96.4 | 2.31 | A | 446.2 | 5.05, 5.24 (2xm, br) (DMSO) |
| 7ag | 8.7 | 81 | 61 | 97.7 | 2.60 | A | 489.2 | 5.05, 5.15 (2xm, br) (DMSO) |
| 7ah | 8.6 | 94 | 16 | 97 | 2.54 | A | 507.1 | 5.10 (m, br) (DMSO) |
| 7ai | 8.1 | 96 | 65 | 99.8 | 0.80 | B | 455.3 | 5.05, 5.16 (2xm, br) (DMSO) |
| 7aj | 8.5 | 100 | 59 | 99.1 | 0.85 | B | 469.3 | 5.01, 5.15 (2xm, br) (DMSO) |
| 7ak | 8.5 | 93 | 46 | 99.4 | 0.77 | B | 491.2 | 5.05, 5.15 (2xm, br) (DMSO) |
| 7al | 8.1 | 100 | 30 | 99.5 | 0.70 | B | 457.9 | 5.15 (m, br) (DMSO) |
| 7am | 7.6 | 93 | 26 | 99.7 | 2.34 | A | 470.2 | 5.18 (m) (MeOD) |
| 7an | 8.7 | 98 | 30 | 96 | 2.71 | A | 475.2 | 5.07, 5.17 (2xm, br) (DMSO) |
| 7ao | 7.6 | 80 | 34 | 98.7 | | | | 4.62 (m) (CDCl$_3$) |
| 7ap | 8.7 | 90 | 67 | 100 | 2.65 | A | 489.2 | 5.10 (m, br) (DMSO) |
| 7aq | 7.6 | 78 | 42 | 99 | 2.40 | A | 462.2 | 5.14 (m) (CDCl$_3$) |
| 7ar | 7.7 | 82 | 16 | 97.4 | 0.70 | B | 488.2 | 5.15 (m) (CDCl$_3$) |
| 7as | 7.4 | 55 | 36 | 98.8 | 2.55 | A | 513.2 | 5.05 (m, br) (DMSO) |
| 7at | 8.8 | 101 | 82 | 98.5 | 0.94 | B | 507.2 | 5.10 (m, br) (DMSO) |

TABLE 4-continued

Biological and physicochemical data of cpds. according to Formulae 7

| cpd | ERα pIC50 (a) | DR (%) (b) | yield (%) | purity (%) | HPLC Rf (min) | HPLC method | MS-ESI [M + H] | azetidine NMR H-3 ppm |
|---|---|---|---|---|---|---|---|---|
| 7au | 9.0 | 89 | 70 | 99.7 | 2.74 | A | 475.2 | 4.85, 5.00 (2xm, br) (DMSO) |
| 7av | 7.6 | 84 | 43 | 99.5 | 2.27 | A | 491.2 | 4.65 (m) (CDCl$_3$) |
| 7aw | 8.1 | 64 | 48 | 93.4 | 0.90 | B | 505.2 | 4.70 (m) (CDCl$_3$) |
| 7ax | 9.1 | 33 | 38 | 99.3 | 0.99 | B | 487.2 | 4.69 (m) (CDCl$_3$) |
| 7ay | 8.4 | 62 | 39 | 98.8 | 0.84 | B | 489.3 | 4.8 (m, br) (DMSO) |
| 7az | 8.2 | 88 | 21 | 99.5 | 1.15 | B | 469.3 | 5.04, 5.15 (2xm, br) (DMSO) |
| 7ba | 7.8 | 51 | 27 | 99 | 2.47 | A | 473.3 | 5.05, 5.15 (2xm, br) (DMSO) |
| 7bb | 8.7 | 90 | 45 | 98 | 1.32 | B | 485.3 | 5.09 (m, br) (DMSO) |
| 7bc | 9.6 | 47 | 46 | 98 | 0.93 | B | 414.3 | 4.85, 4.95 (2xm, br) (DMSO) |
| 7bd | 7.6 | 75 | 53 | 100 | 2.79 | B | 458.19 | 4.91 (m, br) (DMSO) |
| 7be | 8.4 | 58 | 49 | 99 | 2.46 | B | 444.20 | 4.92 (m, br) (DMSO) |
| 7bf | 7.2 | 33 | 85 | 95 | 0.95 | B | 456.3 | 4.72 (m, br) (DMSO) |
| 7bg | 7.5 | 75 | 46 | 93 | 1.82, 1.99 | C | 398.22 | 4.82-5.17 (4xm, br) (DMSO) |
| 7bh | 9.3 | −5 (d) | 58 | 97 | 2.66 | C | 414.19 | 4.90, 5.09 (2xm, br) (DMSO) |
| 7bi | 8.3 | 63 | 64 | 97 | 1.49, 1.58 | B | 414.4 | 5.01 (2xm, br) (DMSO) |
| 7bj | 8.1 | 63 | 46 | 100 | 1.53, 1.58 | B | 404.1 | 5.01 (m, br) (DMSO) |

(a) See Example 11
(b) See Example 13
(c) The corresponding analogue of compound 7c in which the N-propylazetidinyl-3-oxy side chain is replaced by a piperidinylethyloxy side chain (i.e. compound LY- 335562, described as Example 18 in U.S. Pat. No. 5,488,058) shows downregulation of −199% (i.e. upregulation of 199%).
(d) Downregulation of −5% means upregulation of 5%. The corresponding analogue of compound 7bh inwhich the N-propylazetidinyl-3-oxy side chain is replaced by a dimethylaminoethyloxy side chain (i.e. 4-hydroxy-tamoxifen) shows down-regulation of −343% (i.e. upregulation of 343%).
A: UPLC BEH C18, 1.7 um, 2.1x100 mm (0 to 60% acetonitrile/water/5% TFA)
B: UPLC BEH C18, 1.7 um, 2.1x100 mm (40 to 80% acetonitrile/water/5% TFA)
C: LCMS Xbridge, C18, 3.5 um, 3.5x20 mm (0 to 100% acetonitrile/water/5% TFA)
D: Luna C18, 3 um, 100x2 mm (25% acetonitrile/75% water)
E: Luna C18, 3 um, 100x2 mm (0-80% acetonitrile/5% TFA)
F: HPLC BEH C18 5 um Luna column (10 to 60% acetonitrile/water 5%TFA)
G: HPLC BEH C18 5 um Luna column (10 to 70% acetonitrile/water 5%TFA)

TABLE 5

Biological and physicochemical data of cpds. according to Formulae 8

| cpd | ERα pIC50 (a) | MCF7 ia (b) | DR (%) (c) | yield (%) | purity (%) | HPLC Rf (min) | HPLC method | MS-ESI [M + H] | azetidine NMR H-3 ppm |
|---|---|---|---|---|---|---|---|---|---|
| 8a | 9.1 | 0.10 | 53 | 44 | 98 | 14.83 | E | 432.2 | 5.05, 5.15 (2xm, br) (DMSO) |
| (d) 8c | 8.8 | 0.05 | 79 | 19 | 99 | 2.13 | A | 460 | 5.05, 5.15 (2xm, br) (DMSO) |
| 8d | 9.6 | 0.02 | 57 | 23 | 99.8 | 2.67 | A | 461.1 | 4.97, 5.09 (2xm, br) (DMSO) |
| 8e | 8.7 | 0.07 | 81 | 61 | 97.7 | 2.60 | A | 489.2 | 5.05, 5.15 (2xm, br) (DMSO) |
| 8f | 8.6 | 0.06 | 94 | 16 | 97 | 2.54 | A | 507.1 | 5.10 (m, br) (DMSO) |
| 8g | 8.5 | 0.07 | 93 | 46 | 99.4 | 0.77 | B | 491.2 | 5.05, 5.15 (2xm, br) (DMSO) |
| 8h | 8.2 | 0.08 | 88 | 21 | 99.5 | 1.15 | B | 469.3 | 5.04, 5.15 (2xm, br) (DMSO) |
| 8i | 8.7 | 0.03 | 90 | 45 | 98 | 1.32 | B | 485.3 | 5.09 (m, br) (DMSO) |
| 8j | 9.6 | 0.06 | 47 | 46 | 98 | 0.93 | B | 414.3 | 4.85, 4.95 (2xm, br) (DMSO) |
| 8k | 7.5 | 0.08 | 75 | 46 | 93 | 1.82, 1.99 | C | 398.22 | 4.82-5.17 (4xm, br) (DMSO) |

(a) See Example 11
(b) See Example 12
(c) See Example 13
(d) See comment (c) to cpd. 7c in Table 4
A: UPLC BEH C18, 1.7 um, 2.1x100 mm (0 to 60% acetonitrile/water/5% TFA)
B: UPLC BEH C18, 1.7 um, 2.1x100 mm (40 to 80% acetonitrile/water/5% TFA)
C: LCMS Xbridge, C18, 3.5 um, 3.5x20 mm (0 to 100% acetonitrile/water/5% TFA)
D: Luna C18, 3 um, 100x2 mm (25% acetonitrile/75% water)
E: Luna C18, 3 um, 100x2 mm (0-80% acetonitrile/5% TFA)

TABLE 6

Biological and physicochemical data of cpds. according to Formulae 9

| cpd | ERα pIC50 [a] | MCF7 [b] | DR (%) [c] | RRat AUC (μM·h) [d] | RRat Cmax (μM) [d] | yield (%) | purity (%) | HPLC Rf (min) | HPLC method | MS-ESI [M + H] | azetidine NMR H-3 ppm |
|---|---|---|---|---|---|---|---|---|---|---|---|
| 9a | 9.6 | 0.02 | 57 | 2.05 | 0.57 | 23 | 99.8 | 2.67 | A | 461.1 | 4.97, 5.09 (2xm, br) (DMSO) |
| 9b | 9.5 | | 32 | 1.55 | 0.52 | 62 | 99.9 | 2.74 | A | 475.2 | 4.72 (m) (MeOD) |
| 9c | 9.5 | | 57 | 1.20 | 0.29 | 23 | 99.1 | 2.65 | A | 473.2 | 4.63 (m) (MeOD) |
| 9d | 9.4 | | 58 | 1.03 | 0.35 | 42 | 100 | 2.84 | A | | 4.74 (m) (MeOD) |
| 9e | 9.0 | | 93 | 3.58 | 0.99 | 29 | 100 | 2.72 | A | | 5.10 (m) (MeOD) |
| 9f | 7.6 | | 84 | 3.80 | 0.99 | 43 | 99.5 | 2.27 | A | 491.2 | 4.65 (m) (CDCl$_3$) |
| 9g | 7.5 | 0.08 | 75 | 1.97 | 0.45 | 46 | 93 | 1.82, 1.99 | C | 398.22 | 4.82-5.17 (4xm, br) (DMSO) |
| 9h | 8.3 | | 63 | 1.07 | 0.23 | 64 | 97 | 1.49, 1.58 | B | 414.4 | 5.01 (2xm, br) (DMSO) |

[a] See Example 11
[b] See Example 12
[c] See Example 13
[d] See Example 14
A: UPLC BEH C18, 1.7 um, 2.1x100 mm (0 to 60% acetonitrile/water/5% TFA)
B: UPLC BEH C18, 1.7 um, 2.1x100 mm (40 to 80% acetonitrile/water/5% TFA)
C: LCMS Xbridge, C18, 3.5 um, 3.5x20 mm (0 to 100% acetonitrile/water/5% TFA)

What is claimed:

1. N-substituted azetidine derivative of the following Formula 1

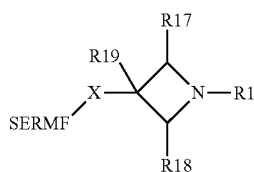

Formula 1 wherein

SERMF is a Selective Estrogen Receptor Modulator fragment;

X is no atom, O, S, CH$_2$, carbonyl, N—R5;

R1 is H, (C1-8)alkyl, (C3-8)cycloalkyl, (C3-6)heterocycloalkyl, (C2-6)alkenyl, (C2-6)-alkynyl, (C1-4)alkylcarbonyl, (C1-4)alkoxy(C2-4)alkyl, (C3-6)cycloalkyl(C1-3)alkyl, (C3-6)heterocycloalkyl(C1-3)alkyl, each independently optionally substituted with one or more halogen, nitrile, hydroxyl or (C1-2)alkyl;

R5 is H, (C1-3)alkyl, optionally substituted with one or more fluorine;

R17, R18 and R19 are independently of each other H, fluorine, nitrile or (C1-3)alkyl, optionally substituted with one or more fluorine;

or a prodrug, isotopically-labelled derivative or pharmaceutically acceptable salt thereof.

2. An N-substituted azetidine derivative according to claim 1 selected from the group consisting of compounds according to any one of Formulae 3

Formulae 3

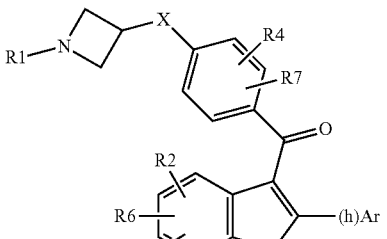

A

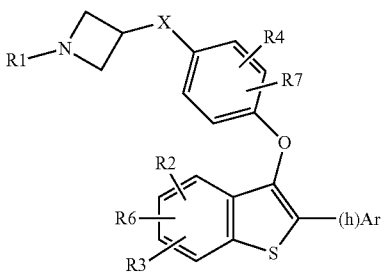

B

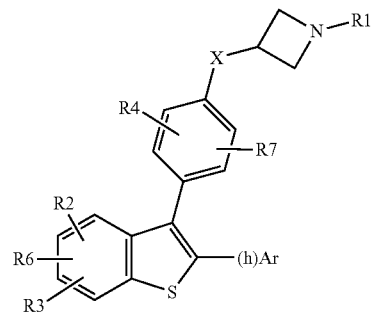

C

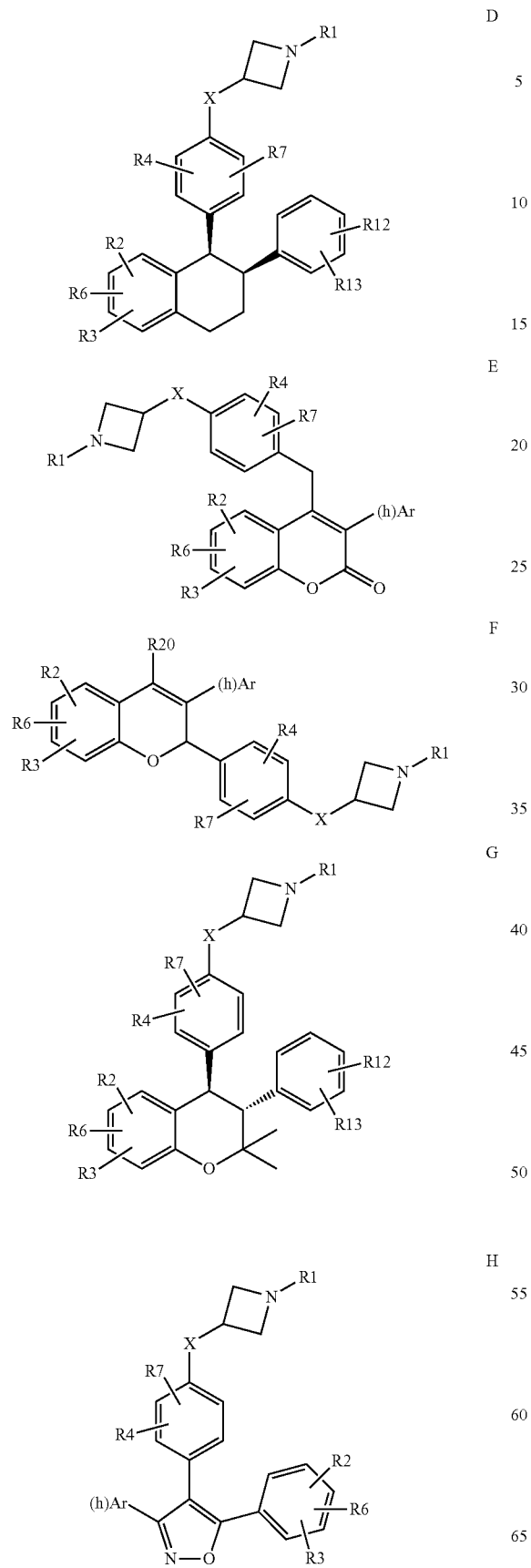
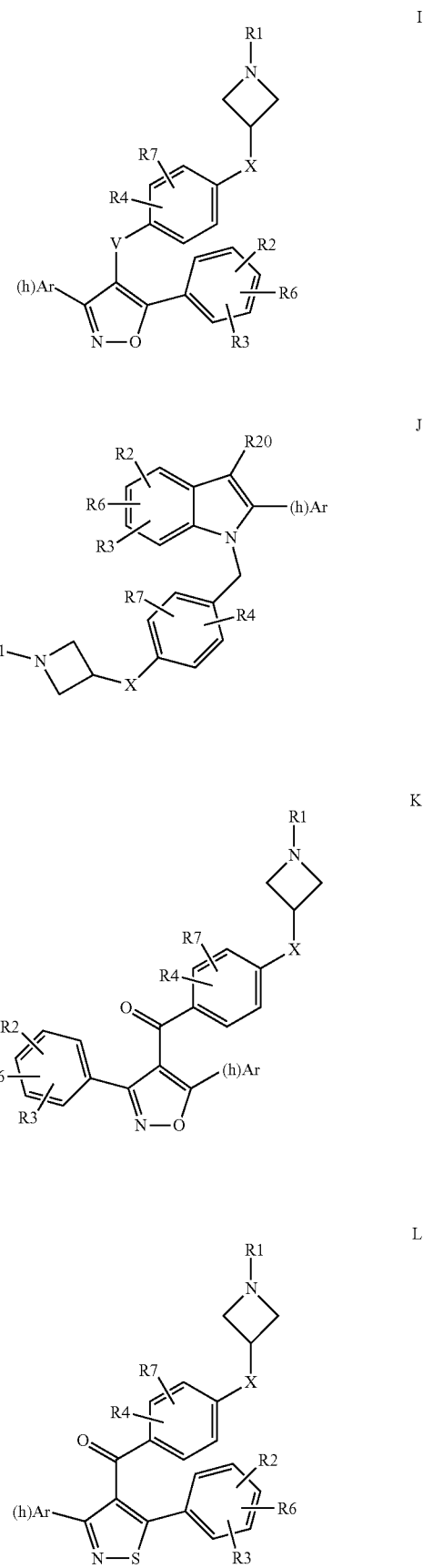

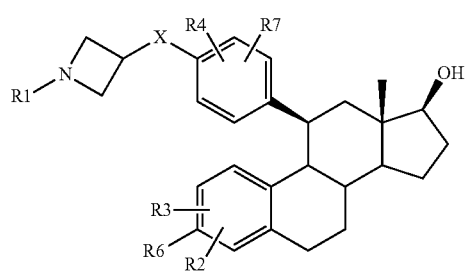
M
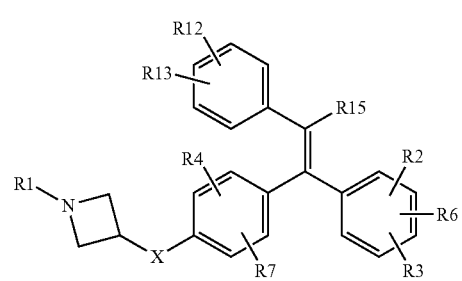
N
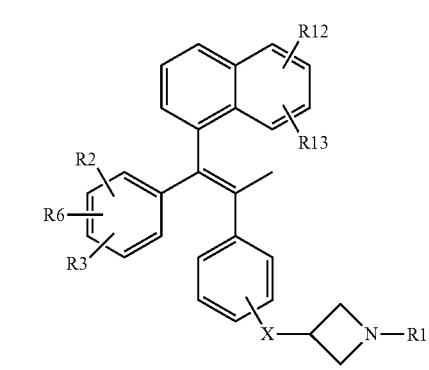
O
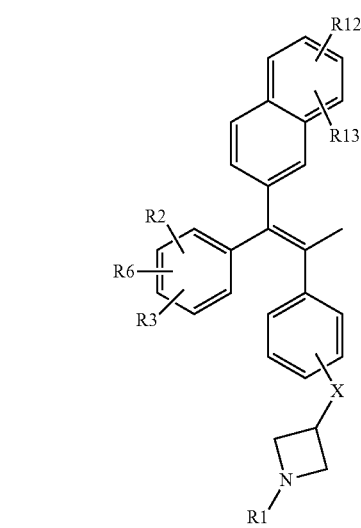
P
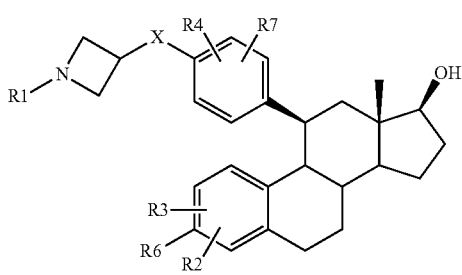
Q
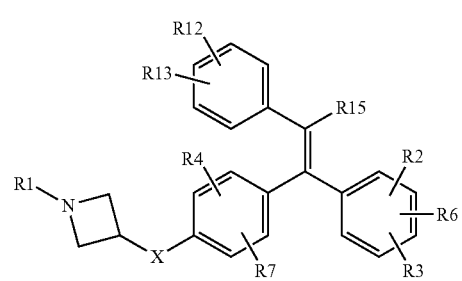
R
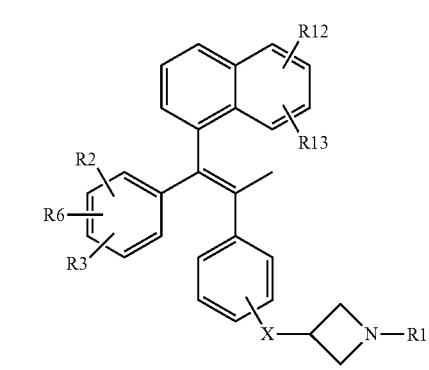
S
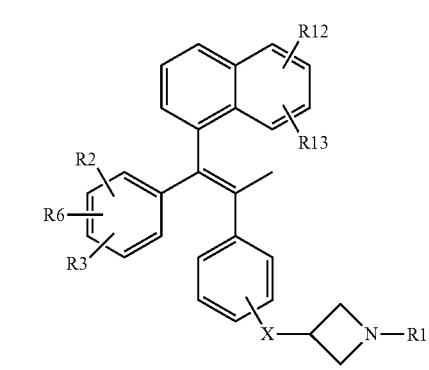
T

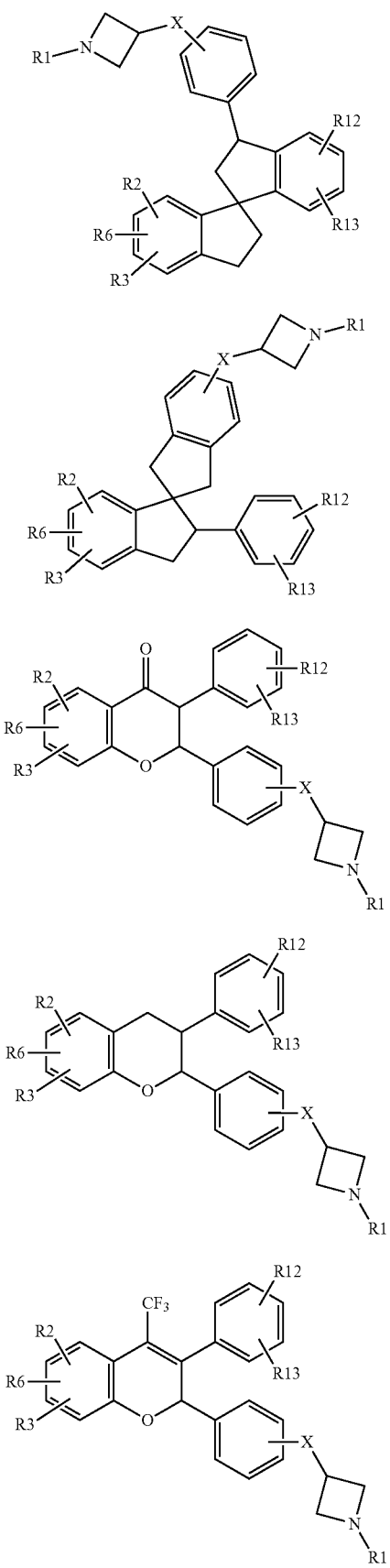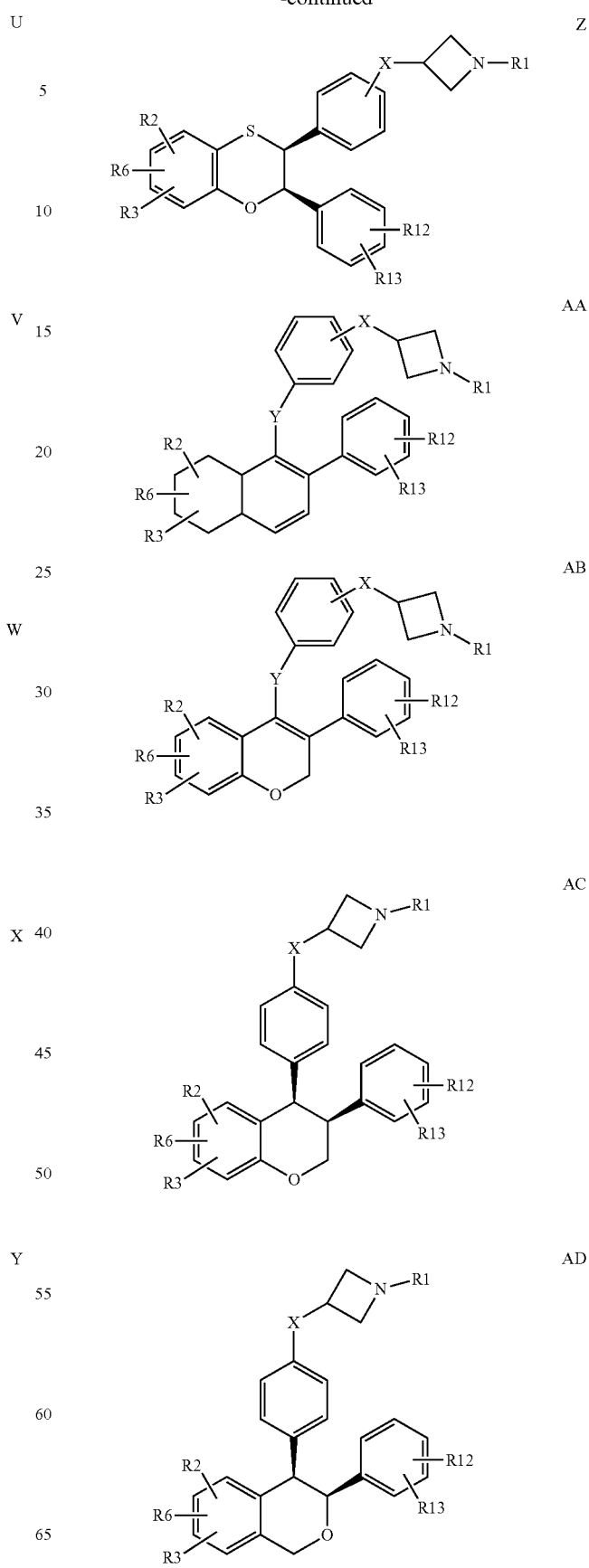

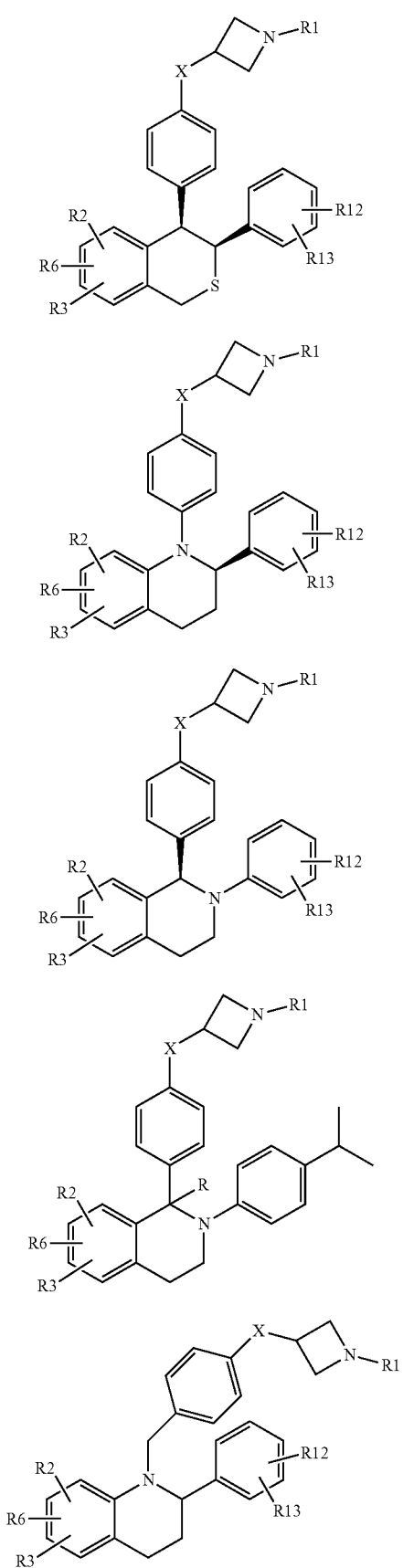
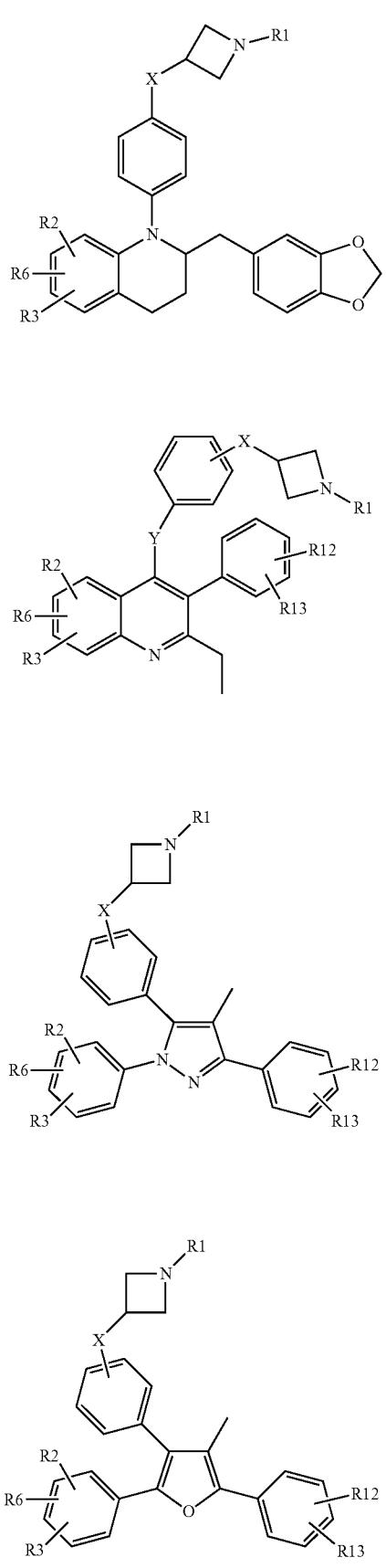

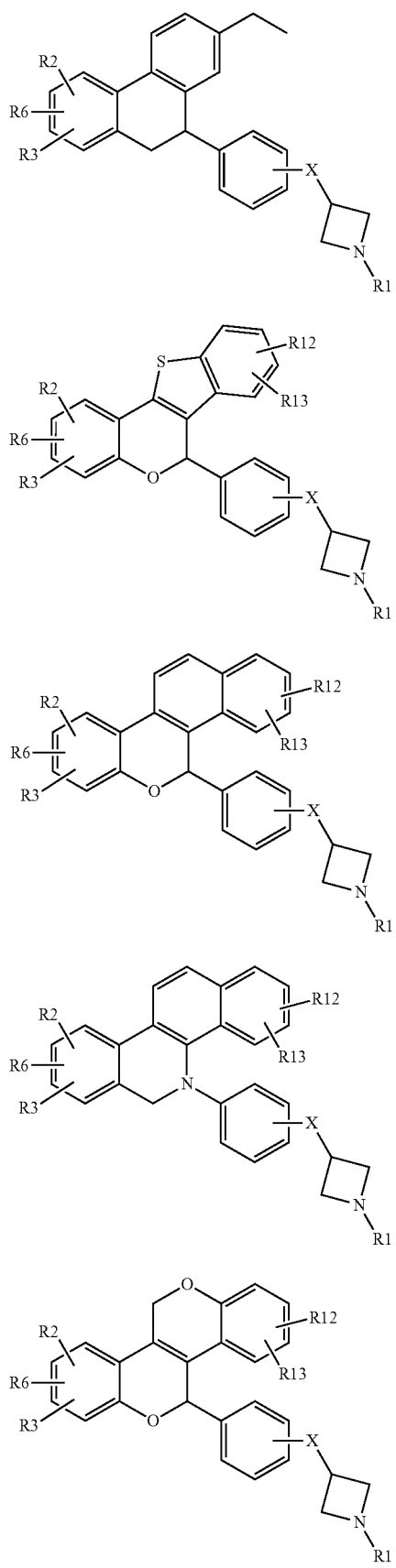
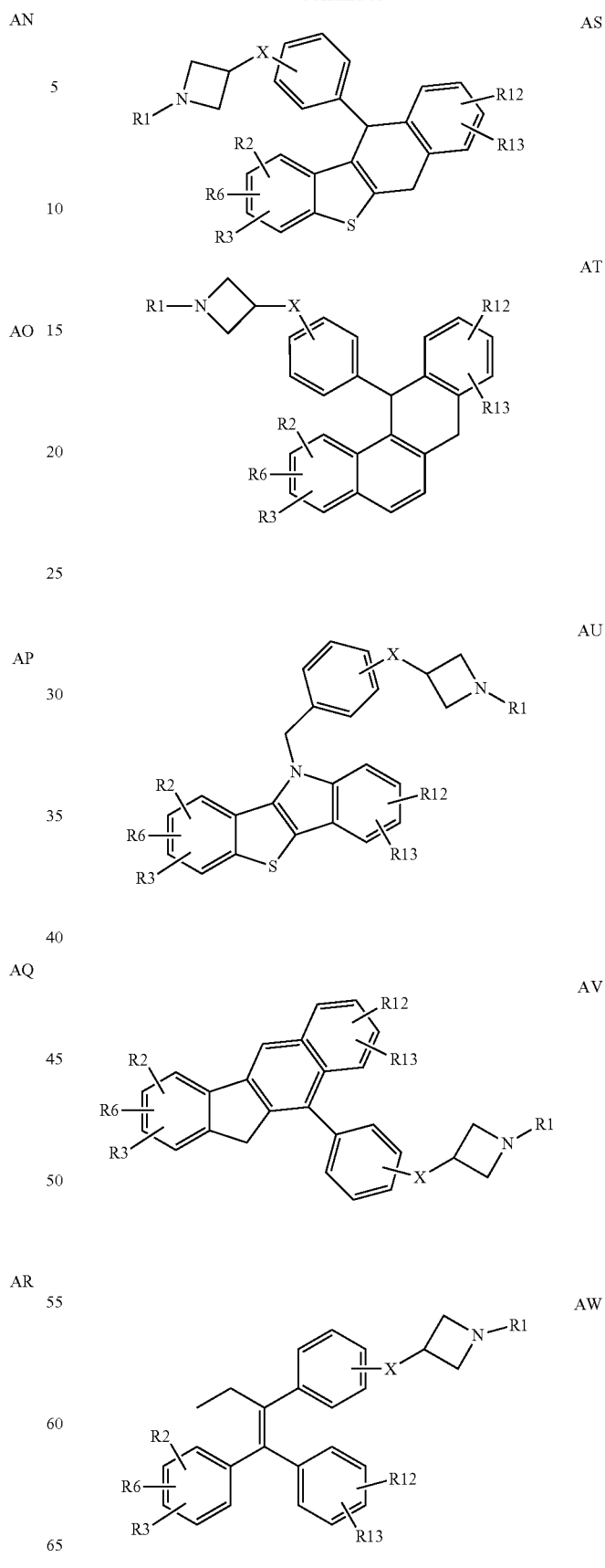

wherein
R1 is (C1-8)alkyl, (C3-8)cycloalkyl, (C3-6)heterocycloalkyl, (C2-6)alkenyl, (C2-6)-alkynyl, (C1-4)alkylcarbonyl, (C1-4)alkoxy(C2-4)alkyl, (C3-6)cycloalkyl(C1-3)alkyl, (C3-6)heterocycloalkyl(C1-3)alkyl, each independently optionally substituted with one or more halogen, nitrile, hydroxyl or (C1-2)alkyl;

X is no atom, O, S, $CH_2$, carbonyl, N—R5;

(h)Ar is a (hetero)aromatic ring, optionally substituted with R12 and R13;

R2 and R3 are independently of each other H, fluorine, chlorine, (C1-3)alkyl, (C1-3)-alkoxy, (C1-3)alkylthio, $CF_3$ or nitrile;

R4 and R7 are independently of each other H, fluorine, chlorine, (C1-2)alkyl, $CF_3$ or nitrile;

R12 is H, fluorine, chlorine, (C1-2)alkyl, (C1-2)alkoxy, nitrile or hydroxyl;

R13 is H, fluorine, chlorine, (C1-3)alkyl, (C1-3)alkoxy, (C1-3)alkylthio, $CF_3$ or nitrile;

R6 is H, hydroxyl, amine or (C1-6)alkoxy;

R6 and R2 may be linked to form a (hetero)aromatic ring which is optionally substituted with fluorine, chlorine or (C1-3)alkyl;

R5 is H, (C1-3)alkyl, optionally substituted with one or more fluorine;

V is O, S, CH$_2$, CHOH, CH(C1-3)alkoxy, C=CH$_2$, carbonyl, N—R16;

R15 is H, halogen, nitro, nitrile or (C1-6)alkyl, optionally substituted with one or more halogen;

R16 is H, (C1-4)alkyl, (C1-4)alkenyl, optionally substituted with one or more halogen;

R20 is (C1-3)alkyl, optionally substituted with one or more fluorine.

3. An N-substituted azetidine derivative according to claim 1 selected from the group consisting of compounds according to any one of Formulae 4

Formulae 4

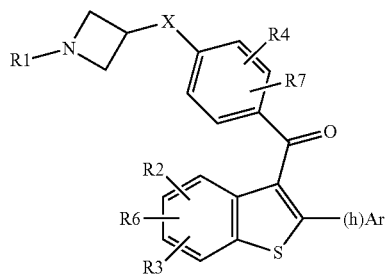
A

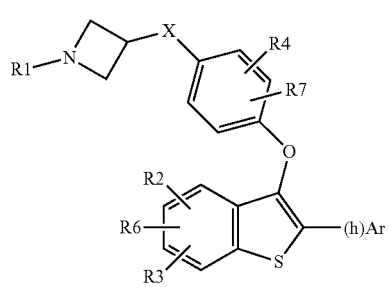
B

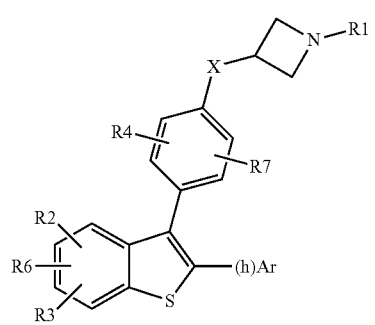
C

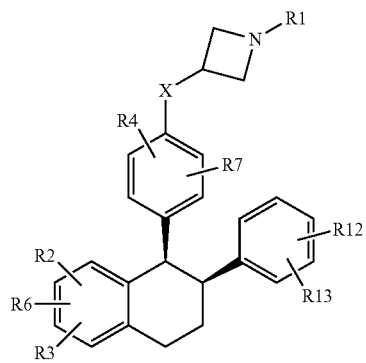
D

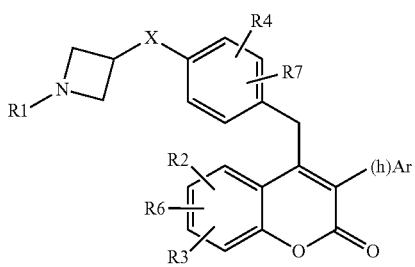
E

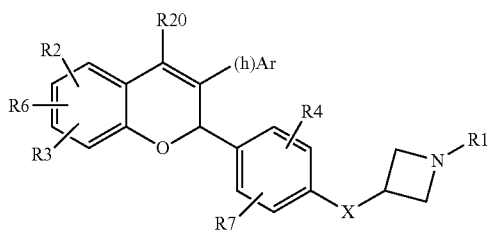
F

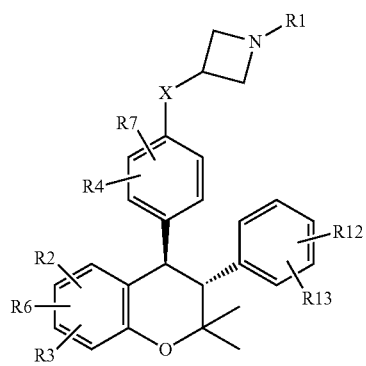
G

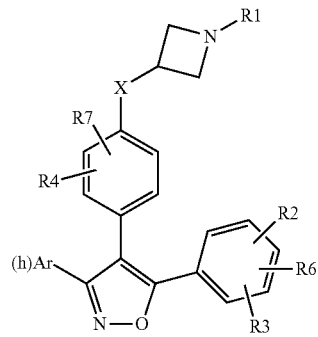
H

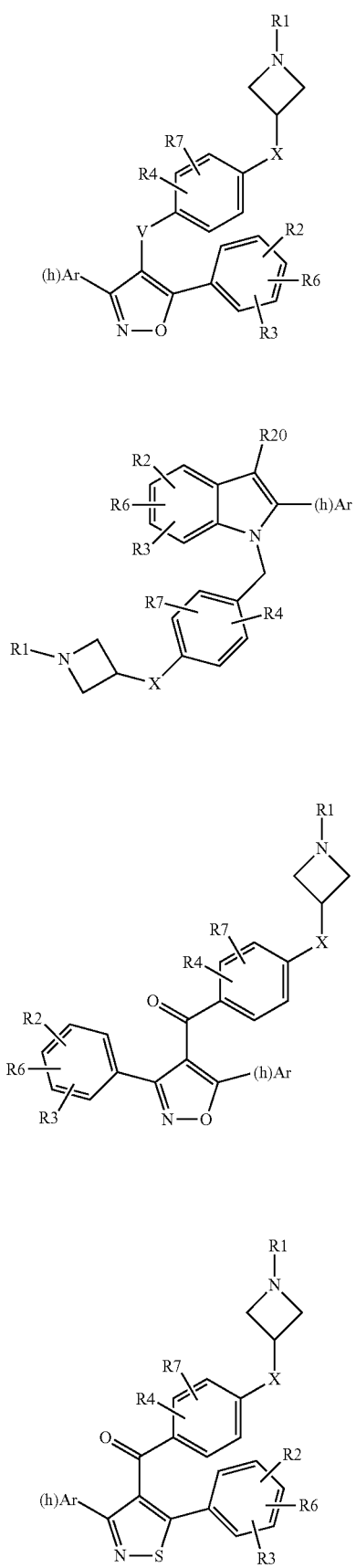

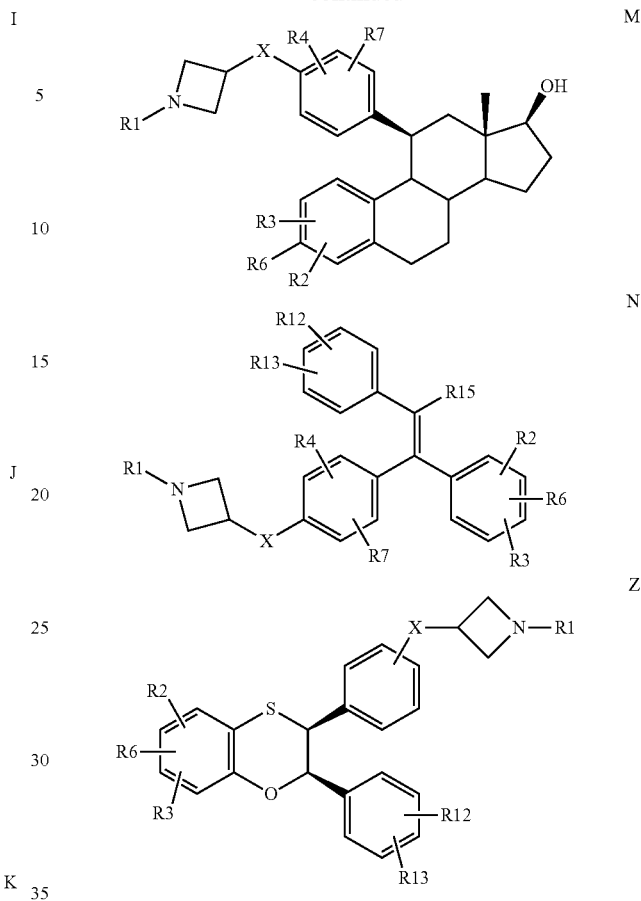

wherein
R1 is (C1-8)alkyl, (C3-8)cycloalkyl, (C3-6)heterocycloalkyl, (C2-6)alkenyl, (C2-6)-alkynyl, (C1-4)alkylcarbonyl, (C1-4)alkoxy(C2-4)alkyl, (C3-6)cycloalkyl(C1-3)alkyl, (C3-6)heterocycloalkyl(C1-3)alkyl, each independently optionally substituted with one or more halogen, nitrile, hydroxyl or (C1-2)alkyl;

X is no atom, O, S, $CH_2$, carbonyl, N—R5;

(h)Ar is a (hetero)aromatic ring, optionally substituted with R12 and R13;

R2 and R3 are independently of each other H, fluorine, chlorine, (C1-3)alkyl, (C1-3)-alkoxy, (C1-3)alkylthio, $CF_3$ or nitrile;

R4 and R7 are independently of each other H, fluorine, chlorine, (C1-2)alkyl, $CF_3$ or nitrile;

R12 is H, fluorine, chlorine, (C1-2)alkyl, (C1-2)alkoxy, nitrile or hydroxyl;

R13 is H, fluorine, chlorine, (C1-3)alkyl, (C1-3)alkoxy, (C1-3)alkylthio, $CF_3$ or nitrile;

R6 is H, hydroxyl, amine or (C1-6)alkoxy;

R6 and R2 may be linked to form a (hetero)aromatic ring which is optionally substituted with fluorine, chlorine or (C1-3)alkyl;

R5 is H, (C1-3)alkyl, optionally substituted with one or more fluorine;

V is O, S, $CH_2$, CHOH, CH(C1-3)alkoxy, C=$CH_2$, carbonyl, N—R16;

R15 is H, halogen, nitro, nitrile or (C1-6)alkyl, optionally substituted with one or more halogen;

R16 is H, (C1-4)alkyl, (C1-4)alkenyl, optionally substituted with one or more halogen;

R20 is (C1-3)alkyl, optionally substituted with one or more fluorine.
4. An N-substituted azetidine derivative according to claim 1 selected from the group consisting of compounds according to any one of Formulae 5
Formulae 5
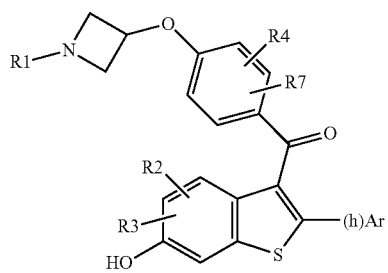
A
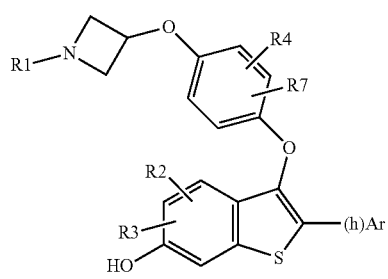
B
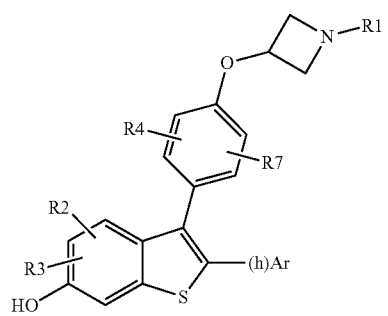
C
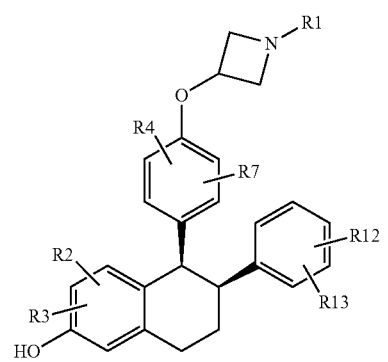
D
-continued
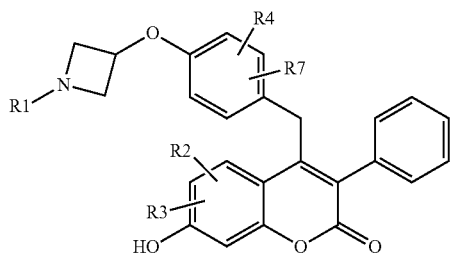
E
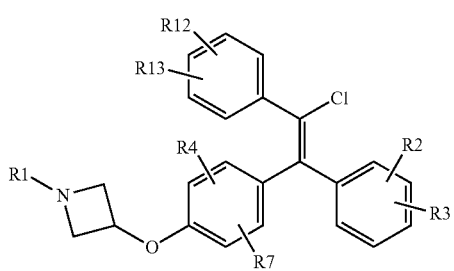
F
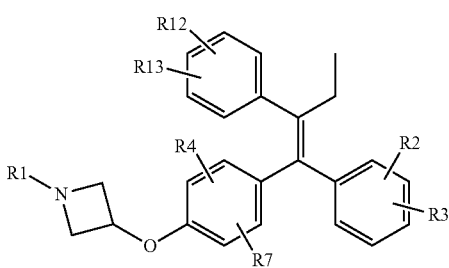
G
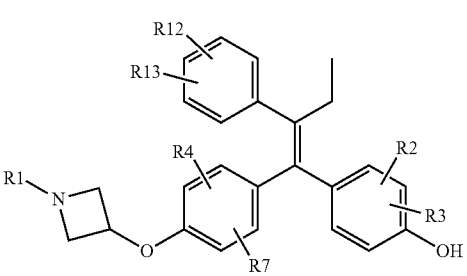
H
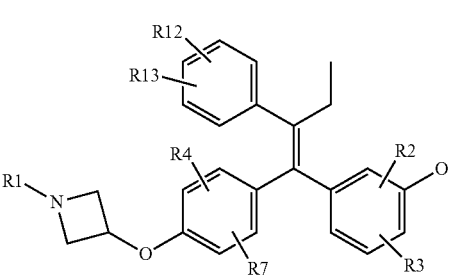
I

J

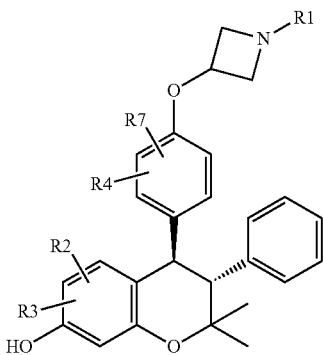

K

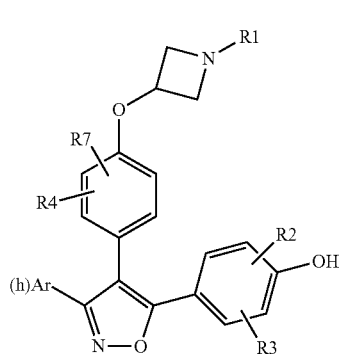

L

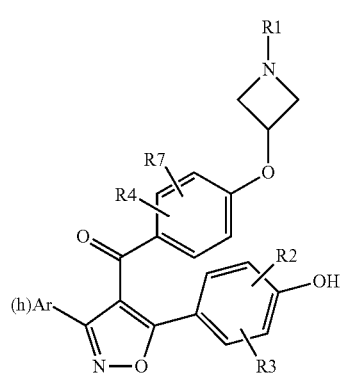

M

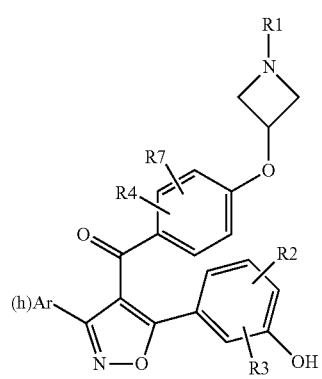

N

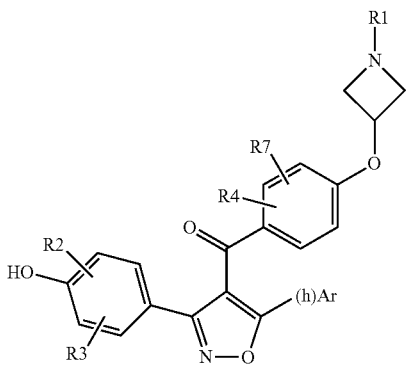

O

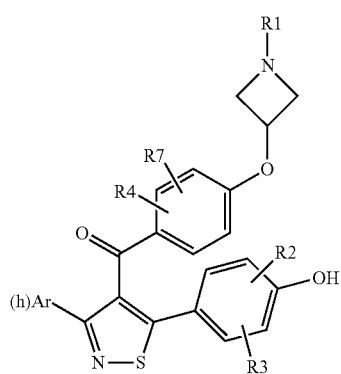

wherein

R1 is (C1-8)alkyl, (C3-8)cycloalkyl, (C3-6)heterocycloalkyl, (C2-6)alkenyl, (C2-6)-alkynyl, (C1-4)alkylcarbonyl, (C1-4)alkoxy(C2-4)alkyl, (C3-6)cycloalkyl (C1-3)alkyl, (C3-6)heterocycloalkyl(C1-3)alkyl, each independently optionally substituted with one or more halogen, nitrile, hydroxyl or (C1-2)alkyl;

(h)Ar is a (hetero)aromatic ring, optionally substituted with R12 and R13;

R2 and R3 are independently of each other H, fluorine, chlorine, (C1-3)alkyl, (C1-3)-alkoxy, (C1-3)alkylthio, $CF_3$ or nitrile;

R4 and R7 are independently of each other H, fluorine, chlorine, (C1-2)alkyl, $CF_3$ or nitrile;

R12 is H, fluorine, chlorine, (C1-2)alkyl, (C1-2)alkoxy, nitrile or hydroxyl;

R13 is H, fluorine, chlorine, (C1-3)alkyl, (C1-3)alkoxy, (C1-3)alkylthio, $CF_3$ or nitrile;

R6 is H, hydroxyl, amine or (C1-6)alkoxy;

R6 and R2 may be linked to form a (hetero)aromatic ring which is optionally substituted with fluorine, chlorine or (C1-3)alkyl.

5. An N-substituted azetidine derivative according to claim 1 selected from the group consisting of compounds according to any one of Formulae 6

Formulae 6
6a
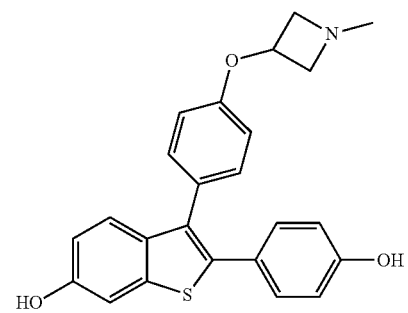
6b
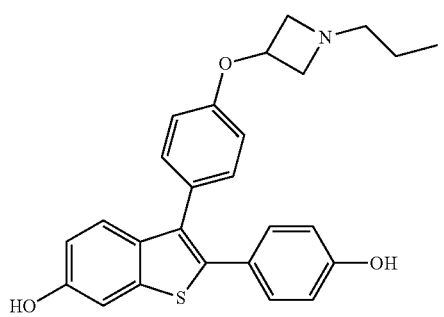
6c
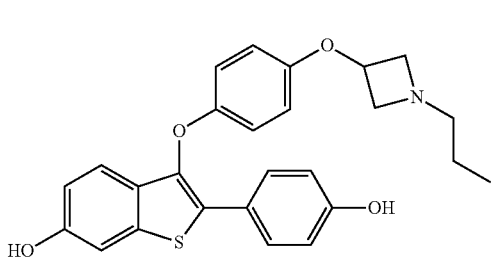
6d
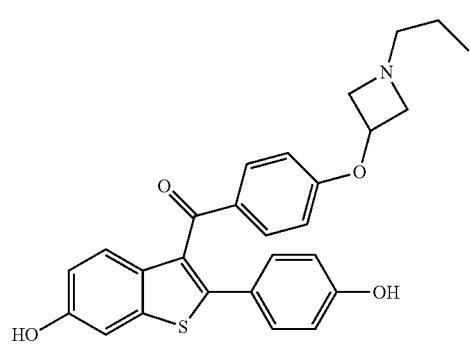
6e
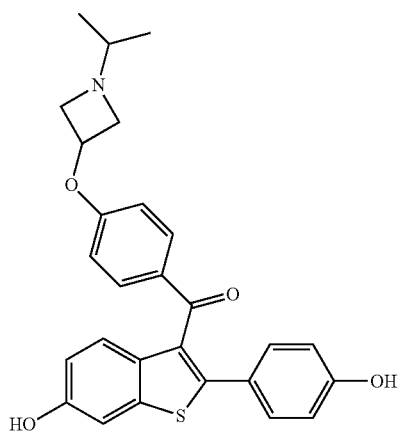
6f
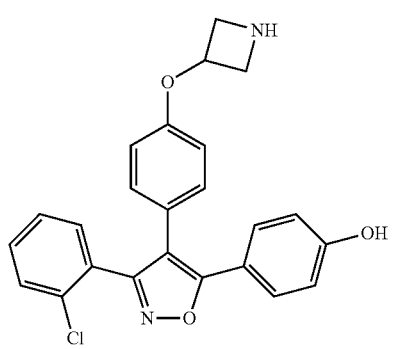
6g
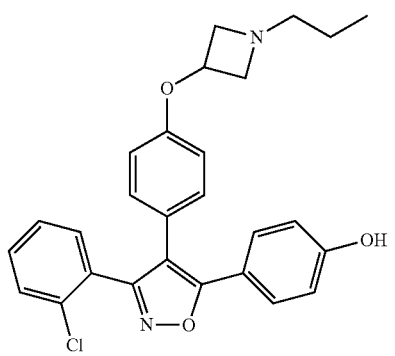
6h
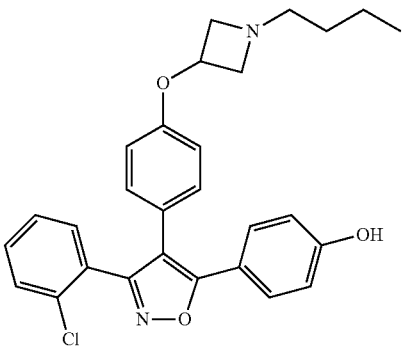

| | |
|---|---|
| 6i 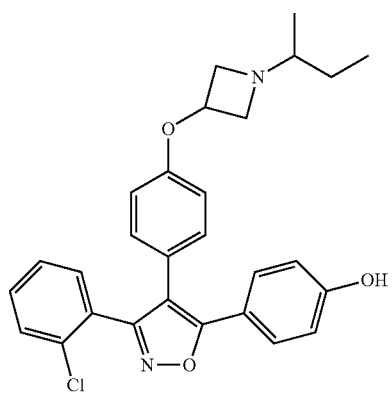 | 6m 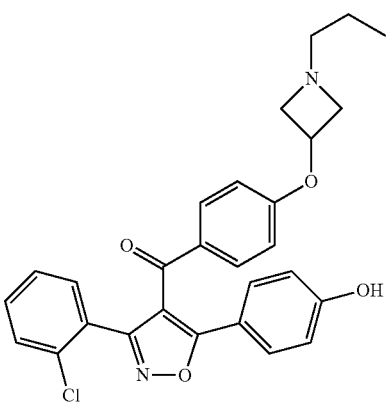 |
| 6j 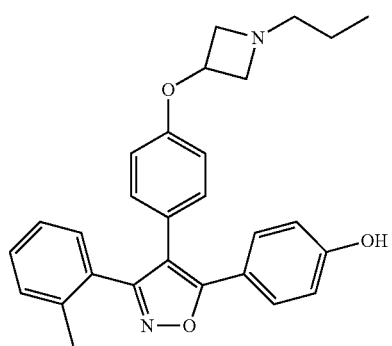 | 6n 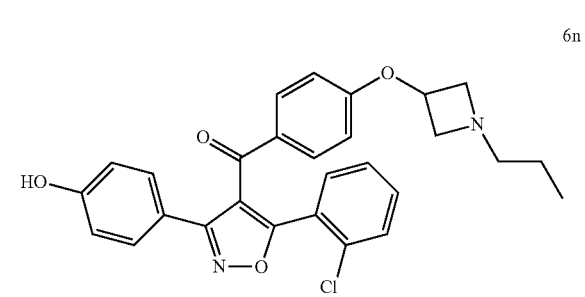 |
| 6k 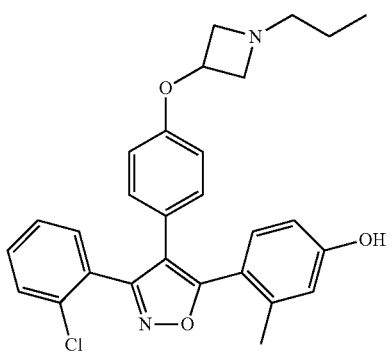 | 6o 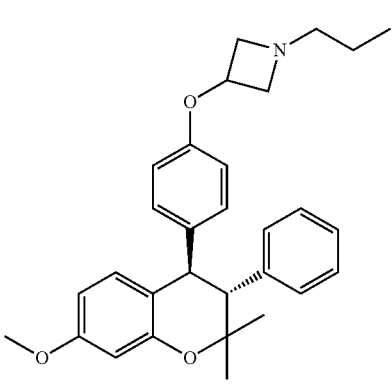 |
| 6l 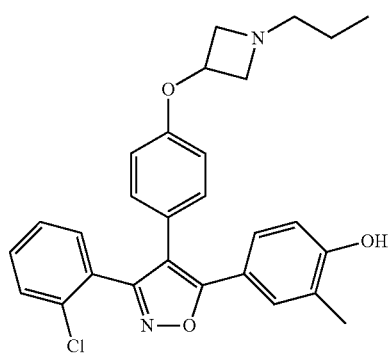 | 6p 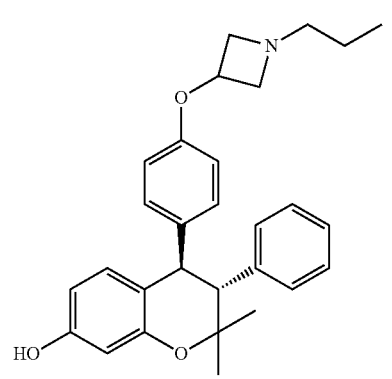 |

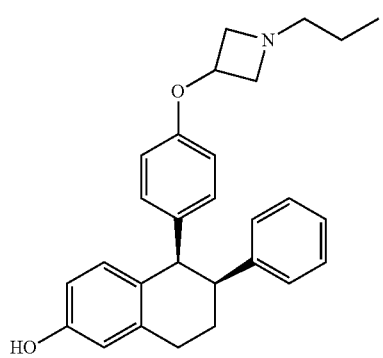
6q
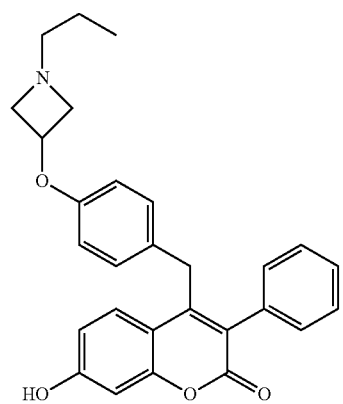
6r
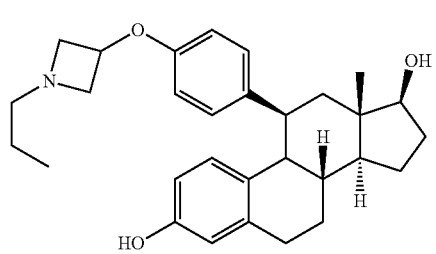
6s
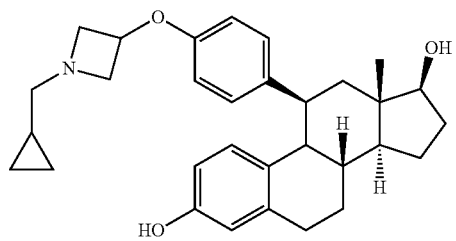
6t
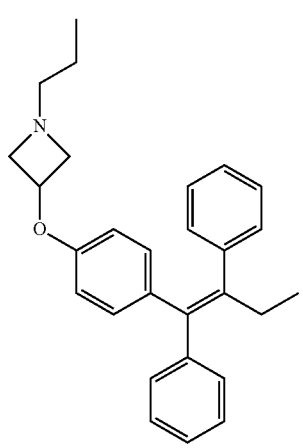
6u
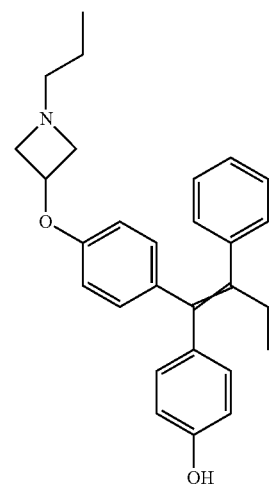
6v
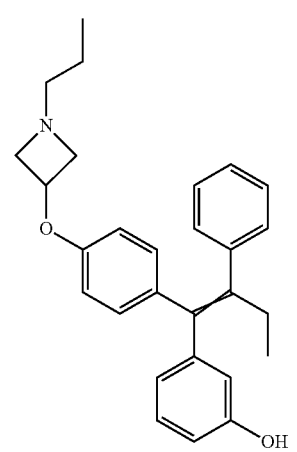
6w

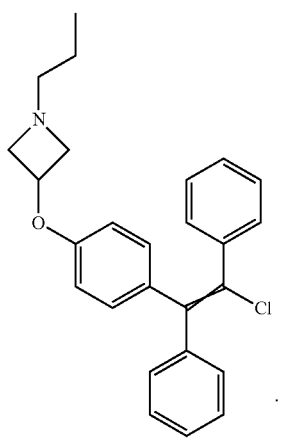
6x
6. An N-substituted azetidine derivative according to claim 1 selected from the group consisting of compounds according to any one of Formulae 7
Formulae 7
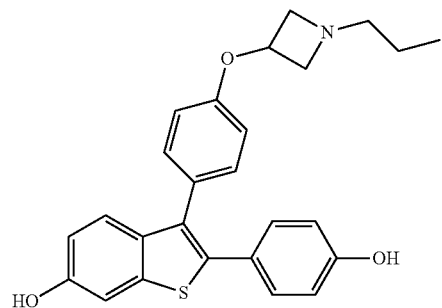
7a
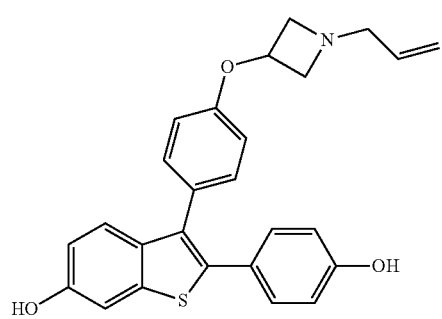
7b
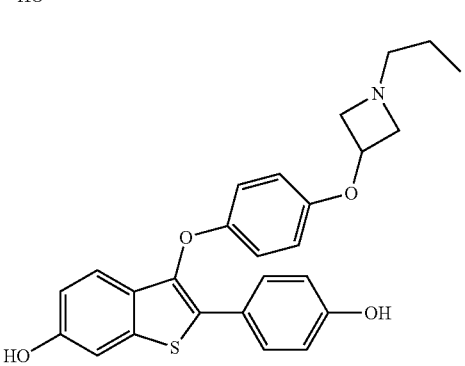
7c
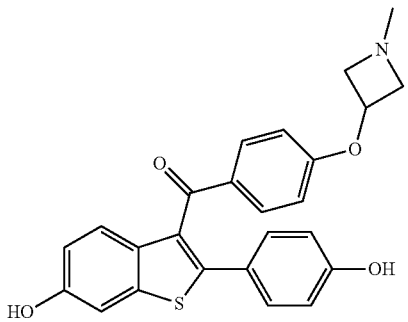
7d
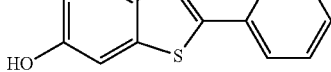
7e
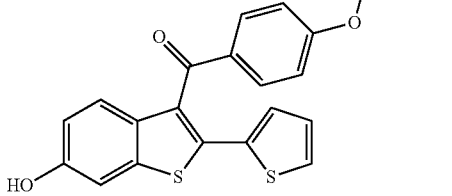
7f
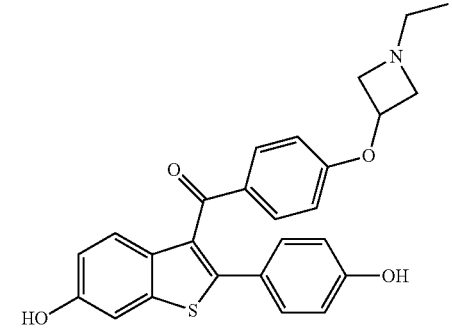
7g

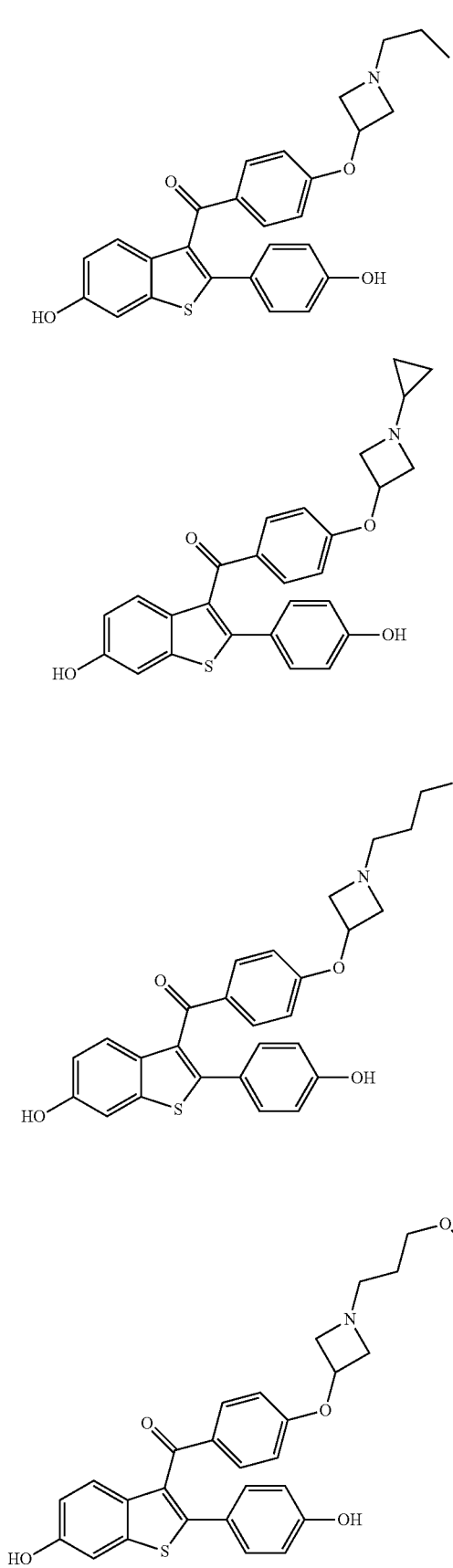
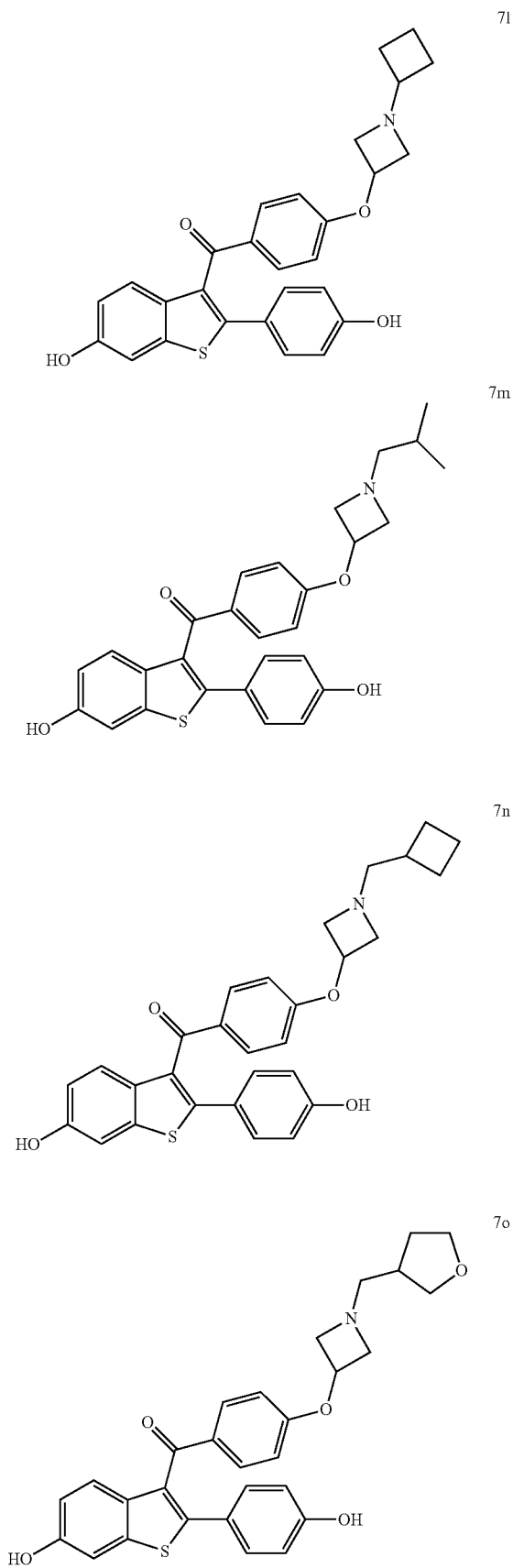

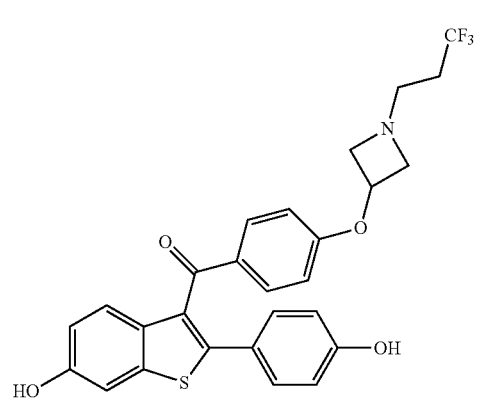
7p
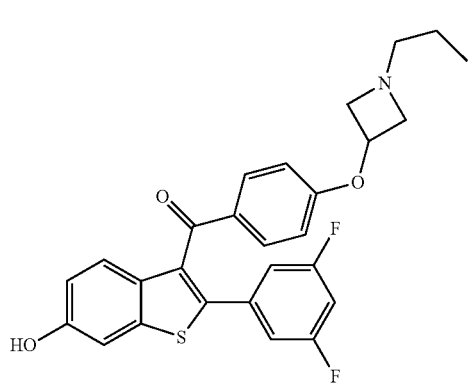
7t
7q
7u
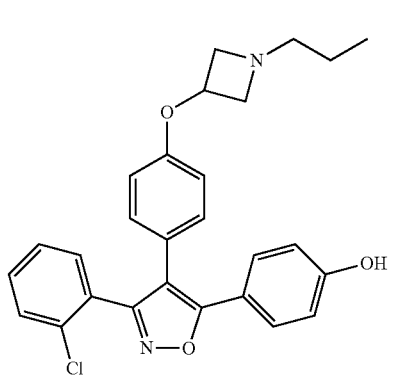
7r
7v
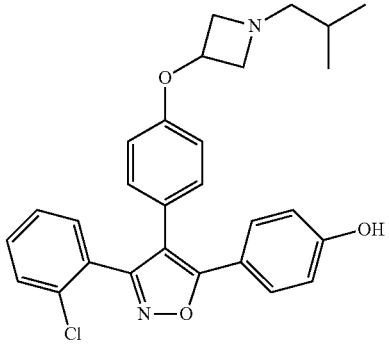
7s
7w

-continued
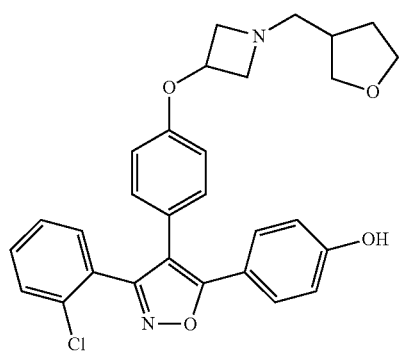
7x
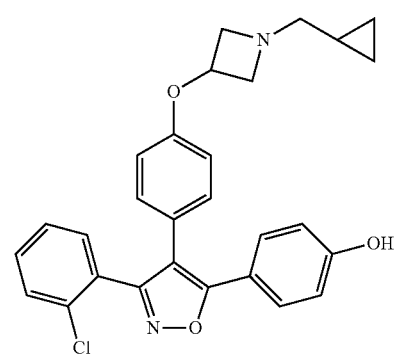
7y
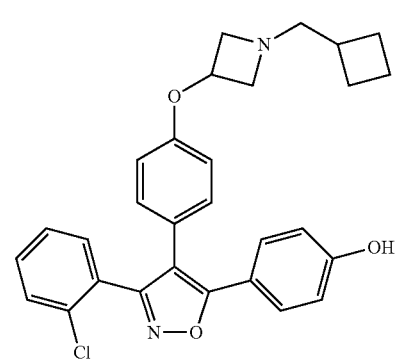
7z
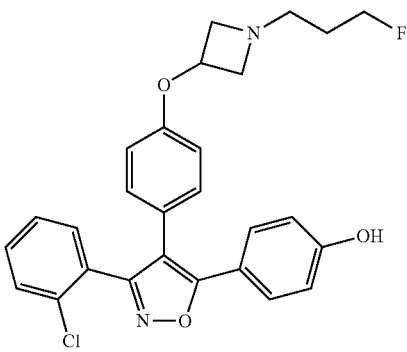
7aa
-continued
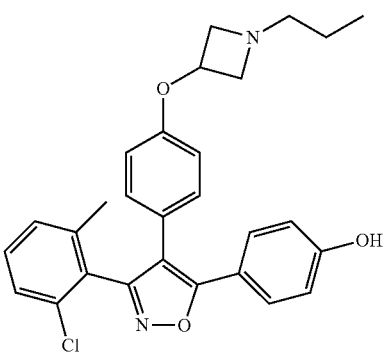
7ab
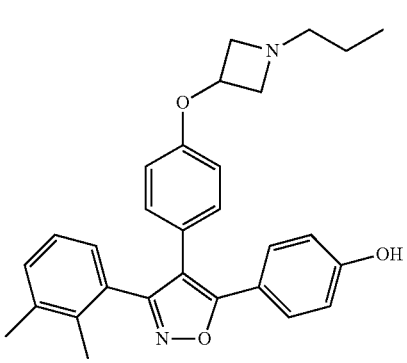
7ac
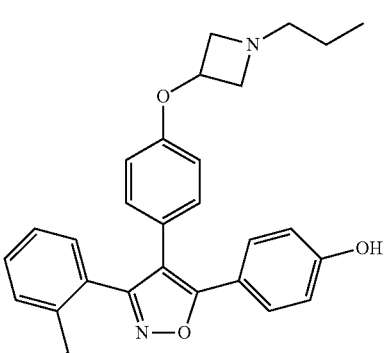
7ad
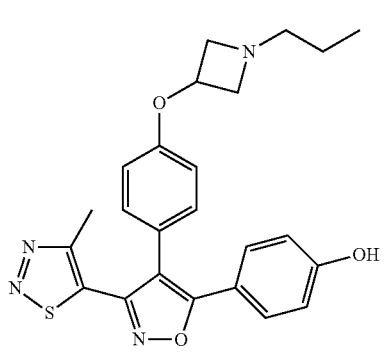
7ae -continued
7af
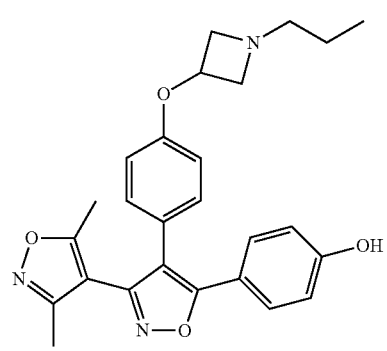
7ag
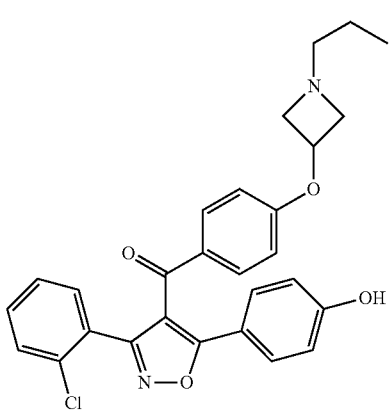
7ah
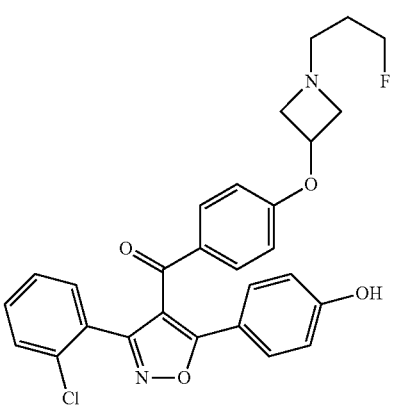
7ai
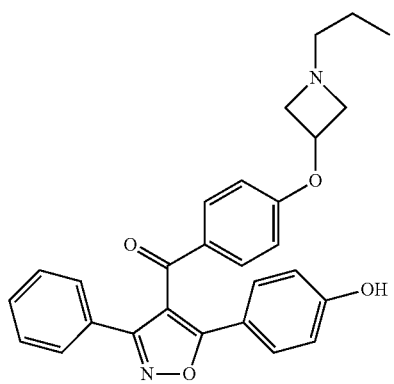
-continued
7aj
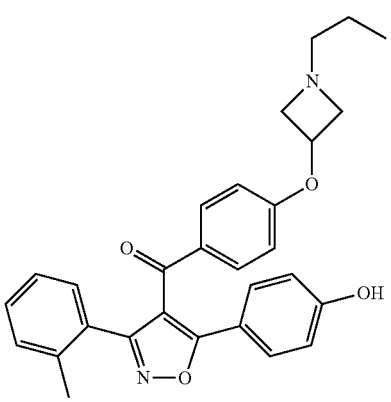
7ak
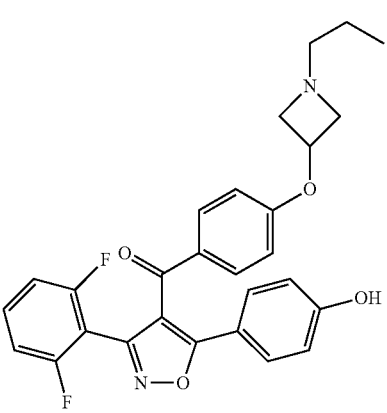
7al
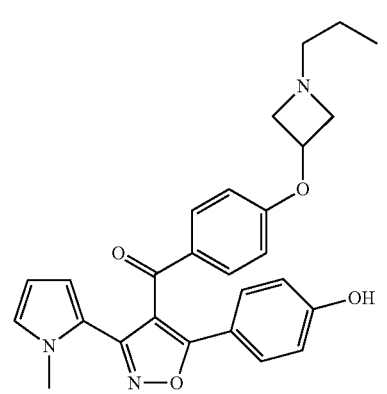
7am
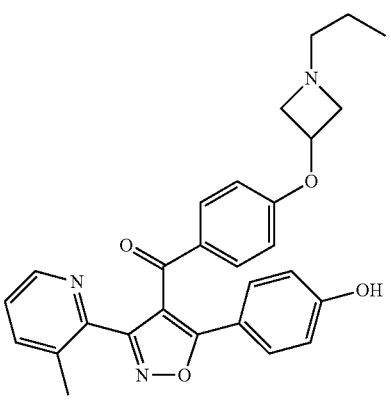

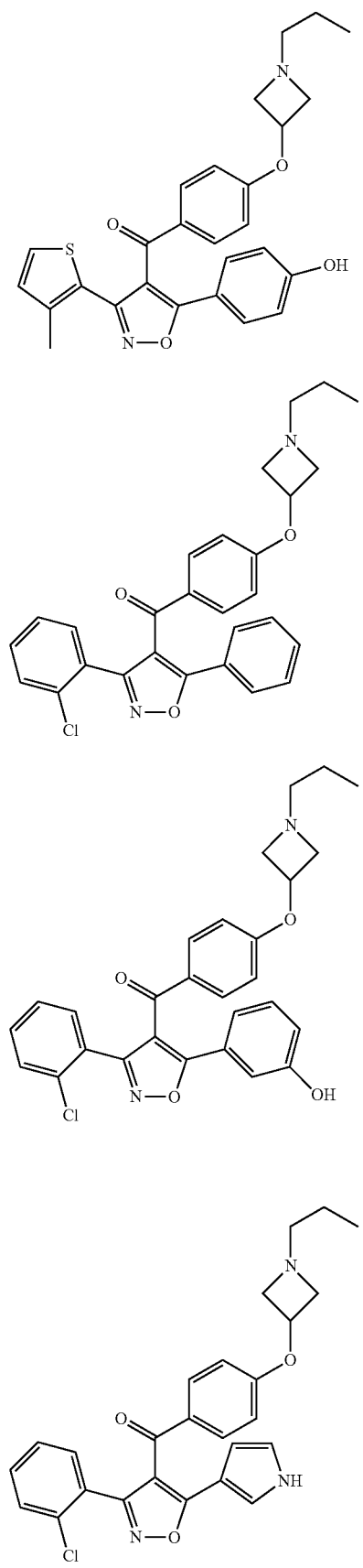
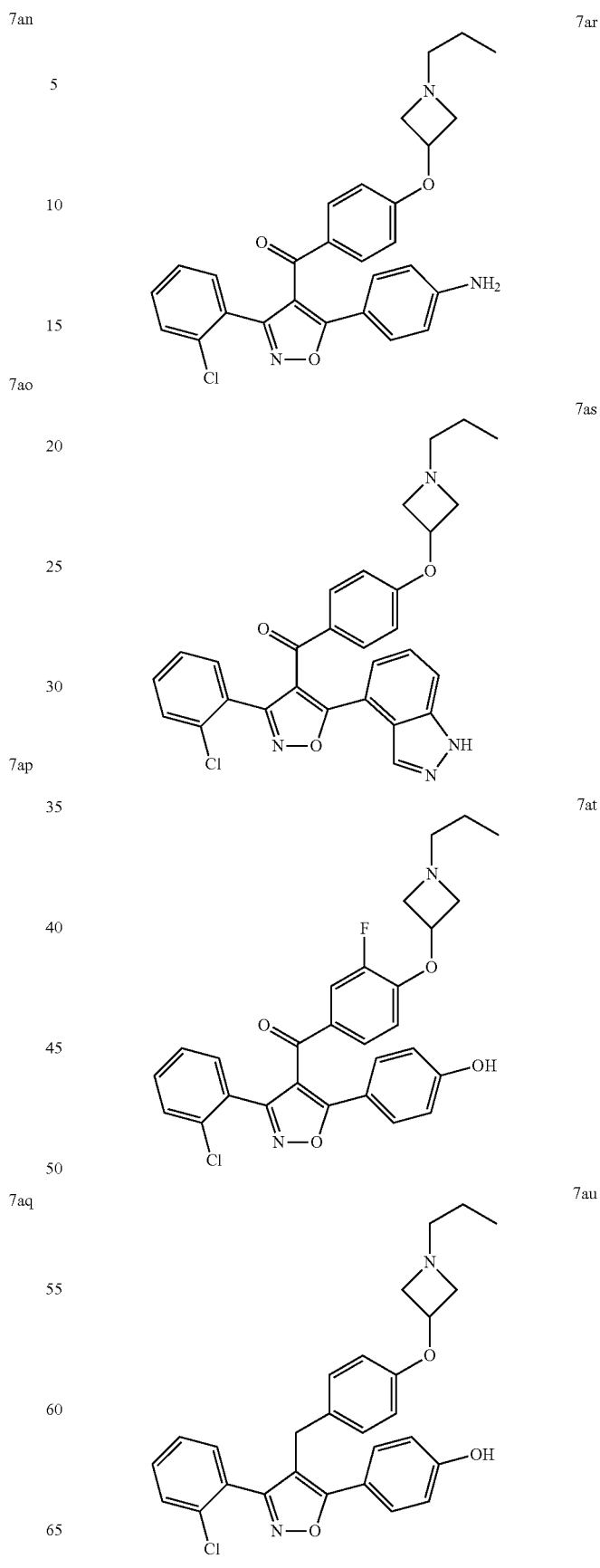

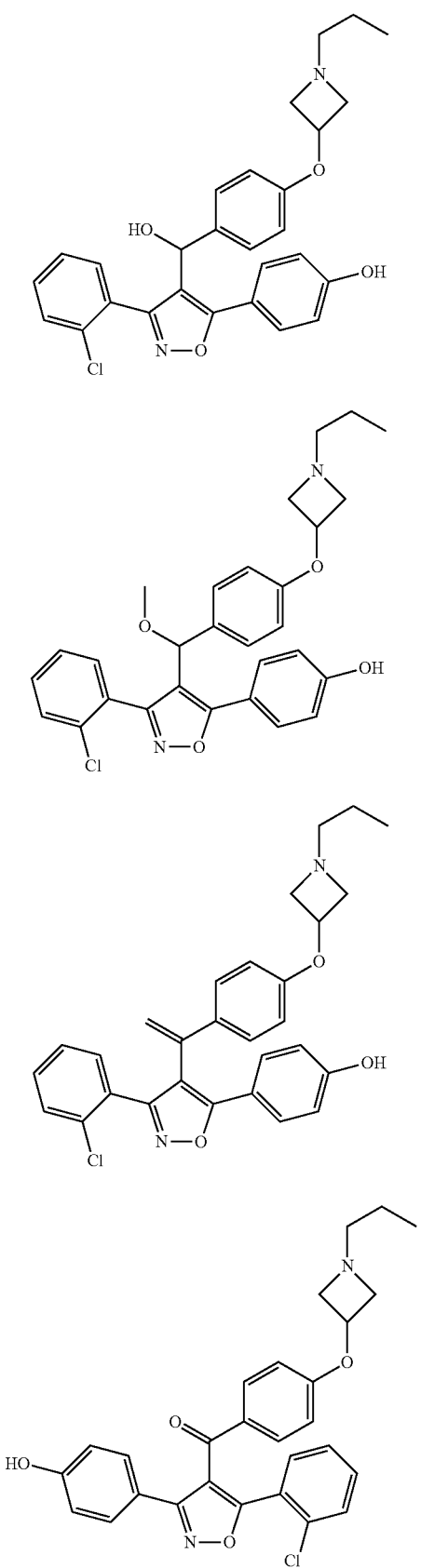
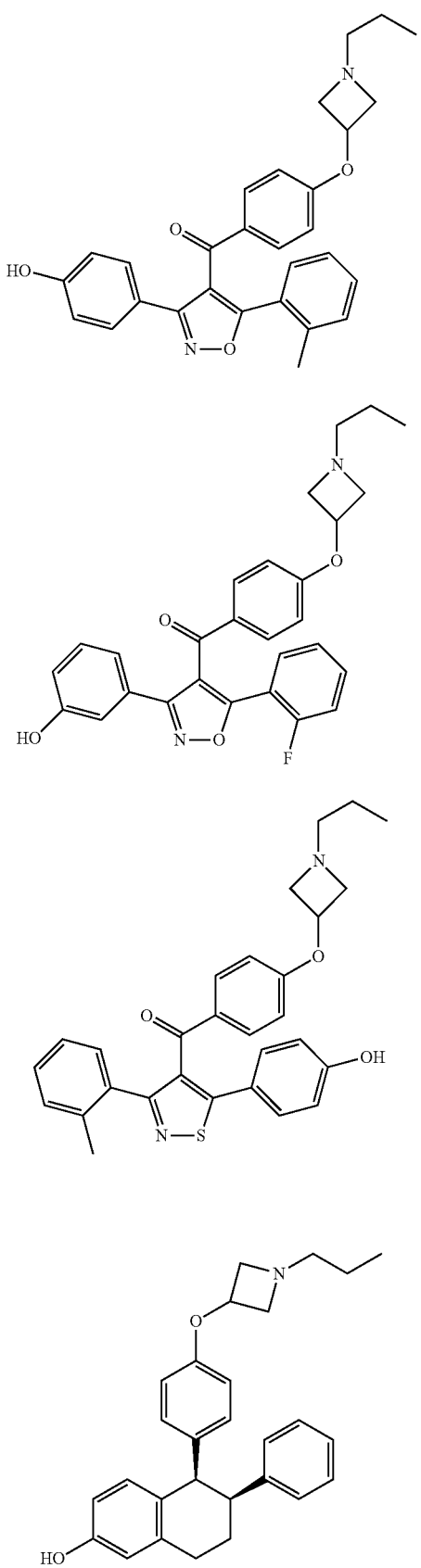

-continued

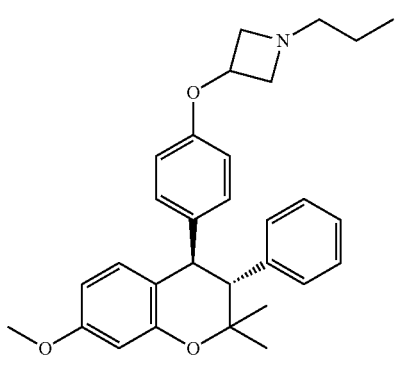
7bd

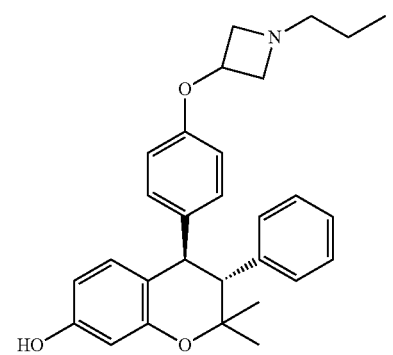
7be

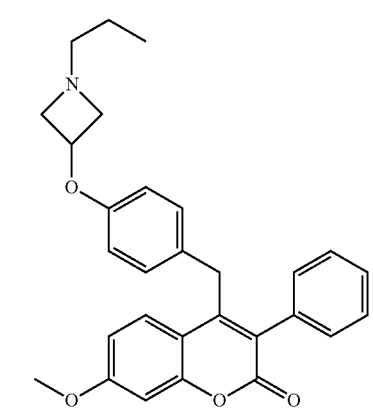
7bf

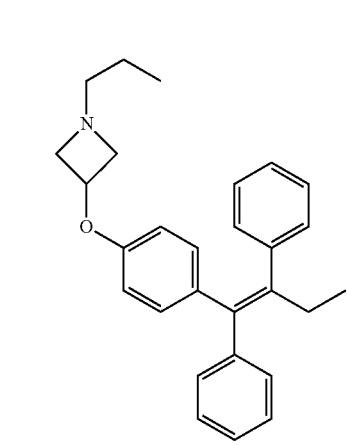
7bg

-continued

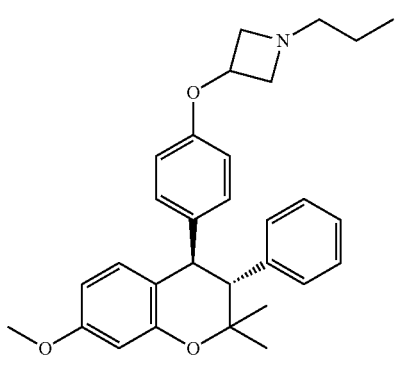
7bh

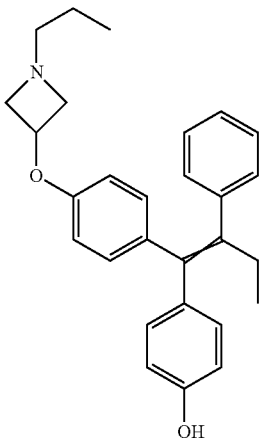
7bi

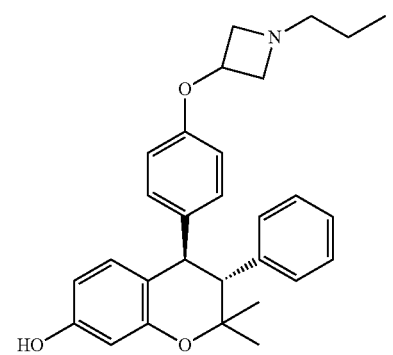
7bi

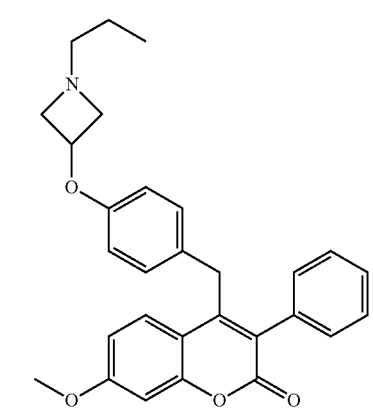
7bj

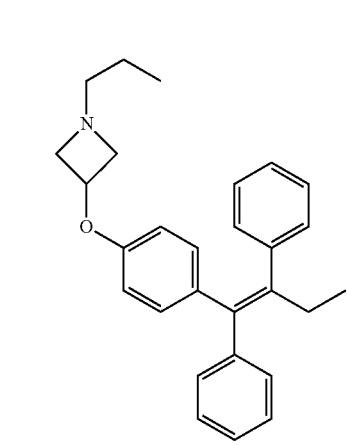

7. A pharmaceutical composition comprising an N-substituted azetidine derivative according to claim 1 and a pharmaceutically acceptable excipient.

8. A method of treating a disease or disorder selected from: ovulatory dysfunction, uterine cancer, endometrium cancer, ovarian cancer, endometriosis, osteoporosis, prostate cancer, benign prostatic hypertrophy, and breast cancer, in particular ER-positive breast cancer, more in particular ER-positive hormone treatment-resistant breast cancer comprising administering an N-substituted azetidine derivative according to claim 1.

9. The method of claim 8 wherein the disease or disorder is ER-positive, tamoxifen-resistant breast cancer.

* * * * *